United States Patent
Alanio et al.

(10) Patent No.: US 11,236,390 B2
(45) Date of Patent: Feb. 1, 2022

(54) **MEANS FOR DIAGNOSING, PREDICTING OR MONITORING *PNEUMOCYSTIS* PNEUMONIA**

(71) Applicants: INSTITUT PASTEUR, Paris (FR); ASSISTANCE PUBLIQUE—HOPITAUX DE PARIS, Paris (FR); UNIVERSITE PARIS DIDEROT—PARIS 7, Paris (FR)

(72) Inventors: Alexandre Alanio, Bourg-la-Reine (FR); Stéphane Bretagne, Verrieres le Buisson (FR); Françoise Dromer, Paris (FR); Aude Sturny-Leclere, Saint Cheron (FR); Benjamin Hommel, Paris (FR); Marion Benazra, Bretigny sur Orge (FR)

(73) Assignees: INSTITUT PASTEUR, Paris (FR); ASSISTANCE PUBLIQUE—HOPITAUX DE PARIS, Paris (FR); UNIVERSITE PARIS DIDEROT—PARIS 7, Paris (FR)

( * ) Notice: Subject to any disclaimer, the term of this patent is extended or adjusted under 35 U.S.C. 154(b) by 488 days.

(21) Appl. No.: 15/564,246

(22) PCT Filed: Apr. 15, 2016

(86) PCT No.: PCT/EP2016/058355
§ 371 (c)(1),
(2) Date: Oct. 4, 2017

(87) PCT Pub. No.: WO2016/166287
PCT Pub. Date: Oct. 20, 2016

(65) Prior Publication Data
US 2018/0127825 A1    May 10, 2018

(30) Foreign Application Priority Data

Apr. 15, 2015 (EP) .................................... 15305562

(51) Int. Cl.
*C12Q 1/6895* (2018.01)
*C12Q 1/6883* (2018.01)
(Continued)

(52) U.S. Cl.
CPC .......... *C12Q 1/6883* (2013.01); *C12Q 1/686* (2013.01); *C12Q 1/6895* (2013.01); *C40B 40/08* (2013.01);
(Continued)

(58) Field of Classification Search
CPC .... C12Q 1/686; C12Q 1/6883; C12Q 1/6895; C12Q 2600/112; C12Q 2600/158; C12Q 2600/16
See application file for complete search history.

(56) References Cited

FOREIGN PATENT DOCUMENTS

| WO | 2010/039819 A2 | 4/2010 |
| WO | 2014/071946 A1 | 5/2014 |

OTHER PUBLICATIONS

Helweg-Larsen, J. et al. BMC Infectious Diseases 2:28 (Nov. 2002). (Year: 2002).*

(Continued)

*Primary Examiner* — Diana B Johannsen
(74) *Attorney, Agent, or Firm* — Arrigo, Lee, Guttman & Mouta-Bellum LLP

(57) ABSTRACT

The application relates to means for diagnosing, predicting or monitoring *Pneumocystis* pneumonia (PCP). The means of the application are also suitable for determining or predicting the efficacy of a drug or treatment against PCP in a human patient. The means of involve the detection and/or quantification, more particularly the quantification, of the (Continued)

RNA transcripts of two different *P. jirovecii* mitochondrial genes. The first of said two *P. jirovecii* mitochondrial genes is the *P. jirovecii* gene, the sequence of which codes for the Cytb protein or the *P. jirovecii* mitochondrial Small Sub-Unit (mtSSU) gene. The second of said two *P. jirovecii* mitochondrial genes is a *P. jirovecii* gene, the sequence of which transcribes into a *P. jirovecii* ribosomal RNA, e.g., be the mitochondrial *P. jirovecii* Large Sub-Unit (mtLSU) gene.

19 Claims, 8 Drawing Sheets

Specification includes a Sequence Listing.

(51) Int. Cl.
  *C12Q 1/686* (2018.01)
  *C40B 40/08* (2006.01)
  *G01N 33/50* (2006.01)
(52) U.S. Cl.
  CPC ... *G01N 33/5008* (2013.01); *C12Q 2600/112* (2013.01); *C12Q 2600/158* (2013.01); *C12Q 2600/16* (2013.01)

(56) References Cited

OTHER PUBLICATIONS

Kaiser, K. et al. Journal of Microbiological Methods 45:113-118. (Year: 2001).*

Munro, S.A. et al. Nature Communications 5:5125 doi: 10.1038/ncomms6125 (Sep. 25, 2014). (Year: 2014).*

Jeong Hwan Shin et al: "Detection, Identification, and Distribution of Fungi in Bronchoalveolar Lavage Specimens by Use of Multi locus PCR Coupled with Electrospray Ionization/Mass Spectrometry", Journal of Clinical Microbiology, vol. 51, No. 1. Oct. 24, 2012 (Oct. 24, 2012), pp. 136-141.

Alanio et al.: "Real-time PCR assay-based strategy for differentiation between active Pneumocystis jirovecii pneumonia and colonization in immunocompromised patients", Clin Microbiol Infect, vol. 17, 2011, pp. 1531-1537.

Revathy M et al: "Evaluation of PCR based DNA sequencing targeting mitochondrial larger subunit (mtLSU) region for the rapid detection of Pneumocystis jirovecii in sputum from HIV positive patients," BMC Infectious Diseases, Biomed Central, London, GB, vol. 12, No. Suppl 1, May 4, 2012.

Nicaise G Tuikue Ndam et al: "Development of a Real-Time PCR-Based Fluorescence Assay for Rapid Detection of Point Mutations in Pneumocystis jirovecii Dihydropteroate Synthase Gene", J. Eukaryot. Microbiol, Jan. 1, 2003.

L. Ma et al: "Sequencing and characterization of the complete mitochondrial genomes of three *Pneumocystis* species provide new insights into divergence between human and rodent Pneumocystis", The FASEB Journal, vol. 27, No. 5, Feb. 7, 2013.

Charles F. Thomas et al: "Current insights into the biology and pathogenesis of Pneumocystis pneumonia", Nature Reviews Microbiology, vol. 5, No. 4, Apr. 1, 2007.

Extended European Search Report, EP 15305562.9, dated Sep. 30, 2015.

International Search Report, PCT/EP2016/058355, dated Aug. 9, 2016.

* cited by examiner

MEANS FOR DIAGNOSING, PREDICTING OR MONITORING *PNEUMOCYSTIS* PNEUMONIA

FIELD OF THE INVENTION

The application relates to means for diagnosing, predicting or monitoring *Pneumocystis* pneumonia (PCP). The means of the application involve the detection and/or quantification, more particularly the quantification, of the RNA transcripts of two different *P. jirovecii* mitochondrial genes.

The means of the application are also suitable for determining or predicting the efficacy of a drug or treatment against PCP in a human patient or for determining whether PCP regresses or has been treated in a human patient who has been diagnosed to have PCP and who is receiving or has received a drug or treatment against PCP.

BACKGROUND OF THE INVENTION

*PneumoCystis* Pneumonia (PCP) is an opportunistic infection due to the ascomycetous fungus *Pneumocystis jirovecii*. This pathogen is specific for humans whereas related species exists for other terrestrial mammals, and growing evidence suggest that *P. jirovecii* could be considered as a commensal of human respiratory tract. It lives and thrives at the surface of the alveolar cells (type I pneumocytes) and can be found typically as two main forms: (i) the trophic form that undergo asexual multiplication by binary fission and (ii) ascus (cyst) containing eight ascospores that is the result of the sexual mode of replication. The complete life cycle of *Pneumocystis carinii* has been studied in rats. Experiments in animals suggest that *Pneumocystis* is transmissible from host to host with immunocompetent individuals as the most important reservoir and asci as the potential agent of transmission. Epidemiological and experimental data suggests that *P. jirovecii* is also a transmissible organism in humans.

HIV-infected individuals with low CD4 counts are at risk of developing PCP. Despite highly effective prophylaxis with cotrimoxazole (association of a Dihydrofolate reductase inhibitor (trimethoprim) and of a sulfonamide antibiotic (sulfamethoxazole)) and highly active anti-retroviral treatments, PCP remains one of the most prevalent infections in patients with AIDS. PCP also occurs in non-HIV immunocompromised patients, including patients with hematological or solid malignancies, transplant recipients, and those receiving immunosuppressive treatments for autoimmune or inflammatory diseases. In non-HIV immunocompromised patients, PCP is typically more acute and severe than in HIV patients. PCP diagnosis is also harder since the average fungal charge is lower in non-HIV patients than in HIV patients.

Overall, PCP carries a mortality rate of 35 to 55% in non-HIV immunocompromised patients, compared to 10 to 20% in HIV-infected patients.

Diagnosis of PCP usually relies on microscopic demonstration of *P. jirovecii* in respiratory specimens using various staining methods that includes conventional staining (Calcofluor White, Toluidine Blue O, Gomori methamine, Giemsa staining) and anti-*P. jirovecii* immunofluorescence assays (IFA) (direct or indirect IFA). It is known for a long time that immunofluorescence is more sensitive than conventional staining. Alternatively, in the 1990's, two methods have been developed: beta-D-glucan (BDG) detection and PCR.

The lack of sensitivity of microscopic methods due to low burden of *P. jirovecii* in non-HIV immunocompromised patients has justified the development of diagnostic PCR-based methods in the early 1990's to detect DNA in clinical samples rather than the microorganism itself. Initially, DNA detection aimed also at increasing sensitivity of *P. jirovecii* detection to avoid invasive procedure such as BronchoAlveolar Lavage (BAL) in patients suspected of PCP with the ambition to use induced sputa (IS) and/or upper respiratory specimens (URS, nasopharyngeal aspirate, oral washes or nasal swab) as diagnostic specimens. These methods were more sensitive and reproducible than microscopic detection (conventional staining and/or immunofluorescence), considered as gold-standard test in respiratory samples such as BronchoAlveolar Lavage Fluid (BALF) or induced sputa at that time.

Single (sPCR) and nested end point (nPCR) formats used initially for DNA detection were progressively replaced by the quantitative real-time PCR (qPCR) format, where the PCR products is detected and quantified during amplification without opening of the reaction tube. The main advantages of this format are preventing false positives due to environmental contamination with previously amplified products, and to provide rapid quantitative results. Subgroup analysis regarding the PCR format was performed in the meta-analyses and showed higher sensitivity and specificity in qPCR assays compared to the global analysis. In addition, recommendations for diagnostic PCR already exist, highlighting the necessity to use real-time PCR format.

The difference in performance reported for different PCR assays could be explained by the different DNA targets used for amplification and the primer designs. Indeed, most of the authors have developed their own primers, although generally designed to amplify a multicopy gene, which increase the sensitivity compared to a single copy gene. The *P. jirovecii* mitochondrial Large Sub-Unit ribosomal RNA (rRNA) gene (mtLSU) is the most commonly used. The multicopy Major Surface Antigen (MSG) gene was also targeted in various reports. Multiple single copy nuclear gene were also used such as 18S ribosomal DNA (rDNA), 5S rDNA, Internal transcribed spacer (ITS), DHPS, KEX, HSP70, Beta-TUBulin (BTUB) and CDC2. Indeed, ribosomal RNA genes cluster is unique in *Pneumocystis*.

Comparison of analytical performance could be easily achieved using the quantification results of external quality controls. A comparison of three PCR assays using MSG (multicopy) and DHPS (single copy) target genes demonstrated the transferability of the results.

However, PCR revealed the possibility to detect *Pneumocystis* DNA in pulmonary specimens from immunocompromised individuals without clinical signs or symptoms of PCP. This phenomenon was called *P. jirovecii* colonization or carriage. For this reason, PCR is not completely accepted as a diagnostic criterion for PCP, although the sensitivity of PCR assays is higher than microscopy and PCR was cost-effective in non-invasive specimens.

One simple method to discriminate active *Pneumocystis* pneumonia from *P. jirovecii* carriage in respiratory samples of patients at risk of PCP is to determine quantitative thresholds. Since PCR is much more sensitive than microscopy, to define thresholds for assessing the diagnosis is crucial and cannot be performed without reliable quantification. Real-time quantitative PCR refers to real-time PCR that is able to quantify the amount of DNA in the extract using calibration curves based on reference DNA (plasmid), expressed as copy/volume unit. However, quantitative results can be expressed with other units. Alternatively, some authors use the crude qPCR results (as quantification cycle, Cq, Ct, or Cp), or some others translate it into a number of microorganisms based on counts (for example trophic form equivalent). No international standard qPCR assay and no threshold are currently consensual. Large international studies, or at least prospective studies, are highly needed to allow technical validation of this tool. Thereafter, the use of qPCR for clinical interpretation of qPCR results would be possible and validated.

For samples harboring positive IFA, qPCR and microscopic quantification, as evaluated as the number of cysts (often expressed as +, ++ or +++), gave similar results. When qPCR results are in congruence with IFA, there is little question about the interpretation of the results. However, there is an overlap around the sensitivity limit of IFA, with some samples IFA negative and PCR positive whereas other samples are IFA positive with a lower *P. jirovecii* DNA content. A consensus of the lowest qPCR results corresponding to the IFA positive samples harboring the lowest fungal load is almost impossible since IFA is dependent of the examiner and the quality of the sample. On the other end of the spectrum, there is little doubt about the interpretation of the qPCR negative results. The negative predictive value of PCR assays has reached a consensus. The only point to be checked is the correct amplification of the internal control to avoid false negative results. Discrepancies appear for the IFA-negative qPCR-positive results. Some authors propose a grey zone. For instance, two cut-off values of 120 and 1900 trophic form equivalent/mL were proposed to discriminate active pneumonia from carriage, with a grey zone between them.

There is a need for new means for diagnosing, predicting or monitoring PCP, more particularly for means, which discriminate PCP from *P. jirovecii* carriage. Therefore, we developed a new PCR method for the detection of *Pneumocystis* RNA.

Our test is based on the detection and the quantification of the RNA transcripts of two genes of *Pneumocystis jirovecii* in the BAL fluid of patients.

SUMMARY OF THE INVENTION

The application provides means, which are notably useful for diagnosing, predicting or monitoring *Pneumocystis* pneumonia (PCP).

The means of the application notably enable to discriminate a PCP patient from a *P. jirovecii* carrier, who does not have or does not develop PCP, including when the patient is HIV-negative. The PCP status of HIV-negative human patients is especially difficult to determine, because the *P. jirovecii* charge of these patients is lower than that of HIV-positive human patients. The means of the application may thereby avoid that said *P. jirovecii* carriers receive an unnecessary PCP treatment.

The means of the application involve the detection and/or quantification, more particularly the quantification, of the RNA transcripts of two different *P. jirovecii* mitochondrial genes. The means of the application involve more particularly determining the ratio of the RNA transcripts of one of said two different *P. jirovecii* mitochondrial genes (hereinafter the first *P. jirovecii* mitochondrial gene) to the RNA transcripts of the other of said two different *P. jirovecii* mitochondrial genes (hereinafter the second *P. jirovecii* mitochondrial gene).

Each of the two different *P. jirovecii* mitochondrial genes are independently selected from the group consisting of the *P. jirovecii* gene (SEQ ID NO: 3), the sequence of which codes for the Cytb protein, and the *P. jirovecii* genes, the respective sequences of which transcribe into a *P. jirovecii* ribosomal RNA, such as the mitochondrial *P. jirovecii* Large Sub-Unit (mtLSU) gene (SEQ ID NO: 1) and the mitochondrial *P. jirovecii* Small Sub-Unit (mtSSU) gene (SEQ ID NO: 2).

At least one of said two different *P. jirovecii* mitochondrial genes is a *P. jirovecii* gene, the sequence of which transcribes into a *P. jirovecii* ribosomal RNA, such as the mtLSU gene or the mtSSU gene.

More particularly, at least one of said two different *P. jirovecii* mitochondrial genes is the mtLSU gene.

For example, the first *P. jirovecii* mitochondrial gene of said ratio is the *P. jirovecii* gene, the sequence of which codes for the Cytb protein, or is the mtSSU gene.

For example, the second *P. jirovecii* mitochondrial gene of said ratio is the mtSSU gene or the mtLSU gene (while still being different from the first *P. jirovecii* mitochondrial gene of said ratio), more particularly the mtLSU gene.

For example, the first *P. jirovecii* mitochondrial gene is the *P. jirovecii* gene, the sequence of which codes for the Cytb protein, and the second *P. jirovecii* mitochondrial gene is a *P. jirovecii* gene, the sequence of which transcribes into a *P. jirovecii* ribosomal RNA, such as the mtLSU gene or the mtSSU gene [ratio Cytb/(mtLSU or mtSSU), more particularly ratio Cytb/mtLSU]. For example, the first *P. jirovecii* mitochondrial gene is the mtSSU gene, and the second *P. jirovecii* mitochondrial gene is the mtLSU gene [ratio mtSSU/mtLSU].

The means of the application are notably suitable
  for diagnosing or predicting PneumoCystis Pneumonia (PCP), more particularly for diagnosing or predicting whether a human patient (more particularly a human patient, who is a *Pneumocystis jirovecii* carrier) has or develops PCP, or
  for determining or predicting the efficacy of a drug or treatment against PCP in a human patient (more particularly a human patient, who is a *Pneumocystis jirovecii* carrier), or
  for determining whether PCP regresses or has been treated in a human patient who has been diagnosed to have PCP and who is receiving or has received a drug or treatment against PCP.

The means of the application comprises methods, products (e.g., primers and/or probes), association(s) or combination(s) of at least two of these products, as well as kit(s) and composition(s) comprising at least one of said products.

The means of the application also comprises solid supports such as microarray, nanoarray, chip, onto which at least one of said product is attached, as well as nucleic acid library(ies) which are suitable for the quantification of a *P. jirovecii* transcriptome, computer program product(s), computer device(s) and kit(s) for use in the treatment and/or prevention and/or palliation of PCP in a human patient.

DETAILED DESCRIPTION OF THE INVENTION

Figure 1:
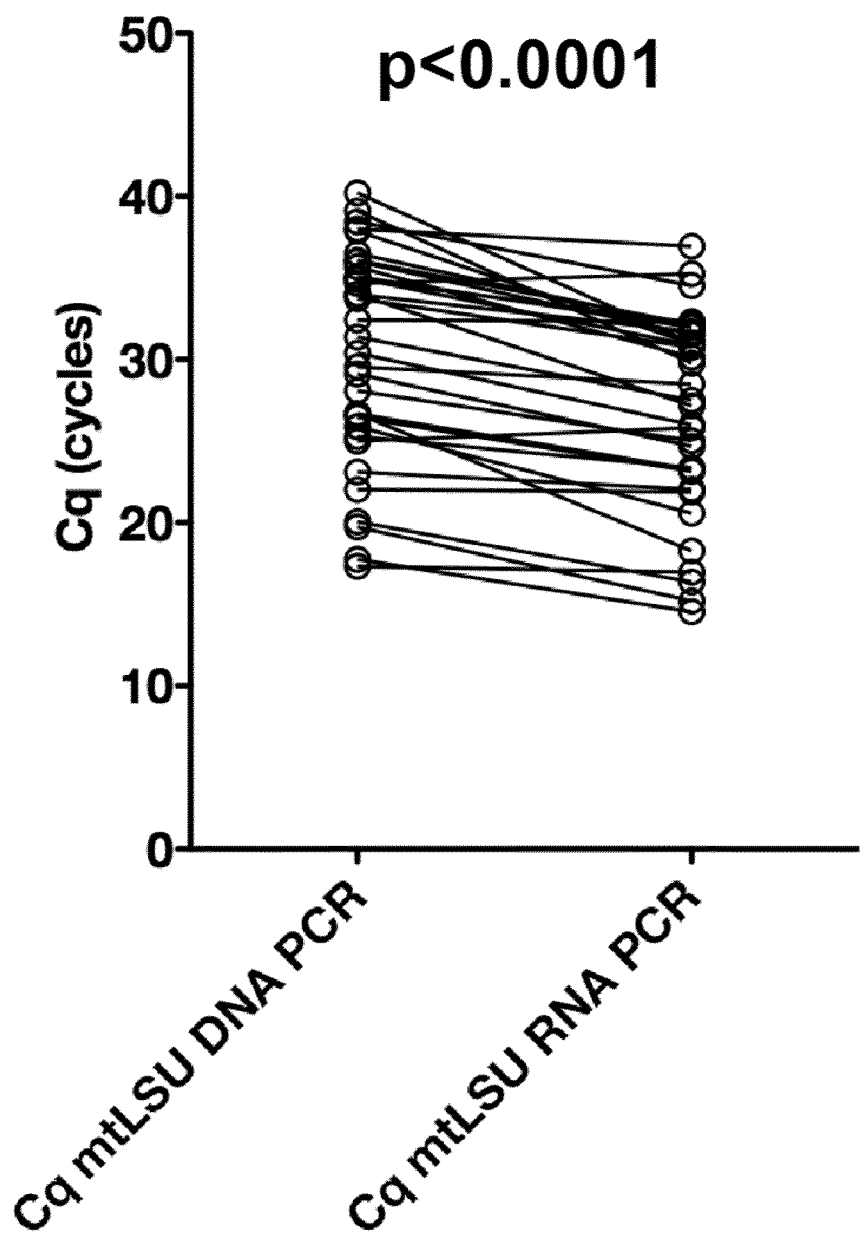
FIG. 1. Comparison of mtLSU quantification thresholds obtained with DNA (Cq mtLSU DNA PCR) or RNA amplification (Cq mtLSU RNA PCR) in BALF of patients. The mean loss of Cq is 3.58 (95%CI: 2.68-4.47), corresponding approximately to about a 10 fold higher expression for RNA.

The present application relates to the subject-matter as defined in the claims as filed and as herein described.

In the application, unless specified otherwise or unless a context dictates otherwise, all the terms have their ordinary meaning in the relevant field(s).

The application provides means, which involve the detection and/or quantification, more particularly the quantification, of the RNA transcripts of two different *P. jirovecii* mitochondrial genes.

An aspect of the application is that the means of the application are based on the analysis of RNA transcripts, and not on the analysis of DNA. A further aspect of the application is that the RNA transcripts of the application are those of (*P. jirovecii*) mitochondrial genes.

The means of the application involve more particularly determining the ratio of the RNA transcripts of one of said two different *P. jirovecii* mitochondrial genes (hereinafter the first *P. jirovecii* mitochondrial gene) to the RNA transcripts of the other of said two different *P. jirovecii* mitochondrial genes (hereinafter the second *P. jirovecii* mitochondrial gene).

Each of the two different *P. jirovecii* mitochondrial genes are independently selected from the group consisting of
the *P. jirovecii* gene (SEQ ID NO: 3), the sequence of which codes for the Cytb protein, and
the *P. jirovecii* genes, the respective sequences of which transcribe into a *P. jirovecii* ribosomal RNA, such as the mitochondrial *P. jirovecii* Large Sub-Unit (mtLSU) gene (SEQ ID NO: 1) and the mitochondrial *P. jirovecii* Small Sub-Unit (mtSSU) gene (SEQ ID NO: 2).

At least one of said two different *P. jirovecii* mitochondrial genes is a *P. jirovecii* gene, the sequence of which transcribes into a *P. jirovecii* ribosomal RNA, such as the mtLSU gene or the mtSSU gene.

According to an aspect of the application, at least one of said two different *P. jirovecii* mitochondrial genes is the mtLSU gene.

According to an aspect of the application, the first of said two *P. jirovecii* mitochondrial genes is the *P. jirovecii* gene, the sequence of which codes for the Cytb protein (SEQ ID NO: 3).

The second of said two *P. jirovecii* mitochondrial genes is a *P. jirovecii* gene, the sequence of which transcribes into a *P. jirovecii* ribosomal RNA, such as the mtLSU gene (SEQ ID NO: 1) or the mtSSU gene (SEQ ID NO: 2), more particularly the mtLSU gene.

According to an aspect of the application, the first of said two *P. jirovecii* mitochondrial genes is the mtSSU gene.

The second of said two *P. jirovecii* mitochondrial genes is the mtLSU gene, or the *P. jirovecii* gene, the sequence of which codes for the Cytb protein, more particularly the mtLSU gene.

According to an aspect of the application, the first of said two *P. jirovecii* mitochondrial genes is the mtLSU gene.

The second of said two *P. jirovecii* mitochondrial genes is the mtSSU gene, or the *P. jirovecii* gene, the sequence of which codes for the Cytb protein, more particularly the mtSSU gene.

The means of the application are notably suitable
for diagnosing or predicting *PneumoCystis* Pneumonia (PCP), more particularly for diagnosing or predicting whether a human patient (more particularly a human patient, who is a *Pneumocystis jirovecii* carrier) has or develops PCP, or
for determining or predicting the efficacy of a drug or treatment against PCP in a human patient (more particularly a human patient, who is a *Pneumocystis jirovecii* carrier), or
for determining whether PCP regresses or has been treated in a human patient who has been diagnosed to have PCP and who is receiving or has received a drug or treatment against PCP.

Advantageously, the means of the invention are sufficiently reliable to determine the PCP status of a human patient, who is HIV-negative, more particularly a HIV-negative and immunocompromised human patient. The PCP status of HIV-negative human patients is especially difficult to determine, because the *P. jirovecii* charge of these patients is lower than that of HIV-positive human patients.

The quantification of the RNA transcripts of said two different *P. jirovecii* mitochondrial genes may be achieved by any means that the skilled person may found appropriate. Nevertheless, the application provides Reverse-Transcriptase Polymerase Chain Reaction (RT-PCR) means, which RT-PCR means can be implemented in real-time.

The application relates to an in vitro method for diagnosing or predicting *PneumoCystis* Pneumonia (PCP), more particularly an in vitro method for diagnosing or predicting whether a human patient (more particularly a human patient, who is a *Pneumocystis jirovecii* carrier) has or develops PCP, wherein said method comprises i. in the RNA material of a sample of biological fluid previously obtained from the respiratory tract of said human patient, detecting and/or quantifying the (number of or the concentration of) RNA transcripts of (each of) two different *P. jirovecii* mitochondrial genes, more particularly quantifying the (number of or the concentration of) RNA transcripts of (each of) two different *P. jirovecii* mitochondrial genes to obtain a value of quantification of the RNA transcripts of a first *P. jirovecii* mitochondrial gene and a value of quantification of the RNA transcripts of a second *P. jirovecii* mitochondrial gene, ii. calculating the ratio of the value of quantification of the RNA transcripts of said first *P. jirovecii* mitochondrial gene of i. to the value of quantification of the RNA transcripts of said second *P. jirovecii* mitochondrial gene of i., and iii. comparing the value of the ratio of ii. to a threshold (numerical) value, wherein said human patient is diagnosed or predicted to be at high risk of having or developing PCP or to be at low risk of having or developing PCP depending on whether the value of the ratio of ii. is equal to or lower than said threshold value, or whether the value of the ratio of ii. is higher than said threshold value.

When the first of said two *P. jirovecii* mitochondrial genes is the *P. jirovecii* gene, the sequence of which codes for the Cytb protein (SEQ ID NO: 3) and the second of said two *P. jirovecii* mitochondrial genes is the mtLSU or mtSSU gene, more particularly the mtLSU gene, or when the first of said two *P. jirovecii* mitochondrial genes is the mtSSU gene and the second of said two *P. jirovecii* mitochondrial genes is the mtLSU gene, said step iii. can be the step of comparing the ratio of ii. to a threshold (numerical) value, wherein, when the value of the ratio of ii. is equal to or lower than (more particularly lower than) said threshold value, said human patient is diagnosed or predicted to be at high risk of having or developing PCP, wherein, when the value of the ratio of ii. is higher than said threshold value, said human patient is diagnosed or predicted to be at low risk of having or developing PCP.

Of course, inverting the first and second mitochondrial genes in the ratio results in accordingly inverting the threshold value and the conclusion that results from the comparison of the ratio to the threshold value.

Therefore, when the first of said two *P. jirovecii* mitochondrial genes is the mtLSU gene and the second of said two *P. jirovecii* mitochondrial genes is the *P. jirovecii* gene, the sequence of which codes for the Cytb protein, or is the mtSSU gene, or when the first of said two *P. jirovecii* mitochondrial genes is the mtSSU gene and the second of said two *P. jirovecii* mitochondrial genes is the *P. jirovecii* gene, the sequence of which codes for the Cytb protein, said step iii. can be the step of comparing the ratio of ii. to a threshold (numerical) value, wherein, when the value of the ratio of ii. is higher or equal than (more particularly higher than) said threshold value, said human patient is diagnosed or predicted to be at high risk of having or developing PCP, wherein, when the value of the ratio of ii. is lower than said threshold value, said human patient is diagnosed or predicted to be at low risk of having or developing PCP.

Said threshold value may e.g., have been predetermined by comparing the values, or the distribution of the values, that the ratio of the value of quantification of the RNA transcripts of said first *P. jirovecii* mitochondrial gene to the value of quantification of the RNA transcripts of said second *P. jirovecii* mitochondrial gene takes in reference human cohorts of *P. jirovecii* carriers, who have been pre-established as a function of their status of:

*P. jirovecii* carriers, who have or develop PCP, or of

*P. jirovecii* carriers, who do not have and do not develop PCP, in order to classify said human patient into that of those reference cohorts to which it has the highest probability of belonging.

The reference human cohort of *P. jirovecii* carriers, who have or develop PCP, and the reference human cohort of *P. jirovecii* carriers, who do not have and do not develop PCP, may each e.g., comprise more than 100 humans. A human carrier of *P. jirovecii* is classified in either one of said two reference cohorts by any means that the skilled person may find appropriate. For example, said means may comprise the analysis of the clinical, radiological and biological features (including microscopical detection of absence or presence of *P. jirovecii*) of human individuals by two independent experts, e.g., a pneumologist and an infectious disease specialist (cf. examples and Table 1 below), and, for each of said human individuals, the concurrent conclusion of either presence of PCP (proven, probable or possible PCP, more particularly proven PCP), or of absence of PCP.

The application also relates to an in vitro method for determining or predicting the efficacy of a drug or treatment against PCP in a human patient, who is a *Pneumocystis jirovecii* carrier and who has been diagnosed to have or to develop PCP, wherein said method comprises quantifying (the number of or the concentration of) RNA transcripts in the RNA material of a sample of biological fluid previously obtained from the respiratory tract of said human patient at a first point in time as well as at a second point in time, wherein said second point in time is later than said first point in time, wherein at least one of said first and second points in time is comprised in a time period during which said human patient is receiving said drug or treatment, wherein said RNA transcripts are the (respective) RNA transcripts of two different *P. jirovecii* mitochondrial genes, to obtain the value of quantification of the RNA transcripts of said first *P. jirovecii* mitochondrial gene at said first point in time and at said second point in time as well as the value of quantification of the RNA transcripts of said second *P. jirovecii* mitochondrial gene at said first point in time and at said second point in time, respectively, calculating the ratio of the value of quantification of the RNA transcripts of said first *P. jirovecii* mitochondrial gene to the value of quantification of RNA transcripts of said second *P. jirovecii* mitochondrial gene, to obtain the value of said ratio at said first point in time as well as its value at said second point in time, and comparing the value of said ratio at said second point in time to its value at said first point in time, wherein an increase or a decrease of the value of said ratio at said second point in time compared to said first point in time is indicative that said treatment or drug is or will be efficient to treat or alleviate PCP in said human patient.

When the first of said two *P. jirovecii* mitochondrial genes is the *P. jirovecii* gene, the sequence of which codes for the Cytb protein, and the second of said two *P. jirovecii* mitochondrial genes is the mtLSU gene or the mtSSU gene, more particularly the mtLSU gene, or when the first of said two *P. jirovecii* mitochondrial genes is the mtSSU gene and the second of said two *P. jirovecii* mitochondrial genes is the mtLSU gene, it is an increase of the value of said ratio at said second point in time compared to said first point in time that is indicative that said treatment or drug is or will be efficient to treat or alleviate PCP in said human patient. The absence of increase, more particularly a decrease, of the value of said ratio at said second point in time compared to said first point in time may be or is indicative that said treatment or drug is not or will not be efficient to treat or alleviate PCP in said human patient.

Of course, inverting the first and second mitochondrial genes in the ratio results in accordingly inverting the threshold value and the conclusion that results from the comparison of the ratio to the threshold value.

Therefore, when the first of said two *P. jirovecii* mitochondrial genes is the mtLSU gene and the second of said two *P. jirovecii* mitochondrial genes is the *P. jirovecii* gene, the sequence of which codes for the Cytb protein, or is the mtSSU gene, or when the first of said two *P. jirovecii* mitochondrial genes is the mtSSU gene and the second of said two *P. jirovecii* mitochondrial genes is the *P. jirovecii* gene, the sequence of which codes for the Cytb protein, it is a decrease of the value of said ratio at said second point in time compared to said first point in time that is indicative that said treatment or drug is or will be efficient to treat or alleviate PCP in said human patient. The absence of decrease, more particularly an increase, of the value of said ratio at said second point in time compared to said first point in time may be or is indicative that said treatment or drug is not or will not be efficient to treat or alleviate PCP in said human patient.

The application also relates to an in vitro method for determining whether PCP regresses or has been treated in a human patient who has been diagnosed to have PCP and who is receiving or has received a drug or treatment against PCP, wherein said method comprises quantifying (the number of or the concentration of) RNA transcripts in the RNA material of a sample of biological fluid previously obtained from the respiratory tract of said human patient at a first point in time as well as at a second point in time, wherein said second point in time is later than said first point in time, wherein at least one of said first and second points in time is comprised in a time period during which said human patient is receiving said drug or treatment, wherein said RNA transcripts are the (respective) RNA transcripts of two different *P. jirovecii* mitochondrial genes, to obtain the value of quantification of the RNA transcripts of said first *P. jirovecii* mitochondrial gene at said first point in time and at said second point in time as well as the value of quantification of the RNA transcripts of said second *P. jirovecii* mitochondrial gene at said first point in time and at said second point in time, respectively, calculating the ratio of the value of quantification of the RNA transcripts of said first *P. jirovecii* mitochondrial gene to the value of quantification of RNA transcripts of said second *P. jirovecii* mitochondrial gene, to obtain the value of said ratio at said first point in time as well as its value at said second point in time, and comparing the value of said ratio at said second point in time to its value at said first point in time, wherein an increase or a decrease of the value of said ratio at said second point in time compared to said first point in time is indicative that PCP regresses or has been treated in said human patient.

When the first of said two *P. jirovecii* mitochondrial genes is the *P. jirovecii* gene, the sequence of which codes for the Cytb protein (SEQ ID NO: 3), and the second of said two *P. jirovecii* mitochondrial genes is the mtLSU gene or the mtSSU gene, more particularly the mtLSU gene, or when the first of said two *P. jirovecii* mitochondrial genes is the mtSSU gene and the second of said two *P. jirovecii* mitochondrial genes is the mtLSU gene, it is an increase of the value of said ratio at said second point in time compared to said first point in time that is indicative that PCP regresses or has been treated in said human patient. The absence of increase, more particularly a decrease, of the value of said ratio at said second point in time compared to said first point in time may be or is indicative that PCP does not regress or does not have been treated in said human patient.

Of course, inverting the first and second mitochondrial genes in the ratio results in accordingly inverting the threshold value and the conclusion that results from the comparison of the ratio to the threshold value.

Therefore, when the first of said two *P. jirovecii* mitochondrial genes is the mtLSU gene and the second of said two *P. jirovecii* mitochondrial genes is the *P. jirovecii* gene, the sequence of which codes for the Cytb protein, or is the mtSSU gene, or when the first of said two *P. jirovecii* mitochondrial genes is the mtSSU gene and the second first of said two *P. jirovecii* mitochondrial genes is the *P. jirovecii* gene, the sequence of which codes for the Cytb protein, it is a decrease of the value of said ratio at said second point in time compared to said first point in time that is indicative that PCP regresses or has been treated in said human patient. The absence of decrease, more particularly an increase, of the value of said ratio at said second point in time compared to said first point in time may be or is indicative that PCP does not regress or does not have been treated in said human patient.

When the first of said two *P. jirovecii* mitochondrial genes is the *P. jirovecii* gene, the sequence of which codes for the Cytb protein, the second of said two *P. jirovecii* mitochondrial genes can e.g., be a *P. jirovecii* gene, the sequence of which transcribes into a *P. jirovecii* ribosomal RNA, such as the mtLSU gene (SEQ ID NO: 1) or the mtSSU gene (SEQ ID NO: 2), more particularly the mtLSU gene.

When the first of said two *P. jirovecii* mitochondrial genes is the mtSSU gene, the second of said two *P. jirovecii* mitochondrial genes can e.g., be the mtLSU gene.

According to an aspect of the application, said second *P. jirovecii* ribosomal RNA is the mitochondrial *P. jirovecii* Large Sub-Unit (mtLSU) gene.

According to an aspect of the application, said first *P. jirovecii* ribosomal RNA is the *P. jirovecii* gene, the sequence of which codes for the Cytb protein, or is the mitochondrial *P. jirovecii* Small Sub-Unit (mtSSU) gene.

Advantageously, the respective RNA transcripts of said two different *P. jirovecii* mitochondrial genes are quantified in the RNA material of the same sample of biological fluid.

The RNA material of said sample of biological fluid can be extracted and/or purified from the sample. RNA extraction means and RNA purification means are known to the person of ordinary skill in the art. For example, RNA extraction means comprise cell lysis reagent(s) and/or buffer(s). For example, RNA purification means comprise silica membrane.

Advantageously, the RNA material of said sample of biological fluid is purified by silica membrane filtration of said sample of biological fluid.

The means of the application may further comprise a control of nucleic acid extraction and/or purification, more particularly an internal control of nucleic acid extraction and/or purification. More particularly, the means of the application may further comprise a control of RNA extraction and/or purification, more particularly an internal control of RNA extraction and/or purification.

More particularly, the means of the application may further comprise a RNA acting as an internal control of RNA extraction and/or purification, more particularly an artificial or exogenous RNA, more particularly a RNA acting as an Internal Extraction Control RNA (IECR) (cf. the example 2 below), or may further comprise a cell which comprises such a RNA (e.g., by genetic engineering).

Said RNA or IECR may e.g., be a RNA sequence (e.g., a RNA sequence of 30-500 nucleotides), which is not a human or fungal nucleic acid sequence, more preferably which has less than 60% (e.g., less than 50%, less than 40%, less than 30%, less than 20%, less than 10%, less than 1%) identity to any human or fungal nucleic acid sequence. Examples of IECR are commercially available. Examples of IECR include:
- the RNA extraction control commercialized by BIOLINE (BIOLINE USA Inc.; 305 Constitution Dr.; TAUNTON; Mass. 027080; U.S.A.) under catalog number BIO-38040 or BIO-35040,
- the AMBION® ERCC RNA Spike-In Controls, which are commercialized by LIFE TECHNOLOGIES S.A.S. (route de l'orme des merisiers; Immeuble Discovery—Zone Technologique; 91190 SAINT AUBIN, FRANCE), under catalog number 4456740, and
- the RNA Internal Control, which is commercialized by QIAGEN® (QIAGEN® France S.A.S.; 3, avenue du Canada; LP 809; 91974 COURTABOEUF CEDEX; FRANCE) under catalog number 211492.

Alternatively to the IECR, the internal control of RNA extraction and/or purification can be performed by detecting that a human gene is still present after said extraction and/or purification step. Examples of suitable human genes are known in the art and include constitutive genes, such as the human albumin (ALB) gene or the human TATA Box binding protein (TBP). Hence, the means of the application may further comprise at least probe, more particularly at least one (real-time) probe and at least one primer pair, which specifically detect a human gene, such as the human albumin (ALB) gene or the human TATA Box binding protein (TBP); cf. example 2 below.

Said sample of biological fluid may e.g., be a sample of lower respiratory tract fluid, such as a sample of bronchoalveolar lavage fluid, or induced sputum, or a sample of upper respiratory tract fluid, such as a sample of sputum, nasopharyngeal aspirate, oral wash or nasal swab.

Said human patient can be HIV-positive or is HIV-negative, more particularly HIV-negative. More particularly, said human patient is HIV-negative and immunocompromised. Advantageously, the means of the application are reliable with HIV-negative human patients, whereas the *P. jirovecii* charge of HIV-negative human patients is lower than that of HIV-positive human patients.

Advantageously, said human patient is a human patient, more particularly a HIV-negative human patient, who is receiving, has received or will receive an immunosuppressive treatment, more particularly an immunosuppressor agent or drug, more particularly chemotherapy, an antirejection drug or steroids. For example, said human patient is a human patient, more particularly a HIV-negative human patient, who is receiving, has received or will receive a graft of organ(s) and/or tissue(s) (e.g., bone marrow, heart, kidney, liver organ(s), and/or tissue(s) thereof). Said immunosuppressive treatment, immunosuppressor agent or drug, antirejection drug may e.g., be intended to prevent and/or palliate the rejection of said transplanted organ(s) and tissue(s) and/or graft-versus-host disease. For example, said human patient is a human patient, more particularly a HIV-negative patient, who has an autoimmune disease and/or an inflammatory disease.

Advantageously, said human patient is a human patient, more particularly a HIV-negative human patient, who has a haematological malignancy and/or a solid malignancy. Advantageously, said human patient is a human patient, more particularly a HIV-negative human patient, who is a preterm baby (more particularly a preterm baby, who is born at less than 37 weeks gestational age), a newborn or neonate (more particularly of 1-day old to less than 4-week old) or an infant (more particularly of 4-week old to less than 1-year old). More particularly, said human patient is a human patient, more particularly a HIV-negative human patient, who is a preterm baby (more particularly a preterm baby, who is born at less than 37 weeks gestational age), a newborn or neonate (more particularly of 1-day old to less than 4-week old).

Advantageously, said quantification of RNA transcripts is performed by (cDNA) reverse-transcription and PCR amplification (for each of said two *P. jirovecii* mitochondrial genes).

More particularly, said (cDNA) reverse-transcription and PCR amplification can be performed (as a one-step RT-PCR reaction, i.e.,) in the same tube (for each of said two *P. jirovecii* mitochondrial genes).

Hence, the (cDNA) reverse-transcription and PCR amplification of the RNA transcripts of said first *P. jirovecii* mitochondrial gene can be performed in the same tube, and the reverse-transcription and PCR amplification of the RNA transcripts of said second *P. jirovecii* mitochondrial gene can be performed in the same tube.

The (cDNA) reverse-transcription and PCR amplification of the RNA transcripts of said first *P. jirovecii* mitochondrial gene can be performed in a tube different from, or in the same tube as, the tube in which the (cDNA) reverse-transcription and PCR amplification of the RNA transcripts of second first *P. jirovecii* mitochondrial gene is performed.

Said PCR advantageously is real-time PCR.

Advantageously, said PCR is a quantitative PCR, more particularly a quantitative real-time PCR, more particularly a quantitative real-time RT-PCR, more particularly a one-step quantitative real-time RT-PCR.

Said threshold value can e.g., be in the 1.00-2.00 range, more particularly in the 1.00-1.80 range, more particularly in the 1.20-1.70 range, more particularly in the 1.27-1.66 range, more particularly is of 1.50.

For example, said ratio calculation is performed using the equation $$R = E(\text{CYTb})^{-Cq(CYTb)}/E(\text{mtrDNA})^{-Cq(mtrDNA)}$$

wherein
- R is said ratio,
- CYTB is the cDNA reverse-transcript of the RNA transcripts of said *P. jirovecii* gene, the sequence of which codes for the Cytb protein,
- mtrDNA is the cDNA reverse-transcript of the RNA transcripts of said *P. jirovecii* gene, the sequence of which transcribes into a *P. jirovecii* ribosomal RNA,
- E is the value of the PCR efficiency of one amplification cycle in the exponential phase for the indicated cDNA, and Cq is the value of the PCR quantification cycle for the indicated cDNA.

Advantageously, said ratio is the fold change of the value of quantification of the RNA transcripts of said first *P. jirovecii* mitochondrial gene compared to said second *P. jirovecii* mitochondrial gene.

These features may notably apply when said first *P. jirovecii* mitochondrial gene is the *P. jirovecii* gene, the sequence of which codes for the Cytb protein, and when said second *P. jirovecii* mitochondrial gene is a *P. jirovecii* gene, the sequence of which transcribes into a *P. jirovecii* ribosomal RNA, such as the mtLSU gene or the mtSSU gene, more particularly the mtLSU gene.

Of course, when said first *P. jirovecii* mitochondrial gene is the mtLSU gene and said second *P. jirovecii* mitochondrial gene is the *P. jirovecii* gene, the sequence of which codes for the Cytb protein, said threshold value can e.g., be in the 1/2.00-1/1.00 range, more particularly in the 1/1.80-1/1.00 range, more particularly in the 1/1.70-1/1.20 range, more particularly in the 1/1.66-1/1.27 range, more particularly is of 1/1.50.

Said threshold value can e.g., be in the 2.7-3.3 range, more particularly in the 3.1-3.3 range, for example 3.2.

For example, the ratio calculation is performed using the equation $$R = E(\text{mtSSU})^{-Cq(mtSSU)} / E(\text{mtLSU})^{-Cq(mtLSU)}$$

wherein

R is said ratio, mtSSU is the cDNA reverse-transcript of the RNA transcripts of said mitochondrial *P. jirovecii* mtSSU gene, mtLSU is the cDNA reverse-transcript of the RNA transcripts of said mitochondrial *P. jirovecii* mtLSU gene, E is the value of the PCR efficiency of one amplification cycle in the exponential phase for the indicated cDNA, and Cq is the value of the PCR quantification cycle for the indicated cDNA.

These features may notably apply when said first *P. jirovecii* mitochondrial gene is the mtSSU gene, and wherein said second *P. jirovecii* mitochondrial gene is the mtLSU gene. Of course, when said first *P. jirovecii* mitochondrial gene is the mtLSU gene and said second *P. jirovecii* mitochondrial gene is the mtSSU gene, said threshold value can e.g., be in the 1/3.3-1/2.7 range, more particularly in the 1/3.3-1/3.1 range, for example 1/3.2.

In a method of the application, the quantification of the respective RNA transcripts may be achieved by any means that the person of ordinary skill in the art may found appropriate. Such means include hybridization- or sequence-based means, as well as any means that enable to quantify a transcriptome, such as e.g., the RNA-Seq method (cf. Wang et al. 2009). The application provides a DNA library as well as computer means, which are suitable for implementation of the RNA-Seq method (cf. below).

In a method of the application, the quantification of the respective RNA transcripts may comprise:

the cDNA reverse transcription of the RNA transcripts of said first *P. jirovecii* mitochondrial gene (using a reverse transcriptase) to obtain first cDNA reverse-transcripts, and the PCR amplification of a first cDNA target from said first cDNA reverse-transcripts (using a polymerase and) using a first primer pair to obtain first amplicons (first cDNA or DNA nucleic acids), and the cDNA reverse transcription of the RNA transcripts of said second *P. jirovecii* mitochondrial gene (using a reverse transcriptase and) to obtain second cDNA reverse-transcripts, and the PCR amplification of a second cDNA target from said second cDNA reverse-transcripts (using a polymerase and) using a second primer pair to obtain second amplicons (second cDNA or DNA nucleic acids), wherein said method further comprises the quantification of (the number of or the concentration of) said first amplicons and of (the number of or the concentration of) said second amplicons, wherein the value of quantification of (e.g., the number of or the concentration of) said first amplicons is the value of quantification of (e.g., the number of or the concentration of) the RNA transcripts of said first *P. jirovecii* mitochondrial gene, and the value of quantification of (e.g., the number of or the concentration of) said second amplicons is the value of quantification of (e.g., the number of or the concentration of) the RNA transcripts of said second *P. jirovecii* mitochondrial gene.

When said first *P. jirovecii* mitochondrial gene is the *P. jirovecii* gene, the sequence of which codes for the Cytb protein, said first cDNA target advantageously consists of 100-120 nucleotides (more particularly of 100-110 nucleotides, more particularly of 102-108 nucleotides, more particularly of 104-106 nucleotides, more particularly of 105 nucleotides), and comprises or is the sequence of SEQ ID NO: 30, or a cDNA sequence, which is of the same length as SEQ ID NO: 30 and which is at least 95% (more particularly at least 96%, at least 97%, at least 98% or at least 99%) identical to SEQ ID NO: 30.

When said first *P. jirovecii* mitochondrial gene is the mtSSU gene, said first cDNA target advantageously consists of 60-110 nucleotides and comprises or is the sequence of SEQ ID NO: 15 or of SEQ ID NO: 20 or of SEQ ID NO: 25, or a cDNA sequence, which is of the same length as SEQ ID NO: 15 or as SEQ ID NO: 20 or as SEQ ID NO: 25, and which is at least 95% identical to SEQ ID NO: 15 or SEQ ID NO: 20 or SEQ ID NO: 25, respectively.

When said second *P. jirovecii* mitochondrial gene is mtLSU gene, said second cDNA target advantageously consists of 115-125 nucleotides and comprises or is the sequence of SEQ ID NO: 10, or a cDNA sequence, which is of the same length as SEQ ID NO: 10 and which is at least 95% identical to SEQ ID NO: 10.

When said second *P. jirovecii* mitochondrial gene is the *P. jirovecii* gene is the mtSSU gene, said second cDNA target advantageously consists of 60-110 nucleotides and comprises or is the sequence of SEQ ID NO: 15 or of SEQ ID NO: 20 or of SEQ ID NO: 25, or a cDNA sequence, which is of the same length as SEQ ID NO: 15 or as SEQ ID NO: 20 or as SEQ ID NO: 25, and which is at least 95% identical to SEQ ID NO: 15 or SEQ ID NO: 20 or SEQ ID NO: 25, respectively.

In a method of the application, the quantification of the respective RNA transcripts comprises:

the cDNA reverse transcription of a first RNA target contained in the RNA transcripts of said first *P. jirovecii* mitochondrial gene (using a reverse transcriptase and) using a first primer pair to obtain first cDNA reverse-transcripts, and the PCR amplification of said first cDNA reverse-transcripts (using a polymerase and) using the same first primer pair to obtain first amplicons, and the cDNA reverse transcription of a second RNA target from the RNA transcripts of said second *P. jirovecii* mitochondrial gene (using a reverse transcriptase and) using a second primer pair to obtain second cDNA reverse-transcripts, and the PCR amplification of said second cDNA reverse-transcripts (using a polymerase and) using the same second primer pair to obtain second amplicons, wherein said method further comprises the quantification of (the number of or the concentration of) said first amplicons and of (the number of or the concentration of) said second amplicons, wherein the value of quantification of (e.g., the number of or the concentration of) said first amplicons is the value of quantification of (e.g., the number of or the concentration of) the RNA transcripts of said first *P. jirovecii* mitochondrial gene, and the value of quantification of (e.g., the number of or the concentration of) said second amplicons is the value of quantification of (e.g., the number of or the concentration of) the RNA transcripts of said second *P. jirovecii* mitochondrial gene.

When said first *P. jirovecii* mitochondrial gene is the *P. jirovecii* gene, the sequence of which codes for the Cytb protein, said first RNA target may advantageously consist of 100-120 nucleotides (more particularly of 100-110 nucleotides, more particularly of 102-108 nucleotides, more particularly of 104-106 nucleotides, more particularly of 105 nucleotides), and comprises or is the sequence of SEQ ID NO: 29, or
a RNA sequence, which is of the same length as SEQ ID NO: 29 and which is at least 95% (more particularly at least 96%, at least 97%, at least 98% or at least 99%) identical to SEQ ID NO: 29.

When said first *P. jirovecii* mitochondrial gene is the mtSSU gene, said first RNA target advantageously consists of 60-110 nucleotides and comprises or is the sequence of SEQ ID NO: 14 or of SEQ ID NO: 19 or of SEQ ID NO: 24, or
a RNA sequence, which is of the same length as SEQ ID NO: 14 or as SEQ ID NO: 19 or as SEQ ID NO: 24, and which is at least 95% identical to SEQ ID NO: 14 or SEQ ID NO: 19 or SEQ ID NO: 24, respectively.

When said second *P. jirovecii* mitochondrial gene is the mtLSU gene, said second RNA target advantageously consists of 115-125 nucleotides and comprises or is the sequence of SEQ ID NO: 9, or
a RNA sequence, which is of the same length as SEQ ID NO: 9 and which is at least 95% identical to SEQ ID NO: 9.

When said second *P. jirovecii* mitochondrial gene is the mtSSU gene, said second RNA target advantageously consists of 60-110 nucleotides and comprises or is the sequence of SEQ ID NO: 14 or of SEQ ID NO: 19 or of SEQ ID NO: 24, or
a RNA sequence, which is of the same length as SEQ ID NO: 14 or as SEQ ID NO: 19 or as SEQ ID NO: 24, and which is at least 95% identical to SEQ ID NO: 14 or SEQ ID NO: 19 or SEQ ID NO: 24, respectively.

In the application, and in accordance with the understanding of the person of average skill in the art, the phrase "reverse polymerase" refers to a RNA-dependent DNA polymerase, and the phrase "polymerase" refers to a "DNA-dependent DNA polymerase".

The term "nucleotide" encompasses naturally-occurring nucleotides, as well as no-naturally-occurring nucleotides, such as Locked Nucleic Acid (LNA™) nucleotides. A LNA™ nucleotide is understood in accordance with its ordinary meaning in the field, i.e., a nucleotide in which the ribose or deoxyribose ring is "locked" by a methylene bridge connecting the 2'-O atom and the 4'-C atom. The term "nucleotide" encompasses more particularly naturally-occurring nucleotides (nucleotides A, G, T and C for DNA molecules; nucleotides A, G, U and C for RNA molecules).

In other words, when said first or second *P. jirovecii* mitochondrial gene is the *P. jirovecii* gene, the sequence of which codes for the Cytb protein, said first or second primer pair is a primer pair which anneals to the cDNA reverse transcripts of the RNA transcripts of said first or second *P. jirovecii* mitochondrial gene (or to the RNA transcripts of said first or second *P. jirovecii* mitochondrial gene as well as to the cDNA reverse transcripts thereof) respectively, to produce a (cDNA or DNA) amplicon (or to produce cDNA reverse-transcripts as well as the (cDNA or DNA) amplicon thereof), which is of 100-120 nucleotide-long (more particularly of 100-110 nucleotide-long, more particularly of 102-108 nucleotide-long, more particularly of 104-106 nucleotide-long, more particularly of 105 nucleotide-long), and which comprises or is the sequence of SEQ ID NO: 30, or
a cDNA sequence, which is of the same length as SEQ ID NO: 30 and which is at least 95% (more particularly at least 96%, at least 97%, at least 98% or at least 99%) identical to SEQ ID NO: 30.

The nucleotide sequence of each primer of said first or second primer pair may independently consist of 15-30 nucleotides (more particularly of 18-28 nucleotides, more particularly of 19-27 nucleotides, more particularly of 20-26 nucleotides, more particularly of 20 nucleotides).

For example, said first or second primer pair is the primer pair of SEQ ID NO: 31 and SEQ ID NO: 32. Alternatively, said first or second primer pair is the primer pair of SEQ ID NO: 60 and SEQ ID NO: 32.

Said first or second cDNA or RNA target may be a *P. jirovecii* mtLSU target.

For example, when said first or second *P. jirovecii* mitochondrial gene is the mtLSU gene, said first or second (mtLSU) cDNA target may consist of 115-125 nucleotides (more particularly of 117-124 nucleotides, more particularly of 119-123 nucleotides, more particularly of 121 nucleotides), and comprises or is the sequence of SEQ ID NO: 10, or
a cDNA sequence, which is of the same length as SEQ ID NO: 10 and which is at least 95% (more particularly at least 96%, at least 97%, at least 98% or at least 99%) identical to SEQ ID NO: 10.

For example, said first or second (mtLSU) RNA target may consist of 115-125 nucleotides (more particularly of 117-124 nucleotides, more particularly of 119-123 nucleotides, more particularly of 121 nucleotides), and comprises or is the sequence of SEQ ID NO: 9, or
a RNA sequence, which is of the same length as SEQ ID NO: 9 and which is at least 95% (more particularly at least 96%, at least 97%, at least 98% or at least 99%) identical to SEQ ID NO: 9.

In other words, said first or second primer pair may e.g., be a (mtLSU) primer pair, which anneals to the cDNA reverse-transcripts of the RNA transcripts of the *P. jirovecii* mtLSU gene (or to the RNA transcripts of the *P. jirovecii* mtLSU gene as well as to the cDNA reverse- transcripts thereof) to produce a (cDNA or DNA) amplicon (or to produce cDNA reverse-transcripts as well as the (cDNA or DNA) amplicon thereof), which is of 115-125 nucleotides (more particularly of 117-124 nucleotides, more particularly of 119-123 nucleotides, more particularly of 121 nucleotides), and which comprises or is the sequence of SEQ ID NO: 10, or
a cDNA sequence, which is of the same length as SEQ ID NO: 10 and which is at least 95% (more particularly at least 96%, at least 97%, at least 98% or at least 99%) identical to SEQ ID NO: 10.

The nucleotide sequence of each (mtLSU) primer of first or said second primer pair may independently consist of 15-30 nucleotides (more particularly of 18-28 nucleotides, more particularly of 19-27 nucleotides, more particularly of 20-26 nucleotides, more particularly of 26 nucleotides).

For example, said first or second primer pair is the (mtLSU) primer pair of SEQ ID NO: 11 and SEQ ID NO: 12.

Alternatively, said first or second cDNA or RNA target may e.g., be a P. jirovecii mtSSU target.

For example, said first or second (mtSSU) cDNA target may consist of 60-110 nucleotides (more particularly of 76-92 nucleotides, more particularly of 76, 82 or 92 nucleotides, more particularly of 82 nucleotides), and comprises or is the sequence of SEQ ID NO: 15, or
a cDNA sequence, which is of the same length as SEQ ID NO: 15 and which is at least 95% (more particularly at least 96%, at least 97%, at least 98% or at least 99%) identical to SEQ ID NO: 15.

For example, said first or second (mtSSU) RNA target may consist of 60-110 nucleotides (more particularly of 76-92 nucleotides, more particularly of 76, 82 or 92 nucleotides, more particularly of 82 nucleotides), and comprises or is the sequence of SEQ ID NO: 14, or
a RNA sequence, which is of the same length as SEQ ID NO: 14 and which is at least 95% (more particularly at least 96%, at least 97%, at least 98% or at least 99%) identical to SEQ ID NO: 14.

In other words, said first or second primer pair may alternatively be a (mtSSU) primer pair, which anneals to the cDNA reverse transcripts of the RNA transcripts of the P. jirovecii mtSSU gene (or to the RNA transcripts of the P. jirovecii mtSSU gene as well as to the cDNA reverse transcripts thereof) to produce a (cDNA or DNA) amplicon (or to produce cDNA reverse-transcripts as well as the (cDNA or DNA) amplicon thereof), which is of 60-110 nucleotides (more particularly of 76-92 nucleotides, more particularly of 76, 82 or 92 nucleotides, more particularly of 82 nucleotides), and comprises or is the sequence of SEQ ID NO: 15, or
a cDNA sequence, which is of the same length as SEQ ID NO: 15 and which is at least 95% (more particularly at least 96%, at least 97%, at least 98% or at least 99%) identical to SEQ ID NO: 15.

The nucleotide sequence of each (mtSSU) primer of said first or second primer pair may independently consist of 15-30 nucleotides (more particularly of 18-28 nucleotides, more particularly of 19-27 nucleotides, more particularly of 20-26 nucleotides, more particularly of 20-23 nucleotides).

For example, said first or second primer pair is the (mtSSU) primer pair of SEQ ID NO: 16 and SEQ ID NO: 17.

For example, said first or second (mtSSU) cDNA target may consist of 60-110 nucleotides (more particularly of 76-92 nucleotides, more particularly of 76, 82 or 92 nucleotides, more particularly of 92 nucleotides), and comprises or is the sequence of SEQ ID NO: 20, or
a cDNA sequence, which is of the same length as SEQ ID NO: 20 and which is at least 95% (more particularly at least 96%, at least 97%, at least 98% or at least 99%) identical to SEQ ID NO: 20.

For example, said first or second (mtSSU) RNA target may consist of 60-110 nucleotides (more particularly of 76-92 nucleotides, more particularly of 76, 82 or 92 nucleotides, more particularly of 92 nucleotides), and comprises or is the sequence of SEQ ID NO: 19, or
a RNA sequence, which is of the same length as SEQ ID NO: 19 and which is at least 95% (more particularly at least 96%, at least 97%, at least 98% or at least 99%) identical to SEQ ID NO: 19.

In other words, said first or second primer pair may alternatively be a (mtSSU) primer pair, which anneals to the cDNA reverse transcripts of the RNA transcripts of the P. jirovecii mtSSU gene (or to the RNA transcripts of the P. jirovecii mtSSU gene as well as to the cDNA reverse transcripts thereof) to produce a (cDNA or DNA) amplicon (or to produce cDNA reverse-transcripts as well as the (cDNA or DNA) amplicon thereof), which is of 60-110 nucleotides (more particularly of 76-92 nucleotides, more particularly of 76, 82 or 92 nucleotides, more particularly of 92 nucleotides), and comprises or is the sequence of SEQ ID NO: 20, or
a cDNA sequence, which is of the same length as SEQ ID NO: 20 and which is at least 95% (more particularly at least 96%, at least 97%, at least 98% or at least 99%) identical to SEQ ID NO: 20.

The nucleotide sequence of each (mtSSU) primer of said first or second primer pair may independently consist of 15-30 nucleotides (more particularly of 18-28 nucleotides, more particularly of 19-27 nucleotides, more particularly of 20-26 nucleotides, more particularly of 20-23 nucleotides).

For example, said first or second primer pair is the (mtSSU) primer pair of SEQ ID NO: 21 and SEQ ID NO: 22.

For example, said first or second (mtSSU) cDNA target may consist of 60-110 nucleotides (more particularly of 76-92 nucleotides, more particularly of 76, 82 or 92 nucleotides, more particularly of 76 nucleotides), and comprises or is the sequence of SEQ ID NO: 25, or
a cDNA sequence, which is of the same length as SEQ ID NO: 25 and which is at least 95% (more particularly at least 96%, at least 97%, at least 98% or at least 99%) identical to SEQ ID NO: 25.

For example, said first or second (mtSSU) RNA target may consist of 60-110 nucleotides (more particularly of 76-92 nucleotides, more particularly of 76, 82 or 92 nucleotides, more particularly of 76 nucleotides), and comprises or is the sequence of SEQ ID NO: 24, or
a RNA sequence, which is of the same length as SEQ ID NO: 24 and which is at least 95% (more particularly at least 96%, at least 97%, at least 98% or at least 99%) identical to SEQ ID NO: 24.

In other words, said first or second primer pair may alternatively be a (mtSSU) primer pair, which anneals to the cDNA reverse transcripts of the RNA transcripts of the P. jirovecii mtSSU gene (or to the RNA transcripts of the P. jirovecii mtSSU gene as well as to the cDNA reverse transcripts thereof) to produce a (cDNA or DNA) amplicon (or to produce cDNA reverse-transcripts as well as the (cDNA or DNA) amplicon thereof), which is of 60-110 nucleotides (more particularly of 76-92 nucleotides, more particularly of 76, 82 or 92 nucleotides, more particularly of 76 nucleotides), and comprises or is the sequence of SEQ ID NO: 25, or a cDNA sequence, which is of the same length as SEQ ID NO: 25 and which is at least 95% (more particularly at least 96%, at least 97%, at least 98% or at least 99%) identical to SEQ ID NO: 25.

The nucleotide sequence of each (mtSSU) primer of said first or second primer pair may independently consist of 15-30 nucleotides (more particularly of 18-28 nucleotides, more particularly of 19-27 nucleotides, more particularly of 20-26 nucleotides, more particularly of 20-23 nucleotides).

For example, said first or second primer pair is the (mtSSU) primer pair of SEQ ID NO: 26 and SEQ ID NO: 27.

Advantageously, the Tm of said first primer pair does not differ by more than 5° C. (more particularly by more than 4° C., more particularly by more than 3° C., more particularly by more than 2° C., more particularly by more than 1° C.) from the Tm of said second primer pair. The Tm of said first primer pair may be identical to the Tm of said second primer pair.

Alternatively or complementarily, the Tm of said first primer pair and the Tm of said second primer pair may both be of 53° C. or above. More particularly, said first primer pair and said second primer pair may both have a Tm in the 53-65° C. range (more particularly in the 56-64° C. range, more particularly in the 57-63° C. range, more particularly in the 58-63° C. range, more particularly in the 59-62° C. range, more particularly in the 59-61° C. range). For example, said first primer pair and said second primer pair may both have a Tm of 60° C.

For example, the Tm of said first primer pair and the Tm of said second primer pair are both in the 58-63° C. range and do not differ by more than 5° C. from each other.

Any PCR or RT-PCR conditions that the skilled person finds appropriate may be implemented.

For example, the PCR amplification (for each of said first and second *P. jirovecii* mitochondrial genes) comprises:
polymerase activation at 95° C. for 2-10 min, and
45-50 cycles of 95° C. for 15-30 seconds and 60° C. for 30-60 seconds.

For example, the PCR amplification (for each of said first and second *P. jirovecii* mitochondrial genes) comprises:
polymerase activation at 95° C. for 2 min, and
45 cycles of 95° C. for 15 seconds and 60° C. for 30 seconds.

For example, the RT-PCR amplification comprises (for each of said first and second *P. jirovecii* mitochondrial genes):
reverse transcription at 42-61° C., preferably 50° C. for 2-15 min,
polymerase activation at 95° C. for 2 min, and
45 cycles of 95° C. for 15 seconds and 60° C. for 30 seconds.

For example, the RT-PCR amplification comprises (for each of said first and second *P. jirovecii* mitochondrial genes):
reverse transcription at 50° C. for 2 min,
polymerase activation at 95° C. for 2 min, and
45 cycles of 95° C. for 15 seconds and 60° C. for 30 seconds.

The quantification of the RNA transcripts of said first and/or (more particularly, and) said second *P. jirovecii* mitochondrial gene can be performed using probes, more particularly using at least one first probe, which hybridizes to the cDNA reverse-transcript of said first *P. jirovecii* mitochondrial gene (CYTB), and/or (more particularly, and) at least one second probe, which hybridizes to the cDNA reverse-transcript of said second *P. jirovecii* mitochondrial gene (mtLSU or mtSSU, more particularly mtLSU), or more particularly using at least one first probe, which hybridizes to the cDNA reverse-transcript of said first *P. jirovecii* mitochondrial gene (mtSSU), and/or (more particularly, and) at least one second probe, which hybridizes to the cDNA reverse-transcript of said second *P. jirovecii* mitochondrial gene (mtLSU).

Each of said first and second probes may independently consist of 17-37 nucleotides.

More particularly, the quantification of the RNA transcripts of said first *P. jirovecii* mitochondrial gene can be performed using at least one first probe, which hybridizes to said first cDNA target (or said first amplicons), without hybridizing to said second cDNA target (or to said second amplicons).

More particularly, the quantification of the RNA transcripts of said first *P. jirovecii* mitochondrial gene can be performed using at least one first probe, which specifically hybridizes to said first cDNA target (or to said first amplicons).

More particularly, the quantification of the RNA transcripts of said second *P. jirovecii* mitochondrial gene can be performed using at least one second probe, which hybridizes to said second cDNA target (or said second amplicons), without hybridizing to said first cDNA target (or to said first amplicons).

More particularly, the quantification of the RNA transcripts of said second *P. jirovecii* mitochondrial gene can be performed using at least one second probe, which specifically hybridizes to said second cDNA target (or to said second amplicons).

The quantification of the RNA transcripts of said first *P. jirovecii* mitochondrial gene may e.g., be performed using (at least one) first probe, which hybridizes to the cDNA reverse-transcript of said first *P. jirovecii* mitochondrial gene.

For example, when said first *P. jirovecii* mitochondrial gene is the *P. jirovecii* gene, the sequence of which codes for the Cytb protein, said first probe may hybridize to the sequence of SEQ ID NO: 3 or the complementary sequence thereof, more particularly to the sequence of SEQ ID NO: 30 or the complementary sequence thereof, without hybridizing to any of SEQ ID NO: 1 (*P. jirovecii* mtLSU gene) and the sequence complementary to SEQ ID NO: 1, or to any of SEQ ID NO: 2 (*P. jirovecii* mtSSU gene) and the sequence complementary to SEQ ID NO: 2, more particularly to any of SEQ ID NO: 1, the sequence complementary to SEQ ID NO: 1, SEQ ID NO: 2 and the sequence complementary to SEQ ID NO: 2. Said first probe may also not hybridize to human DNA or RNA. Advantageously, said first probe specifically hybridizes to the sequence of SEQ ID NO: 3 or the complementary sequence thereof, more particularly to the sequence of SEQ ID NO: 30 or the complementary sequence thereof.

The sequence of said first probe may e.g., consist of or comprise a hybridization portion, which is or acts as the hybridization portion of the probe, i.e., which is or acts as the DNA or RNA portion, which confers to the first probe the capacity to hybridize to the cDNA reverse-transcript of said first *P. jirovecii* mitochondrial gene.

Said hybridization portion may e.g., be a DNA or RNA sequence of 19-30 nucleotides (more particularly of 20-24 nucleotides, more particularly of 22 nucleotides), which hybridizes to the sequence of SEQ ID NO: 3 or the sequence complementary to SEQ ID NO: 3, more particularly to the sequence of SEQ ID NO: 30 or the sequence complementary to SEQ ID NO: 30, without hybridizing to any of SEQ ID NO: 1 and the sequence complementary to SEQ ID NO: 1, or to any of SEQ ID NO: 2 and the sequence complementary to SEQ ID NO: 2, more particularly to any of SEQ ID NO: 1, the sequence complementary to SEQ ID NO: 1, SEQ ID NO: 2 and the sequence complementary to SEQ ID NO: 2. Said hybridization portion of said first probe may also not hybridize to human DNA or RNA. Said hybridization portion of said first probe may specifically hybridize to the sequence of SEQ ID NO: 3 or to the complementary sequence thereof, more particularly to the sequence of SEQ ID NO: 30 or to the complementary sequence thereof. For example, the hybridization portion of said first probe is the (22 nucleotide-long) sequence of SEQ ID NO: 33 or the complementary sequence thereof, or a LNA-counterpart thereof, such as the (22 nucleotide-long) sequence of SEQ ID NO: 58 or the complementary sequence thereof (SEQ ID NO: 59; cf. example 3 below).

The sequence of said first probe may consist of said hybridization portion.

Alternatively, the sequence of said first probe may comprise other DNA or RNA sequence(s) in addition to said hybridization portion, e.g., other DNA or RNA sequence(s) linked to the 5' and/or 3' terminal end(s) of said hybridization portion. This(these) other DNA or RNA sequence(s) should not (significantly) reduce the hybridization specificity of said hybridization portion. Said other DNA or RNA sequence(s) may e.g., be beacon arm(s), more particularly a 5' beacon arm and a 3' beacon arm, which impart a hairpin-configuration to said first probe when unhybridized (e.g., the 3' beacon arm is complementary to the 5' beacon arm). The total length of said first probe advantageously is of 28-32 nucleotides, or of 27-31 nucleotides, or of 26-30 nucleotides, or of 25-29 nucleotides.

Said first probe may comprise (e.g., be covalently linked to) at least one fluorophore (e.g., 6-carboxyfluorescein, or tetrachlorofluorescein) and/or at least one quencher (e.g., a carboxytetramethylrhodamine fluorescent dye (e.g., TAMRA®), the Black Hole Quencher®-0, the Black Hole Quencher®-1, the Black Hole Quencher®-2, the Black Hole Quencher®-3, or the Minor Groove Binder® quencher).

Said first probe may e.g., be a Locked Nucleic Acid (LNA) probe.

Said first probe may e.g., be a DNA or RNA probe. For example, said first probe may be a TAQMAN® probe, i.e., a probe, wherein a fluorophore is covalently attached to its 5'-end and a quencher is covalently attached to its at the 3'-end (e.g., TAMRA® or BHQ®-1). A TAQMAN® probe is degraded by the 5'-3' exonuclease activity of the PCR polymerase, thereby releasing the fluorophore from it (and from the proximity of the quencher).

Alternatively, said first probe may be a beacon probe, i.e., a probe which in addition to said hybridization portion, comprises a beacon arm linked to the 5' terminal end and a beacon arm linked to the 3' terminal end (which impart a hairpin-configuration to said first probe when unhybridized), and which carries a fluorophore covalently linked to one of said two beacon arms, and a quencher linked to the other of said two beacon arms.

Alternatively, said first probe may be a SCORPION® probe (i.e., a probe, which is linked to a fluorophore at one of its ends and which is linked at the other end to a primer via a PCR blocker).

The quantification may also be performed using at least two of said first probes (i.e., two different first probes) each comprising at least one fluorophore (e.g., as LIGHTCYCLER® hybridization probes).

The Tm of the probe may be 4-10° C. higher than the Tm of the primer pair.

For example, when said first P. jirovecii mitochondrial gene is the mtSSU gene, said first probe may hybridize to
 the P. jirovecii mtSSU gene, which is of SEQ ID NO: 2 or to the sequence complementary to SEQ ID NO: 2, more particularly to the sequence of SEQ ID NO: 15 (a P. jirovecii mtLSU target) or to the sequence complementary to SEQ ID NO: 15, and/or
 to the sequence of SEQ ID NO: 20 (another P. jirovecii mtLSU target) or to the sequence complementary to SEQ ID NO: 20, and/or
 to the sequence of SEQ ID NO: 25 (still another P. jirovecii mtLSU target) or to the sequence complementary to SEQ ID NO: 25.

More particularly, said first probe may hybridize to the sequence of SEQ ID NO: 2 or the complementary sequence thereof, more particularly to at least one of the sequences of SEQ ID NO: 15, 20, 25 and the complementary sequences thereof, without hybridizing to any of SEQ ID NO: 3 (P. jirovecii CYTB gene) and the sequence complementary to SEQ ID NO: 3, or to any of SEQ ID NO: 1 (P. jirovecii mtLSU gene) and the sequence complementary to SEQ ID NO: 1, more particularly without hybridizing to any of SEQ ID NO: 3, the sequence complementary to SEQ ID NO: 3, SEQ ID NO: 1 and the sequence complementary to SEQ ID NO: 1.

Said first probe may also not hybridize to human DNA or RNA.

Advantageously, said first probe specifically hybridizes to the sequence of SEQ ID NO: 2 or the complementary sequence thereof, more particularly to at least one of the sequences of SEQ ID NO: 15, 20, 25 and the complementary sequences thereof.

The sequence of said first probe may e.g., consist of or comprise a hybridization portion, which is or acts as the hybridization portion of the probe, i.e., which is or acts as the DNA portion, which confers to the first probe the capacity to hybridize to the cDNA reverse-transcript of said first P. jirovecii mitochondrial gene.

Said hybridization portion may e.g., be a DNA sequence of 23-29 nucleotides (more particularly of 25-27 nucleotides), which hybridizes to the sequence of SEQ ID NO: 2 or the sequence complementary to SEQ ID NO: 2, more particularly to at least one of the sequences of SEQ ID NO: 15, 20, 25 and the sequences complementary to SEQ ID NO: 10, 20, 25, without hybridizing to any of SEQ ID NO: 3 and the sequence complementary to SEQ ID NO: 3, or to any of SEQ ID NO: 1 and the sequence complementary to SEQ ID NO: 1, more particularly without hybridizing to any of SEQ ID NO: 3, the sequence complementary to SEQ ID NO: 3, SEQ ID NO: 1 and the sequence complementary to SEQ ID NO: 1.

Said hybridization portion of said first probe may also not hybridize to human DNA or RNA. Said hybridization portion of said first probe may specifically hybridize to the sequence of SEQ ID NO: 2 or to the complementary sequence thereof, more particularly to at least one of the sequences of SEQ ID NO: 15, 20, 25 and the complementary sequences thereof. For example, the hybridization portion of said first probe is the (25 or 27 nucleotide-long) sequence of SEQ ID NO: 18, 23 or 28 or the complementary sequence thereof.

The sequence of said first probe may consist of said hybridization portion.

Alternatively, the sequence of said first probe may comprise other DNA sequence(s) in addition to said hybridization portion, e.g., other DNA sequence(s) linked to the 5' and/or 3' terminal end(s) of said hybridization portion. This(these) other DNA sequence(s) should not (significantly) reduce the hybridization specificity of said hybridization portion. Said other DNA sequence(s) may e.g., be beacon arm(s), more particularly a 5' beacon arm and a 3' beacon arm, which impart a hairpin-configuration to said first probe when unhybridized (e.g., the 3' beacon arm is complementary to the 5' beacon arm). The total length of said first probe advantageously is of 31-37 nucleotides, or of 30-36 nucleotides, or of 29-36 nucleotides, or of 28-34 nucleotides.

Said first probe may comprise at least one fluorophore (e.g., 6-carboxyfluorescein, or tetrachlorofluorescein) and/or at least one quencher (e.g., a carboxytetramethylrhodamine fluorescent dye (e.g., TAMRA®), the Black Hole Quencher®-0, the Black Hole Quencher®-1, the Black Hole Quencher®-2, the Black Hole Quencher®-3, or the Minor Groove Binder® quencher).

Said first probe may be a TAQMAN® probe, i.e., a probe, wherein a fluorophore is covalently attached to its 5'-end and a quencher is covalently attached to its at the 3'-end (e.g., TAMRA® or BHQ®-1). A TAQMAN® probe is degraded by the 5'-3' exonuclease activity of the PCR polymerase, thereby releasing the fluorophore from it (and from the proximity of the quencher).

Alternatively, said first probe may be a beacon probe, i.e., a probe which in addition to said hybridization portion, comprises a beacon arm linked to the 5' terminal end and a beacon arm linked to the 3' terminal end (which impart a hairpin-configuration to said second probe when unhybridized), and which carries a fluorophore covalently linked to one of said two beacon arms, and a quencher linked to the other of said two beacon arms.

The Tm of the probe may be 4-10° C. higher than the Tm of the primer pair.

When said first P. jirovecii mitochondrial gene is the mtLSU gene, said first probe may hybridize to the P. jirovecii mtLSU gene, which is of SEQ ID NO: 1 or to the sequence complementary to SEQ ID NO: 1, more particularly to the sequence of SEQ ID NO: 10 (a P. jirovecii mtLSU target) or to the sequence complementary to SEQ ID NO: 10.

More particularly, said first probe may hybridize to the sequence of SEQ ID NO: 1 or the complementary sequence thereof, more particularly to the sequence of SEQ ID NO: 10 or the complementary sequence thereof, without hybridizing to any of SEQ ID NO: 3 (P. jirovecii CYTB gene) and the sequence complementary to SEQ ID NO: 3 or, to any of SEQ ID NO: 2 (P. jirovecii mtSSU gene) and the sequence complementary to SEQ ID NO: 2, more particularly without hybridizing to any of SEQ ID NO: 3, the sequence complementary to SEQ ID NO: 3, SEQ ID NO: 2 and the sequence complementary to SEQ ID NO: 2.

Said first probe may also not hybridize to human DNA or RNA.

Advantageously, said first probe specifically hybridizes to the sequence of SEQ ID NO: 1 or the complementary sequence thereof, more particularly to the sequence of SEQ ID NO: 10 or the complementary sequence thereof.

The sequence of said first probe may e.g., consist of or comprise a hybridization portion, which is or acts as the hybridization portion of the probe, i.e., which is or acts as the DNA or RNA portion, which confers to the first probe the capacity to hybridize to the cDNA reverse-transcript of said first P. jirovecii mitochondrial gene.

Said hybridization portion may e.g., be a DNA or RNA sequence of 17-21 nucleotides (more particularly of 19 nucleotides), which hybridizes to the sequence of SEQ ID NO: 1 or the sequence complementary to SEQ ID NO: 1, more particularly to the sequence of SEQ ID NO: 10 or the sequence complementary to SEQ ID NO: 10, without hybridizing to any of SEQ ID NO: 3 and the sequence complementary to SEQ ID NO: 3, or to any of SEQ ID NO: 2 and the sequence complementary to SEQ ID NO: 2, more particularly without hybridizing to any of SEQ ID NO: 3, the sequence complementary to SEQ ID NO: 3, SEQ ID NO: 2 and the sequence complementary to SEQ ID NO: 2.

Said hybridization portion of said first probe may also not hybridize to human DNA or RNA. Said hybridization portion of said first probe may specifically hybridize to the sequence of SEQ ID NO: 1 or to the complementary sequence thereof, more particularly to the sequence of SEQ ID NO: 10 or to the complementary sequence thereof. For example, the hybridization portion of said first probe is the (19 nucleotide-long) sequence of SEQ ID NO: 13 or the complementary sequence thereof.

The sequence of said first probe may consist of said hybridization portion.

Alternatively, the sequence of said first probe may comprise other DNA or RNA sequence(s) in addition to said hybridization portion, e.g., other DNA or RNA sequence(s) linked to the 5' and/or 3' terminal end(s) of said hybridization portion. This(these) other DNA or RNA sequence(s) should not (significantly) reduce the hybridization specificity of said hybridization portion. Said other DNA or RNA sequence(s) may e.g., be beacon arm(s), more particularly a 5' beacon arm and a 3' beacon arm, which impart a hairpin-configuration to said first probe when unhybridized (e.g., the 3' beacon arm is complementary to the 5' beacon arm). The total length of said first probe advantageously is of 25-29 nucleotides, or of 24-28 nucleotides, or of 23-27 nucleotides, or of 22-36 nucleotides.

Said first probe may comprise (e.g., be covalently linked to) at least one fluorophore (e.g., 6-carboxyfluorescein, or tetrachlorofluorescein) and/or at least one quencher (e.g., a carboxytetramethylrhodamine fluorescent dye (e.g., TAMRA®), the Black Hole Quencher®-0, the Black Hole Quencher®-1, the Black Hole Quencher®-2, the Black Hole Quencher®-3, or the Minor Groove Binder® quencher).

Said first probe may e.g., be a Locked Nucleic Acid (LNA) probe.

Said first probe may e.g., be a DNA or RNA probe.

For example, said first probe may be a TAQMAN® probe, i.e., a probe, wherein a fluorophore is covalently attached to its 5'-end and a quencher is covalently attached to its at the 3'-end (e.g., TAMRA® or BHQ®-1). A TAQMAN® probe is degraded by the 5'-3' exonuclease activity of the PCR polymerase, thereby releasing the fluorophore from it (and from the proximity of the quencher).

Alternatively, said first probe may be a beacon probe, i.e., a probe which in addition to said hybridization portion, comprises a beacon arm linked to the 5' terminal end and a beacon arm linked to the 3' terminal end (which impart a hairpin-configuration to said first probe when unhybridized), and which carries a fluorophore covalently linked to one of said two beacon arms, and a quencher linked to the other of said two beacon arms.

Alternatively, said first probe may be a SCORPION® probe (i.e., a probe, which is linked to a fluorophore at one of its ends and which is linked at the other end to a primer via a PCR blocker).

The quantification may also be performed using at least two of said first probes (i.e., two different first probes) each comprising at least one fluorophore (e.g., as LIGHTCY-CLER® hybridization probes).

The Tm of the probe may be 4-10° C. higher than the Tm of the primer pair.

The quantification of the RNA transcripts of said second *P. jirovecii* mitochondrial gene may e.g., be performed using (at least one) second probe, which hybridizes to the cDNA reverse-transcript of said second *P. jirovecii* mitochondrial gene.

When said second *P. jirovecii* mitochondrial gene is the mtLSU gene, said second probe may hybridize to the *P. jirovecii* mtLSU gene, which is of SEQ ID NO: 1 or to the sequence complementary to SEQ ID NO: 1, more particularly to the sequence of SEQ ID NO: 10 (a *P. jirovecii* mtLSU target) or to the sequence complementary to SEQ ID NO: 10. More particularly, said second probe may hybridize to the sequence of SEQ ID NO: 1 or the complementary sequence thereof, more particularly to the sequence of SEQ ID NO: 10 or the complementary sequence thereof, without hybridizing to any of SEQ ID NO: 3 (*P. jirovecii* CYTB gene) and the sequence complementary to SEQ ID NO: 3 or, to any of SEQ ID NO: 2 (*P. jirovecii* mtSSU gene) and the sequence complementary to SEQ ID NO: 2, more particularly without hybridizing to any of SEQ ID NO: 3, the sequence complementary to SEQ ID NO: 3, SEQ ID NO: 2 and the sequence complementary to SEQ ID NO: 2.

Said second probe may also not hybridize to human DNA or RNA.

Advantageously, said second probe specifically hybridizes to the sequence of SEQ ID NO: 1 or the complementary sequence thereof, more particularly to the sequence of SEQ ID NO: 10 or the complementary sequence thereof.

The sequence of said second probe may e.g., consist of or comprise a hybridization portion, which is or acts as the hybridization portion of the probe, i.e., which is or acts as the DNA or RNA portion, which confers to the second probe the capacity to hybridize to the cDNA reverse-transcript of said second *P. jirovecii* mitochondrial gene.

Said hybridization portion may e.g., be a DNA or RNA sequence of 17-21 nucleotides (more particularly of 19 nucleotides), which hybridizes to the sequence of SEQ ID NO: 1 or the sequence complementary to SEQ ID NO: 1, more particularly to the sequence of SEQ ID NO: 10 or the sequence complementary to SEQ ID NO: 10, without hybridizing to any of SEQ ID NO: 3 and the sequence complementary to SEQ ID NO: 3, or to any of SEQ ID NO: 2 and the sequence complementary to SEQ ID NO: 2, more particularly without hybridizing to any of SEQ ID NO: 3, the sequence complementary to SEQ ID NO: 3, SEQ ID NO: 2 and the sequence complementary to SEQ ID NO: 2.

Said hybridization portion of said second probe may also not hybridize to human DNA or RNA. Said hybridization portion of said second probe may specifically hybridize to the sequence of SEQ ID NO: 1 or to the complementary sequence thereof, more particularly to the sequence of SEQ ID NO: 10 or to the complementary sequence thereof. For example, the hybridization portion of said second probe is the (19 nucleotide-long) sequence of SEQ ID NO: 13 or the complementary sequence thereof.

The sequence of said second probe may consist of said hybridization portion.

Alternatively, the sequence of said second probe may comprise other DNA or RNA sequence(s) in addition to said hybridization portion, e.g., other DNA or RNA sequence(s) linked to the 5' and/or 3' terminal end(s) of said hybridization portion. This(these) other DNA or RNA sequence(s) should not (significantly) reduce the hybridization specificity of said hybridization portion. Said other DNA or RNA sequence(s) may e.g., be beacon arm(s), more particularly a 5' beacon arm and a 3' beacon arm, which impart a hairpin-configuration to said second probe when unhybridized (e.g., the 3' beacon arm is complementary to the 5' beacon arm). The total length of said second probe advantageously is of 25-29 nucleotides, or of 24-28 nucleotides, or of 23-27 nucleotides, or of 22-36 nucleotides.

Said second probe may comprise (e.g., be covalently linked to) at least one fluorophore (e.g., 6-carboxyfluorescein, or tetrachlorofluorescein) and/or at least one quencher (e.g., a carboxytetramethylrhodamine fluorescent dye (e.g., TAMRA®), the Black Hole Quencher®-0, the Black Hole Quencher®-1, the Black Hole Quencher®-2, the Black Hole Quencher®-3, or the Minor Groove Binder® quencher).

Said second probe may e.g., be a Locked Nucleic Acid (LNA) probe.

Said second probe may e.g., be a DNA or RNA probe.

For example, said second probe may be a TAQMAN® probe, i.e., a probe, wherein a fluorophore is covalently attached to its 5'-end and a quencher is covalently attached to its at the 3'-end (e.g., TAMRA® or BHQ®-1). A TAQMAN® probe is degraded by the 5'-3' exonuclease activity of the PCR polymerase, thereby releasing the fluorophore from it (and from the proximity of the quencher).

Alternatively, said second probe may be a beacon probe, i.e., a probe which in addition to said hybridization portion, comprises a beacon arm linked to the 5' terminal end and a beacon arm linked to the 3' terminal end (which impart a hairpin-configuration to said second probe when unhybridized), and which carries a fluorophore covalently linked to one of said two beacon arms, and a quencher linked to the other of said two beacon arms. Alternatively, said second probe may be a SCORPION® probe (i.e., a probe, which is linked to a fluorophore at one of its ends and which is linked at the other end to a primer via a PCR blocker).

The quantification may also be performed using at least two of said second probes (i.e., two different second probes) each comprising at least one fluorophore (e.g., as LIGHT-CYCLER® hybridization probes).

The Tm of the probe may be 4-10° C. higher than the Tm of the primer pair.

For example, when said second *P. jirovecii* mitochondrial gene is the *P. jirovecii* gene, the sequence of which codes for the Cytb protein, said second probe may hybridize to the sequence of SEQ ID NO: 3 or the complementary sequence thereof, more particularly to the sequence of SEQ ID NO: 30 or the complementary sequence thereof, without hybridizing to any of SEQ ID NO: 1 (*P. jirovecii* mtLSU gene) and the sequence complementary to SEQ ID NO: 1, or to any of SEQ ID NO: 2 (*P. jirovecii* mtSSU gene) and the sequence complementary to SEQ ID NO: 2, more particularly to any of SEQ ID NO: 1, the sequence complementary to SEQ ID NO: 1, SEQ ID NO: 2 and the sequence complementary to SEQ ID NO: 2. Said second probe may also not hybridize to human DNA or RNA. Advantageously, said second probe specifically hybridizes to the sequence of SEQ ID NO: 3 or the complementary sequence thereof, more particularly to the sequence of SEQ ID NO: 30 or the complementary sequence thereof.

The sequence of said second probe may e.g., consist of or comprise a hybridization portion, which is or acts as the hybridization portion of the probe, i.e., which is or acts as the DNA or RNA portion, which confers to the second probe the capacity to hybridize to the cDNA reverse-transcript of said second *P. jirovecii* mitochondrial gene.

Said hybridization portion may e.g., be a DNA or RNA sequence of 19-30 nucleotides (more particularly of 20-24 nucleotides, more particularly of 22 nucleotides), which hybridizes to the sequence of SEQ ID NO: 3 or the sequence complementary to SEQ ID NO: 3, more particularly to the sequence of SEQ ID NO: 30 or the sequence complementary to SEQ ID NO: 30, without hybridizing to any of SEQ ID NO: 1 and the sequence complementary to SEQ ID NO: 1, or to any of SEQ ID NO: 2 and the sequence complementary to SEQ ID NO: 2, more particularly to any of SEQ ID NO: 1, the sequence complementary to SEQ ID NO: 1, SEQ ID NO: 2 and the sequence complementary to SEQ ID NO: 2. Said hybridization portion of said second probe may also not hybridize to human DNA or RNA. Said hybridization portion of said second probe may specifically hybridize to the sequence of SEQ ID NO: 3 or to the complementary sequence thereof, more particularly to the sequence of SEQ ID NO: 30 or to the complementary sequence thereof. For example, the hybridization portion of said second probe is the (22 nucleotide-long) sequence of SEQ ID NO: 33 or the complementary sequence thereof, or a LNA-counterpart thereof, such as the (22 nucleotide-long) sequence of SEQ ID NO: 58 or the complementary sequence thereof (SEQ ID NO: 59; cf. example 3 below).

The sequence of said second probe may consist of said hybridization portion.

Alternatively, the sequence of said second probe may comprise other DNA or RNA sequence(s) in addition to said hybridization portion, e.g., other DNA or RNA sequence(s) linked to the 5' and/or 3' terminal end(s) of said hybridization portion. This(these) other DNA or RNA sequence(s) should not (significantly) reduce the hybridization specificity of said hybridization portion. Said other DNA or RNA sequence(s) may e.g., be beacon arm(s), more particularly a 5' beacon arm and a 3' beacon arm, which impart a hairpin-configuration to said second probe when unhybridized (e.g., the 3' beacon arm is complementary to the 5' beacon arm). The total length of said second probe advantageously is of 28-32 nucleotides, or of 27-31 nucleotides, or of 26-30 nucleotides, or of 25-29 nucleotides.

Said second probe may comprise (e.g., be covalently linked to) at least one fluorophore (e.g., 6-carboxyfluorescein, or tetrachlorofluorescein) and/or at least one quencher (e.g., a carboxytetramethylrhodamine fluorescent dye (e.g., TAMRA®), the Black Hole Quencher®-0, the Black Hole Quencher®-1, the Black Hole Quencher®-2, the Black Hole Quencher®-3, or the Minor Groove Binder® quencher).

Said second probe may e.g., be a Locked Nucleic Acid (LNA) probe.

Said second probe may e.g., be a DNA or RNA probe. For example, said second probe may be a TAQMAN® probe, i.e., a probe, wherein a fluorophore is covalently attached to its 5'-end and a quencher is covalently attached to its at the 3'-end (e.g., TAMRA® or BHQ®-1). A TAQMAN® probe is degraded by the 5'-3' exonuclease activity of the PCR polymerase, thereby releasing the fluorophore from it (and from the proximity of the quencher).

Alternatively, said second probe may be a beacon probe, i.e., a probe which in addition to said hybridization portion, comprises a beacon arm linked to the 5' terminal end and a beacon arm linked to the 3' terminal end (which impart a hairpin-configuration to said second probe when unhybridized), and which carries a fluorophore covalently linked to one of said two beacon arms, and a quencher linked to the other of said two beacon arms.

Alternatively, said second probe may be a SCORPION® probe (i.e., a probe, which is linked to a fluorophore at one of its ends and which is linked at the other end to a primer via a PCR blocker).

The quantification may also be performed using at least two of said second probes (i.e., two different second probes) each comprising at least one fluorophore (e.g., as LIGHT-CYCLER® hybridization probes).

The Tm of the probe may be 4-10° C. higher than the Tm of the primer pair.

When said second *P. jirovecii* mitochondrial gene is the mtSSU gene, said second probe may hybridize to
  the *P. jirovecii* mtSSU gene, which is of SEQ ID NO: 2 or to the sequence complementary to SEQ ID NO: 2, more particularly to the sequence of SEQ ID NO: 15 (a *P. jirovecii* mtSSU target) or to the sequence complementary to SEQ ID NO: 15, and/or
  to the sequence of SEQ ID NO: 20 (another *P. jirovecii* mtSSU target) or to the sequence complementary to SEQ ID NO: 20, and/or
  to the sequence of SEQ ID NO: 25 (still another *P. jirovecii* mtSSU target) or to the sequence complementary to SEQ ID NO: 25.

More particularly, said second probe may hybridize to the sequence of SEQ ID NO: 2 or the complementary sequence thereof, more particularly to at least one of the sequences of SEQ ID NO: 15, 20, 25 and the complementary sequences thereof, without hybridizing to any of SEQ ID NO: 3 (*P. jirovecii* CYTB gene) and the sequence complementary to SEQ ID NO: 3, or to any of SEQ ID NO: 1 and the sequence complementary to SEQ ID NO: 1, more particularly without hybridizing to any of SEQ ID NO: 3, the sequence complementary to SEQ ID NO: 3, SEQ ID NO: 1 and the sequence complementary to SEQ ID NO: 1.

Said second probe may also not hybridize to human DNA or RNA.

Advantageously, said second probe specifically hybridizes to the sequence of SEQ ID NO: 2 or the complementary sequence thereof, more particularly to at least one of the sequences of SEQ ID NO: 15, 20, 25 and the complementary sequences thereof.

The sequence of said second probe may e.g., consist of or comprise a hybridization portion, which is or acts as the hybridization portion of the probe, i.e., which is or acts as the DNA portion, which confers to the second probe the capacity to hybridize to the cDNA reverse-transcript of said second *P. jirovecii* mitochondrial gene.

Said hybridization portion may e.g., be a DNA sequence of 23-29 nucleotides (more particularly of 25-27 nucleotides), which hybridizes to the sequence of SEQ ID NO: 2 or the sequence complementary to SEQ ID NO: 2, more particularly to at least one of the sequences of SEQ ID NO: 15, 20, 25 and the sequences complementary to SEQ ID NO: 10, 20, 25, without hybridizing to any of SEQ ID NO: 3 and the sequence complementary to SEQ ID NO: 3, or to any of SEQ ID NO: 1 and the sequence complementary to SEQ ID NO: 1, more particularly without hybridizing to any of SEQ ID NO: 3, the sequence complementary to SEQ ID NO: 3, SEQ ID NO: 1 and the sequence complementary to SEQ ID NO: 1.

Said hybridization portion of said second probe may also not hybridize to human DNA or RNA. Said hybridization portion of said second probe may specifically hybridize to the sequence of SEQ ID NO: 2 or to the complementary sequence thereof, more particularly to at least one of the sequences of SEQ ID NO: 15, 20, 25 and the complementary sequences thereof. For example, the hybridization portion of said second probe is the (25 or 27 nucleotide-long) sequence of SEQ ID NO: 18, 23 or 28 or the complementary sequence thereof.

The sequence of said second probe may consist of said hybridization portion.

Alternatively, the sequence of said second probe may comprise other DNA sequence(s) in addition to said hybridization portion, e.g., other DNA sequence(s) linked to the 5' and/or 3' terminal end(s) of said hybridization portion. This(these) other DNA sequence(s) should not (significantly) reduce the hybridization specificity of said hybridization portion. Said other DNA sequence(s) may e.g., be beacon arm(s), more particularly a 5' beacon arm and a 3' beacon arm, which impart a hairpin-configuration to said second probe when unhybridized (e.g., the 3' beacon arm is complementary to the 5' beacon arm). The total length of said second probe advantageously is of 31-37 nucleotides, or of 30-36 nucleotides, or of 29-36 nucleotides, or of 28-34 nucleotides.

Said second probe may comprise at least one fluorophore (e.g., 6-carboxyfluorescein, or tetrachlorofluorescein) and/or at least one quencher (e.g., a carboxytetramethylrhodamine fluorescent dye (e.g., TAMRA®), the Black Hole Quencher®-0, the Black Hole Quencher®-1, the Black Hole Quencher®-2, the Black Hole Quencher®-3, or the Minor Groove Binder® quencher).

Said second probe may be a TAQMAN® probe, i.e., a probe, wherein a fluorophore is covalently attached to its 5'-end and a quencher is covalently attached to its at the 3'-end (e.g., TAMRA® or BHQ®-1). A TAQMAN® probe is degraded by the 5'-3' exonuclease activity of the PCR polymerase, thereby releasing the fluorophore from it (and from the proximity of the quencher).

Alternatively, said second probe may be a beacon probe, i.e., a probe which in addition to said hybridization portion, comprises a beacon arm linked to the 5' terminal end and a beacon arm linked to the 3' terminal end (which impart a hairpin-configuration to said second probe when unhybridized), and which carries a fluorophore covalently linked to one of said two beacon arms, and a quencher linked to the other of said two beacon arms.

The Tm of the probe may be 4-10° C. higher than the Tm of the primer pair.

Advantageously, said at least one first probe is implemented in real-time PCR. More particularly, said at least one first probe advantageously is implemented in the same tube as said first primer pair in real-time PCR amplification.

Advantageously, said at least one second probe in implemented in real-time PCR. More particularly, said at least one second probe advantageously is implemented in the same tube as said second primer pair in real-time PCR amplification.

Advantageously, said at least one first probe and one second probe are implemented in real-time PCR. More particularly, said at least one first probe and said at least one second probe are implemented in the same tube as said first primer pair and second primer pair in real-time PCR amplification.

The application also relates to each individual product that is implemented or obtainable by a method of the application.

More particularly, the application also relates to each of said first primer pair, said second primer pair, said first probe and said second probe, individually as a product.

More particularly, the application also relates to each of said first cDNA targets, said second cDNA targets, said first RNA targets, said second RNA targets, said first amplicons and said second amplicons, individually as a product.

The application also relates to the association or combinations of such products.

More particularly, the application relates to the association or combination of at least two or at least three different elements from the following list of four (different) elements: said first primer pair, said second primer pair, said first probe and said second probe; or to the association or combination of the four of them.

More particularly, the application relates to the association or combination of said first probe and said second probe.

More particularly, the application relates to the association or combination of said first primer pair and said second primer pair.

More particularly, the application relates to the association or combination of said first primer pair and said first probe.

More particularly, the application relates to the association or combination of said second probe and said second primer pair.

For example, they can be associated or combined in a kit, more particularly in a kit for simultaneous, separate or sequential use, or in a composition, more particularly in a liquid composition, such as an amplification composition. Said association, combination, kit or composition may further comprise at least one reverse transcriptase (i.e., at least one RNA-dependent DNA polymerase), or at least one reverse transcriptase and at least one DNA-dependent DNA polymerase.

Advantageously, said kit comprises at least said first primer pair and/or at least said first probe, more particularly at least said primer pair and at least said first probe.

Said kit may further comprise an internal control for RNA extraction and/or purification, such as an IECR or such as at least one (real-time) probe, more particularly at least one (real-time) probe and at least one primer pair, which specifically detect a human gene (cf. above and example 2 below).

More particularly, the application relates to the association or combination of at least two or at least three or at least four or at least five different elements from the following list of six (different) elements: said first cDNA targets, said second cDNA targets, said first RNA targets, said second RNA targets, said first amplicons and said second amplicons; or or to the association or combination of the six of them. More particularly, the application relates to the association or combination of said first amplicons and said second amplicons. Each of said six elements can be contained in a composition, more particularly in a liquid composition, such as an amplification composition. Said association, combination or composition may further comprise at least one reverse transcriptase (i.e., at least one RNA-dependent DNA polymerase), or at least one reverse transcriptase and at least one polymerase (more particularly at least one DNA-dependent DNA polymerase).

Said reverse transcriptase (or said reverse transcriptase and DNA-dependent DNA polymerase) can be any reverse transcriptase (or any reverse transcriptase and DNA-dependent DNA polymerase), which the person of average skill in the art may find appropriate.

Examples of reverse transcriptase include the SUPERSCRIPT® III Reverse Transcriptase (RT) commercialized by INVITROGEN™ (INVITROGEN™ by LIFE TECHNOLOGIES™; 5791 Van Allen way; Carlsbad; Calif. 92008; U.S.A.).

Examples of polymerases (i.e., of DNA-dependent DNA polymerases) include a *Thermus aquaticus* polymerase.

Said product(s), association(s), combination(s), kit(s), composition(s) is(are) suitable for diagnosing or predicting *PneumoCystis* Pneumonia (PCP), more particularly for diagnosing or predicting whether a human patient (more particularly a human patient, who is a *Pneumocystis jirovecii* carrier) has or develops PCP, or for determining or predicting the efficacy of a drug or treatment against PCP in a human patient (more particularly a human patient, who is a *Pneumocystis jirovecii* carrier), or for determining whether PCP regresses or has been treated in a human patient who has been diagnosed to have PCP and who is receiving or has received a drug or treatment against PCP.

The application thus also relates to the (in vitro) use of said product(s), association(s), combination(s), kit(s), composition(s) for diagnosing or predicting *PneumoCystis* Pneumonia (PCP), more particularly for diagnosing or predicting whether a human patient (more particularly a human patient, who is a *Pneumocystis jirovecii* carrier) has or develops PCP, or for determining or predicting the efficacy of a drug or treatment against PCP in a human patient (more particularly a human patient, who is a *Pneumocystis jirovecii* carrier), or for determining whether PCP regresses or has been treated in a human patient who has been diagnosed to have PCP and who is receiving or has received a drug or treatment against PCP.

More particularly, the application relates to the in vitro use of a reverse transcriptase (i.e., a RNA-dependent DNA polymerase) and of oligonucleotides:
   for diagnosing or predicting *PneumoCystis* Pneumonia (PCP), more particularly for diagnosing or predicting whether a human patient (more particularly a human patient, who is a *Pneumocystis jirovecii* carrier) has or develops PCP, or
   for determining or predicting the efficacy of a drug or treatment against PCP in a human patient (more particularly a human patient, who is a *Pneumocystis jirovecii* carrier), or
   for determining whether PCP regresses or has been treated in a human patient who has been diagnosed to have PCP and who is receiving or has received a drug or treatment against PCP,
wherein said oligonucleotides comprise primers and/or probes, wherein said primers comprises a first primer pair and a second primer pair, wherein said probes comprise a first probe and a second probe,
   wherein said first primer pair and/or said first probe specifically hybridizes to the cDNA reverse transcripts of the RNA transcripts of said first *P. jirovecii* mitochondrial gene (cf. above),
   wherein said second primer pair and/or said second probe specifically hybridizes to the cDNA reverse transcripts of the RNA transcripts of said second *P. jirovecii* mitochondrial gene (cf. above).

For example, said first *P. jirovecii* mitochondrial gene is the *P. jirovecii* gene, the sequence of which codes for the Cytb protein, and said second *P. jirovecii* mitochondrial gene is a *P. jirovecii* gene, the sequence of which transcribes into a *P. jirovecii* ribosomal RNA (mtLSU gene or mtSSU gene, more particularly mtLSU gene).

For example, said first *P. jirovecii* mitochondrial gene is the mtSSU *P. jirovecii* gene, and said second *P. jirovecii* mitochondrial gene is the *P. jirovecii* mtLSU gene.

Said use may further comprises the use of a polymerase (i.e., of a DNA-dependent DNA polymerase).

Said use may further comprise the use a RNA extraction and/or purification internal control, such as an IECR or such as at least one (real-time) probe, more particularly at least one (real-time) probe and at least one primer pair, which specifically detect a human gene (cf. above and example 2 below).

The application also relates to a kit, which comprises said reverse transcriptase and said oligonucleotides. Said kit may further comprise a polymerase (i.e., a DNA-dependent DNA polymerase). Said kit can be viewed as a kit suitable for diagnosing or predicting *PneumoCystis* Pneumonia (PCP) in a human patient (more particularly, a human patient, who is a *Pneumocystis jirovecii* carrier), or for determining or predicting the efficacy of a drug or treatment against PCP in a human patient (more particularly, a human patient, who is a *Pneumocystis jirovecii* carrier), or for determining whether PCP regresses or has been treated in a human patient who has been diagnosed to have PCP and who receives or has received a drug or treatment against PCP. Said kit may further comprise written instructions for implementing said reverse transcriptase and said oligonucleotides (and optionally said polymerase) in these uses or applications.

Said kit may be a kit for simultaneous, separate or sequential use, more particularly for simultaneous use, of said reverse transcriptase and said oligonucleotides (or of said reverse transcriptase, said oligonucleotides and said polymerase). Said kit may comprise container(s) (e.g., tube(s)), wherein said reverse transcriptase and said oligonucleotides (or said reverse transcriptase, said oligonucleotides and said polymerase) are contained. Advantageously, said reverse transcriptase and said polymerase are contained in the same container (e.g., in the same tube). Said first primer pair can be contained in a container (e.g., tube), which is different from the container (e.g., tube) in which said second primer pair is contained. Said first probe can be contained in a container (e.g., tube), which is different from the container (e.g., tube) in which said second probe is contained. Said first primer pair and said first probe may be in the same container (e.g., tube). Said second primer pair and said second probe may be in the same container (e.g., tube).

Said kit may further comprise means for RNA extraction and/or purification. For example, said kit may further comprise cell lysis reagent(s) and/or buffer(s), and/or RNA purification means, such as e.g., a silica membrane.

Said kit may further comprise an internal control for RNA extraction and/or purification such as an IECR or such as at least one (real-time) probe, more particularly at least one (real-time) probe and at least one primer pair, which specifically detect a human gene (cf. above and example 2 below).

Each feature or combination of features, which has been described in the context of a method of the application, applies to each product, combination, association, kit or composition as such as well as to their uses, mutatis mutandis.

For example, the nucleotide sequence of each primer of said first and second primer pairs may independently consist of 15-30 nucleotides (e.g., of 18-28 or 19-27 or 20-26 nucleotides) (cf. above).

For example, the nucleotide sequence of each of said first and second probes independently consists of 17-37 nucleotides (e.g., of 20-24 or 28-32 or 17-21 or 25-29 or 23-29 or 31-37 nucleotides) (cf. above).

For example, said first or second primer pair is a primer pair, which anneals to the cDNA reverse transcripts of the RNA transcripts of said first or second P. jirovecii mitochondrial gene (or to the RNA transcripts of said first or second P. jirovecii mitochondrial gene as well as to the cDNA reverse transcripts thereof) to produce a cDNA amplicon, which is of 100-120 nucleotide-long (more particularly of 100-110 nucleotide-long, more particularly of 102-108 nucleotide-long, more particularly of 104-106 nucleotide-long, more particularly of 105 nucleotide-long), and which comprises or is the sequence of SEQ ID NO: 30, or
a cDNA sequence, which is of the same length as SEQ ID NO: 30 and which is at least 95% (more particularly at least 96%, at least 97%, at least 98% or at least 99%) identical to SEQ ID NO: 30. For example, said first or second primer pair is the primer pair of SEQ ID NO: 31 and SEQ ID NO: 32. For example, said first or second primer pair is the primer pair of SEQ ID NO: 60 and SEQ ID NO: 32.

For example, said first or second primer pair may e.g., be a (mtLSU) primer pair, which anneals to the cDNA reverse transcripts of the RNA transcripts of the P. jirovecii mtLSU gene (or to the RNA transcripts of the P. jirovecii mtLSU gene as well as to the cDNA reverse transcripts thereof) to produce a cDNA amplicon, which is of 115-125 nucleotides (more particularly of 117-124 nucleotides, more particularly of 119-123 nucleotides, more particularly of 121 nucleotides), and which comprises or is the sequence of SEQ ID NO: 10, or
a cDNA sequence, which is of the same length as SEQ ID NO: 10 and which is at least 95% (more particularly at least 96%, at least 97%, at least 98% or at least 99%) identical to SEQ ID NO: 10. For example, said first or second primer pair is the (mtLSU) primer pair of SEQ ID NO: 11 and SEQ ID NO: 12.

For example, said first or second primer pair may alternatively be a (mtSSU) primer pair, which anneals to the cDNA reverse transcripts of the RNA transcripts of the P. jirovecii mtSSU gene (or to the RNA transcripts of the P. jirovecii mtSSU gene as well as to the cDNA reverse transcripts thereof) to produce a cDNA amplicon, which is of 60-110 nucleotides (more particularly of 76-92 nucleotides, more particularly of 76, 82 or 92 nucleotides, more particularly of 82 nucleotides), and comprises or is the sequence of SEQ ID NO: 15, or
a cDNA sequence, which is of the same length as SEQ ID NO: 15 and which is at least 95% (more particularly at least 96%, at least 97%, at least 98% or at least 99%) identical to SEQ ID NO: 15. For example, said first or second primer pair is the (mtSSU) primer pair of SEQ ID NO: 16 and SEQ ID NO: 17.

For example, said first or second primer pair may alternatively be a (mtSSU) primer pair, which anneals to the cDNA reverse transcripts of the RNA transcripts of the P. jirovecii mtSSU gene (or to the RNA transcripts of the P. jirovecii mtSSU gene as well as to the cDNA reverse transcripts thereof) to produce a cDNA amplicon, which is of 60-110 nucleotides (more particularly of 76-92 nucleotides, more particularly of 76, 82 or 92 nucleotides, more particularly of 92 nucleotides), and comprises or is the sequence of SEQ ID NO: 20, or
a cDNA sequence, which is of the same length as SEQ ID NO: 20 and which is at least 95% (more particularly at least 96%, at least 97%, at least 98% or at least 99%) identical to SEQ ID NO: 20. For example, said first or second primer pair is the (mtSSU) primer pair of SEQ ID NO: 21 and SEQ ID NO: 22.

For example, said first or second primer pair may alternatively be a (mtSSU) primer pair, which anneals to the cDNA reverse transcripts of the RNA transcripts of the P. jirovecii mtSSU gene (or to the RNA transcripts of the P. jirovecii mtSSU gene as well as to the cDNA reverse transcripts thereof) to produce a cDNA amplicon, which is of 60-110 nucleotides (more particularly of 76-92 nucleotides, more particularly of 76, 82 or 92 nucleotides, more particularly of 76 nucleotides), and comprises or is the sequence of SEQ ID NO: 25, or
a cDNA sequence, which is of the same length as SEQ ID NO: 25 and which is at least 95% (more particularly at least 96%, at least 97%, at least 98% or at least 99%) identical to SEQ ID NO: 25. For example, said first or second primer pair is the (mtSSU) primer pair of SEQ ID NO: 26 and SEQ ID NO: 27.

In accordance with the understanding of the person of average skill in the art, a primer pair, which anneals to a (target) cDNA or RNA or DNA, can be viewed as a pair of forward and reverse primers. The forward primer anneal to a first sequence, which is contained in said (target) cDNA or RNA or DNA, and the reverse primer anneals to a second sequence, which is contained in the sequence complementary to said (target) cDNA or RNA or DNA. The 5' end of said first (target) sequence and the 5' end of said second (target) sequence can be viewed as the start and end positions of the amplicon produced by said primer pair. More particularly, and still in accordance with the understanding of the person of average skill in the art, a primer pair, which anneals to a (target) cDNA or RNA or DNA, can be viewed as a primer pair, wherein:

a first primer of the pair is at least 95% (more particularly at least 96%, at least 97%, at least 98% or at least 99%) identical to a first sequence, which is contained in said (target) cDNA or RNA or DNA, and which is of the same length as said first primer, and the second primer of the same pair is at least 95% (more particularly at least 96%, at least 97%, at least 98% or at least 99%) identical to a second sequence, which is contained in the sequence complementary to said (target) cDNA or RNA or DNA and which is of the same length as said second primer.

In accordance with the understanding of the person of average skill in the art, the 5' end of said first (target) sequence and the 5' end of said second (target) sequence can be viewed as the start and end positions of the amplicon produced by said primer pair.

The application also relates to a solid support, such as a nucleic acid microarray, nanoarray, chip or lane, onto which said first primer pair and/or said first probe is/are attached or bound. Said solid support may further comprise said second primer pair and/or said second probe attached or bound thereto. Said solid support may e.g., be a plastic, glass or silicon microarray, nanoarray, chip or lane.

The application also relates to the (in vitro) use of a P. jirovecii transcriptome for diagnosing or predicting PneumoCystis Pneumonia (PCP), more particularly for diagnosing or predicting whether a human patient (more particularly a human patient, who is a *Pneumocystis jirovecii* carrier) has or develops PCP, or for determining or predicting the efficacy of a drug or treatment against PCP in a human patient (more particularly a human patient, who is a *Pneumocystis jirovecii* carrier), or for determining whether PCP regresses or has been treated in a human patient who has been diagnosed to have PCP and who is receiving or has received a drug or treatment against PCP. Said use comprises detecting and/or quantifying, more particularly quantifying, (the number of or the concentration of) the RNA transcripts of said first *P. jirovecii* mitochondrial gene and (the number of or the concentration of) the RNA transcripts of said second *P. jirovecii* mitochondrial gene. For example, said use comprises detecting and/or quantifying, more particularly quantifying, (the number of or the concentration of) the RNA transcripts of said first *P. jirovecii* mitochondrial gene (CYTB gene) and (the number of or the concentration of) the RNA transcripts of said second *P. jirovecii* mitochondrial gene (mtLSU or mtSSU, more particularly mtLSU). For example, said use comprises detecting and/or quantifying, more particularly quantifying, (the number of or the concentration of) the RNA transcripts of said first *P. jirovecii* mitochondrial gene (mtSSU) and (the number of or the concentration of) the RNA transcripts of said second *P. jirovecii* mitochondrial gene (mtLSU).

The application also relates to a nucleic acid library, which is or comprises the transcriptome of *P. jirovecii*, more particularly the RNA transcripts of *P. jirovecii*. This transcriptome or transcripts can be those of a patient's biological sample as discussed above. Such a library is useful for detecting and/or quantifying, more particularly quantifying, (the number of or the concentration of) the RNA transcripts of said first *P. jirovecii* mitochondrial gene and (the number of or the concentration of) the RNA transcripts of said second *P. jirovecii* mitochondrial gene. For example, such a library is useful for detecting and/or quantifying, more particularly quantifying, (the number of or the concentration of) the RNA transcripts of said first *P. jirovecii* mitochondrial gene (CYTB gene) and (the number of or the concentration of) the RNA transcripts of said second *P. jirovecii* mitochondrial gene (mtLSU or mtSSU). For example, such a library is useful for detecting and/or quantifying, more particularly quantifying, (the number of or the concentration of) the RNA transcripts of said first *P. jirovecii* mitochondrial gene (mtSSU) and (the number of or the concentration of) the RNA transcripts of said second *P. jirovecii* mitochondrial gene (mtLSU).

The library of the application is notably suitable for high throughput sequencing, e.g., for implementation of the RNA-Seq method described in Wang et al. 2009.

Said library can be used in accordance with the application, e.g., for diagnosing or predicting *PneumoCystis* Pneumonia (PCP), more particularly for diagnosing or predicting whether a human patient (more particularly a human patient, who is a *Pneumocystis jirovecii* carrier) has or develops PCP, or for determining or predicting the efficacy of a drug or treatment against PCP in a human patient (more particularly a human patient, who is a *Pneumocystis jirovecii* carrier), or for determining whether PCP regresses or has been treated in a human patient who has been diagnosed to have PCP and who is receiving or has received a drug or treatment against PCP.

Said nucleic acid library can e.g., be a DNA library, which comprises or consists of DNA fragments of 40-400 bp, wherein each of said DNA fragments comprise the cDNA reverse transcript of a *P. jirovecii* RNA fragment of 40-400 nucleotides, wherein said *P. jirovecii* RNA fragment of 40-400 nucleotides is a fragment of 40-400 nucleotides from the RNA transcript of a *P. jirovecii* mitochondrial gene.

Advantageously, said *P. jirovecii* mitochondrial gene is the mtLSU gene, the mtSSU or the CYTB gene.

Advantageously, said DNA library comprises or consists of:
  at least one first DNA fragment of 40-400 bp, which comprises the cDNA reverse transcript of a fragment of 40-400 nucleotides from the RNA transcript of the *P. jirovecii*, CYTB gene and
  at least one second DNA fragment of 40-400 bp, which comprises the cDNA reverse transcript of a fragment of 40-400 nucleotides from the RNA transcript of the *P. jirovecii* mtLSU or mtSSU gene,
wherein said fragment of 40-400 nucleotides from the RNA transcript of the *P. jirovecii* CYTB gene is different from said fragment of 40-400 nucleotides from the RNA transcript of the *P. jirovecii* mtLSU or mtSSU gene.

Advantageously:
  said fragment of 40-400 nucleotides from the RNA transcript of the *P. jirovecii* CYTB gene is specific of the RNA transcript of the *P. jirovecii* CYTB gene,
  said fragment of 40-400 nucleotides from the RNA transcript of the *P. jirovecii* mtLSU gene is specific of the RNA transcript of the *P. jirovecii* mtLSU gene,
  said fragment of 40-400 nucleotides from the RNA transcript of the *P. jirovecii* mtSSU gene is specific of the RNA transcript of the *P. jirovecii* mtSSU gene.

Advantageously, said DNA library comprises or consists of:
  at least one first DNA fragment of 40-400 bp, which comprises the cDNA reverse transcript of a fragment of 40-400 nucleotides from the RNA transcript of the *P. jirovecii*, mtSSU and
  at least one second DNA fragment of 40-400 bp, which comprises the cDNA reverse transcript of a fragment of 40-400 nucleotides from the RNA transcript of the *P. jirovecii* mtLSU gene,
wherein said fragment of 40-400 nucleotides from the RNA transcript of the *P. jirovecii* mtSSU gene is different from said fragment of 40-400 nucleotides from the RNA transcript of the *P. jirovecii* mtLSU.

In said DNA libraries, each of said DNA fragments may optionally further comprise:
  a first DNA of 30-150 bp, which is not a fragment of *P. jirovecii* cDNA or DNA, and which is (covalently) linked to the 5' end said cDNA reverse transcript (e.g., a DNA of 30-150 bp, which is a first sequencing adaptor), and
  a second DNA of 30-150 bp, which is not a fragment of *P. jirovecii* cDNA or DNA, and which is (covalently) linked to the 3' end of said cDNA reverse transcript (e.g., a DNA of 30-150 bp, which is a second sequencing adaptor, different from said first sequencing adapter).

The application also relates to a computer program product, for storage in a memory of a processing unit or on a removable memory support for cooperation with a reader of said processing unit, which comprises (code) instructions for carrying out a method of the application (when read or executed by a processor or microprocessor).

More particularly, the computer program product of the application may comprise (code) instructions, which (when read or executed by a processor or microprocessor) align RNA or cDNA sequence reads on the mitochondrial DNA sequence of *P. jirovecii* to detect and/or quantify (the number of or the concentration of) the RNA transcripts of said first P. jirovecii mitochondrial gene (e.g., cytb or mtSSU) and of said second P. jirovecii mitochondrial gene (e.g., mtLSUor mtSSU).

The application also relates to a computer device, comprising a processing unit in the memory of which is stored the computer program product of the application, and measurement values for the respective values of quantification of the RNA transcripts of said first P. jirovecii mitochondrial gene (e.g., cytb or mtSSU) and of said second P. jirovecii mitochondrial gene (e.g., mtLSUor mtSSU).

The application also relates to a kit for use in the treatment and/or prevention and/or palliation of PCP in a human patient, (more particularly, a human patient, who is a Pneumocystis jirovecii carrier), wherein comprises one or several ingredient(s) for simultaneous, separate or sequential use in said treatment and/or prevention and/or palliation. Said one or several active ingredient(s) may e.g., be
- (the combination or association of) at least one dihydrofolate reductase inhibitor and at least one sulfonamide antibiotic, e.g., (the combination or association of) trimethoprim and sulfamethoxazole (e.g., the cotrimoxazole combination drug), or
- aerosolized pentamidine, or
- primaquine and clindamycin, or
- atovaquone, or
- pyrimethamine, or
- echinocandin(s) (including caspofungin), or
- corticosteroid(s) (including prednisone), or
- anti-inflammatory active ingredient(s), or
- dapsone, or
- dapsone and pyrimethamine and leucovorin.

More particularly, said human patient is a human patient, who has been diagnosed or predicted to be at high risk of having or developing PCP with a method of the application.

The application also relates to a method for the treatment and/or prevention and/or palliation of PCP in a human patient in need thereof, wherein said human patient is a Pneumocystis jirovecii carrier. Said method comprises:
- diagnosing or predicting whether said human patient is at high risk of having or developing PCP with a method of the application,
- providing a drug or a combination of drugs for the treatment and/or prevention and/or palliation of PCP, and
- administering said drug or a combination of drugs to said human patient.

Said drug or combination of drugs may comprise
- (the combination or association of) at least one dihydrofolate reductase inhibitor and at least one sulfonamide antibiotic, e.g., (the combination or association of) trimethoprim and sulfamethoxazole (e.g., the cotrimoxazole combination drug), or
- aerosolized pentamidine, or
- primaquine and clindamycin, or
- atovaquone, or
- pyrimethamine, or
- echinocandin(s) (including caspofungin), or
- corticosteroid(s) (including prednisone), or
- anti-inflammatory active ingredient(s), or
- dapsone, or
- dapsone and pyrimethamine and leucovorin.

The term "comprising", which is synonymous with "including" or "containing", is open-ended, and does not exclude additional, un-recited element(s), ingredient(s) or method step(s), whereas the term "consisting of" is a closed term, which excludes any additional element, step, or ingredient which is not explicitly recited.

The term "essentially consisting of" is a partially open term, which does not exclude additional, un-recited element(s), step(s), or ingredient(s), as long as these additional element(s), step(s) or ingredient(s) do not materially affect the basic and novel properties of the invention.

The term "comprising" (or "comprise(s)") hence includes the term "consisting of" ("consist(s) of"), as well as the term "essentially consisting of" ("essentially consist(s) of"). Accordingly, the term "comprising" (or "comprise(s)") is, in the application, meant as more particularly encompassing the term "consisting of" ("consist(s) of"), and the term "essentially consisting of" ("essentially consist(s) of").

In an attempt to help the reader of the present application, the description has been separated in various paragraphs or sections. These separations should not be considered as disconnecting the substance of a paragraph or section from the substance of another paragraph or section. To the contrary, the application encompasses all the combinations of the various sections, paragraphs and sentences that can be contemplated.

Each of the relevant disclosures of all references cited herein is specifically incorporated by reference. The following examples are offered by way of illustration, and not by way of limitation.

EXAMPLES

Example 1

Material and Methods

Samples

A total of 200 consecutive BronchoAlveolar Lavage (BAL) Fluids (BALF) were collected prospectively between the 1 Jan. 2013 and the 31 Aug. 2013. Fiber optic bronchoscopy was performed after patients stated their non-opposition to the use of BALF for testing new diagnostic procedures. The site of BAL was guided by the topography of the lesions upon lung high-resolution computed tomography, and BAL was performed with four 50-mL aliquots of sterile saline solution following the standardized protocol of Alanio et al. 2011. BALF was sent within the hour after collection to the laboratory. Upon arrival, the BALF was centrifuged at 2,800 g for 10 minutes, the pellet was re-suspended with 4 mL of phosphate-buffered saline and split in four fractions of 1 mL. The four tubes were then centrifuged at 8,000 g for 5 minutes and the pellets of two tubes were frozen and stored at −80° C. The two other pellets were used for classical staining, immunofluorescence procedure and DNA extraction as described in Alanio et al. 2011. Classical staining, immunofluorescence and the Cq value of the DNA PCR (Alanio et al. 2011) were recorded for each BALF and also for any non-invasive diagnostic specimen (mostly sputa and induced sputa) performed before the BALF.

Seven samples were repeated and were considered as new infectious episodes except if PCP diagnosis based on immunofluorescence was positive before.

Patients

The 192 corresponding patients were cared for in three hospitals in the north of Paris (Hospital Saint Louis, 1 avenue Claude Vellefaux 75010 Paris France; Hospital Lariboisière, 2 rue Ambroise Paré 75010 Paris France; and Hospital Robert Debré, 48 Boulevard Serrurier 75019 Paris France). The sex ratio was 1.5 and the median age was 50 years with a range of 02 to 82 years. In the patients with evidence of P. jirovecii (immunofluorescence, DNA or RNA detection), the whole medical file including clinical, radiological and biological features was retrospectively analyzed by two expert physicians (one pneumologist and one infectious disease specialist). For specific analyses, the date of introduction and duration of cotrimoxazole therapy at the time of the BAL was recorded. Outcome at the last follow-up visit was recorded from the electronic medical file. Underlying diseases were divided into four categories (HIV positivity, hematological malignancies, solid organ transplantation, others).

Probability of PCP Classification

PneumoCystis pneumonia (PCP) diagnosis as the etiology of an acute pneumonia episode were classified as proven, probable, possible and no PCP. Criteria used for proven, probable, possible classification are summarized in Table 1 below. Other clinical situations were classified as no PCP.

TABLE 1

Criteria used to classify patients regarding *Pneumocystis* pneumonia (PCP) probability in a context of acute pneumonia episode

| PCP | Compatible Background (ID) | Compatible clinical and radiological presentation | Favorable outcome under therapy | No prophylaxis | No alternative diagnosis | Positive IF (BAL or IS)* |
|---|---|---|---|---|---|---|
| Proven | X | X | X | | X | X |
| Probable | X | X | X | X | X | |
| Possible | X | X | X | X | | |

*based on BALF and sputa specimens.

RNA Extraction

The day of the experiment, the pellet of one tube was thawed and RNA was extracted using the RNeasy® plus mini kit (catalog number 74136) from QIAGEN® France S.A.S. (3 avenue du Canada; LP 809; 91974 COURTA-BOEUF CEDEX; FRANCE). Briefly: 350 µL of lysing buffer RLT+1% betamercaptoethanol were added to the pellet and vortexed. 350 µL of ethanol 70% were added and mixed gently. The final volume was deposited in the column and additional steps were performed following the manufacturer's recommendations. We obtained at the end 50 µL of RNA extracted.

Gene Sequences

The reference sequence used to design primers and a probe for the quantification of the RNA transcripts of the mitochondrial Large SubUnit (mtLSU, also known as RNL) is referenced in GENBANK® under the accession number JX499143.1 REGION: 12373..15076 (SEQ ID NO: 1), which is:

(SEQ ID NO: 1)
AAAGGGGTTATTAAGGATAACTAGCTAATATATTTAAGGAGGTGTCGAAT

CCAAAATCATTATTCTAAAGATGTAATAATGTAAATCCGAGAGGGAAACC

TCAATACTAATTACGAAGTGAAATGAAACATCTTAGTAACTTTAGGAAAA

GAAATCAACCGAGATTTTATGAGTAGTGGTGAGCGAAAGTAAATTAGCCA

AGTATTTATATAATAGATTAAATATAATTAATTACAAAAATTAATTGTAG

TCTTCGAATGAAAGATCAATCTCCTCTTTTAAAAGTTGGAATGCTTTAGC

CAAGGATGGTGAAAGCCCAGAGTCCCAGGAATATAAATACAAAATAAGTA

GAACGAGAGATAACTTGTTTGAATACAGATAATATTTATGTAGTAATGTA

TGGAACAATTCAACTTTATACTAATTACACATAAGATTATTAGGGGAACT

ATCCTCTAAGGCTAAATATAATATATTAAGCGATAGTGAAGAGTACCGTG

AGGGAAAGTTGAAAAGAATATAAGTGAAACAGATCTTGAATTAATAACCT

TATAAGCAGTCGGAGGTCCAAAGACTGACGACGTACCTTTTGCATAATGG

GTCAGCAAGTTAATATGCAATGCAAGTCGCAAGACCTAATGAAGATGATT

CTGAACAGGGATATAAAGTATTGTGTATTAGACCCGAAATCTAGTGATCT

TACTATGATCAGACAACTTCAGGTCGAACTGGTGTACGTCGCAAAGTACT

CAGAAGAATTGTGGTAAGTAGTGAAATACAAATCGGACTAGGATATAGCT

GGTTTTCTGCGAAAATTGTTTTGGCAAATTGTTTATTCCTCTAAAAAATA

GTAGGTATAGCACTGAATATCTCGAGGGAGTATGAAAATATTTATCTCAG

ATATTTAATCTCAAAATAACTATTTCTTAAAATAAATAATCAGACTATGT

GCGATAAGGTAGATAGTCGAAAGGGAAACAGCCCAGAACAGTAATTAAAG

CTCCCCAATTAATATTAAGTGAAATAAAAGTTGTTGGATATCTAAAACAG

TTAAGAAGTGGGCTTGGAAACAGCCATCTTTTAAAGAACACGTAAAAGTG

CAATGATCTATGATCTCCAGCGCTGAAAATATCCGGATCTAAATATTATG

CTGAAAGACTGTTTATTTTTCTTTTAATTAACTGTAATTTAATTAAAAAA

AATAAGGTAGCAGAACATTTAGTAAATGTGTGAAGAATAGTATTTTATTA

TTCGGACATAACTAAAGAGAGAATGCTGACATGAGTAACGTTAAAATAGG

TGAAAATCCTATTCGCCGAAAATGGAAGGTTTTTATAGTTCCGCTTAACT

ACTATAAATCAGATCGGTCTCTAACAGTAATTCGAATGAATAATGGATGA

GAAACATATATAAAAATCGTAAGATTCAGGAAAAATTATATGTAATAACC

GTACTAAAACCGACACAGGTCCATGAATATTAATGTATACAGGCGAATGA

GAGAATTATTGCGAAGGAACTCGGCAAATGAATTTCGTAATTTCGAGATA

AGAAATACCAATGGTGTCAATAATGAGGTTGTACAACTGTTTACTTAAAA

CACAGTACTTTGCAAAGATTAAAAATCATTGTATAAAGTATGAAATCTGC

CCAATGCTAAATGATAAAATCTATGGCTTCAATGGCTGTGGGTATAATGT

TTAGTGAATGGCGGCCTTAACTATAAGGGTCCTAAGGTAGCGAATTTCCT

TGGCCGTTAAATGCGGTCCCGCACGAATGATTTAATGATACAACAACTGT

CTCCGCAATAAACTCAGTGAAATTGGATTAGCCGTGAAGATACGGTTTGT

ATATAGATAGACGGGAAGACCCTATGCAGCTTAACTGTTGTTCTTTATTG

TTTTTTTAAATTCTCTTCGTAGTGCTAAAAGGTAGTCGATGAGATGTCA

GTGAAAAACCTTTGTGGAAATTTAAAATAACTAACTTACTTAATTAAGAA

```
CAGTGAAGATTAGACAGTTTCTGTGGGGCGCAGATCTCAAAAATTGTATC

TGAGATGCCCAAAGGCATGGTGAAATTGGATGGTAACCAATGAATGTACA

TTTGTATATCTAGTGGTCTTTAATTACTAGATGATGTTTTATTTAATAAA

GTGTAATGGCATAACTCATGCTTAACAGTAAGACTAACAAGTCAAACTGA

CATGTAAGTGGGCATAATGACCCTCGTTTACATTATGGATTGGAACGAG

AGTAACGAATAAAAGCTACGCTAGGGATAACAGGGTTATTTCGTGTGAGA

GATCGTATTGACCACGAAGTTTGCCACCTCGATGTCGACTCAACCTATCC

TCCAGGAGTAGAATATTGGAAGGGTTCGGCTGTTCGCCGATTAAAAGGTT

ACGTGAGTTGGGTTAAAAACGTTGTGAAACAGTTTGGTTCCTATCTTCTA

TATATTTTAAAAGTTAATGGAGAATTTACTCTTTGTACGCAAGGATCAGA

TGTATTTTAACCTCTGGTTTGTCTGTTGTTTGTCGCATCGCAGATACGCT

ATGTTGATACGAATAAATATTGAAAGCATATTAAATATGAAGTCCTACT

CCATAAACTTTCTTGCGTTGTAGACTACGACGTAGATAGGCTTTATCTGT

AAGAATAGTAATGTTTTAAGGTATAAAGTACTAATTTTTTTTGACTGAA

TTAT.
```

The reference sequence used to design primers and a probe for the quantification of the RNA transcripts of the mitochondrial Small SubUnit (mtSSU, also known as RNS), is referenced in GENBANK® under the accession number JX499143.1, REGION: 31755 . . . 33192 (SEQ ID NO: 2), which is:

```
                                    (SEQ ID NO: 2)
TAAGATAATTCACAAAAGAAAGAGTTTAATGTTAGCTCCGAATCAACGCT

ATCTAGAGGCATTACACATGCAAATCGTACGTTTAAAGTGGTGAACAGGT

GAGTAAAGATAGAAATCTACCTATTCATAAGGTTAGATACCTTTTAAAAG

AACAATTGTTTGTGAATAGATGAGTCTAAGTGGGGGAGGTAGTTGTGAGG

TGAAGATCCTCCCAAGCCTAAGAACCCTAGTTATATTTGAAAGAATGAAT

AACCACATTGGCTCTGAAACAACAGCCAAGATTTTCATCCAAGAAAGTCC

AGCAGTGGGAATATTGGTCAATGATCGAAAGATTGAACCAGCTATCTAG

AAGAATTTGTATTCTGTTATTAGAGAGGATTATGACGTTATCTAATTAAA

GTCTCGACCAATTCTCGTGCCAGCAGTCGCGGTAAGACGAGTGAGGCTAG

CGTTATTCATAATTATTAGGTCTAAAGGGTACGTAGATGGTTAACTTATC

TGTTATTTATGTGTGAAGGAATTAGTATTCTAATTCGTTTTATTAGTATT

CTAATTTTTTAATAGAACATAAAAGAATTGGATAAATTGATTAACTAGA

GTCGAATAGAAGAATAAAGAATTTTAAGAGTAGAGATGAAATTCAACGAT

ACTTAAAGGACTGCCAATGGCGAAAGCATTATTCTAGGTAACGACTGACA

TTGAGGTACGTAGGCATAAGTAGCGAAAAGGATTAGATACCCTTGTAGTT

TATGCTGTAAACGATGAATGCTAGAGGTCAGAATTTATTTATTTTTGGTC

TTTAAGTGAAGATTTTAAGCATTCCACCTGAGAAGTACTGTCGCAAGACT

GAAACTCAAAACATTAGACGGTCACAGAGATCAGCAGTGAAGCATGTTGT

TTAATTCGATAACCCACGATAAATCTTACCACTTCTTGCATATTTTCCTA

TTCGGAATTTACAGGTGTTGCATGGCTGTCTTTAGTTCGTGTTGTGAAAT

GTTAGGTTTATTCCGATAACGAACGTAAACCTTGTCCTTAATTATTTTAA

GGAAATGTCTATCGATATTATAGATGAATGAGGATGAAGACAAGTCCTCA

TGACCCTTATGAAGTGGGCTACAGACGTGCTGCAAAATTTTCTACAATGG

GATGCAATGATGGAAGTCGGAGCTAATCCCCTAAAAGATTGTTTAGTCCG

GATAAGTGCCTGGAACTCGGCTCTTTGAAGTTGGAATTGCTAGTAATCGT

CTATCATCATGAGACGGTGAATCTTTTATCTGTGATGTACTAACTACTCG

TCAAGCGCGGAAATTTTTAAGAAATTCAAGTTCTTACGTCCATTTCTTG

GAGATCTGTGCTAAGTCGAAATAAGGTAGCTGTAGGGGAACCCTGTAGCT

GAATAATTTGTGTTGTTTAAATCCCCCCCATCCTTGTG.
```

The reference sequence used to design primers and a probe for the quantification of the RNA transcripts of CYTochrome B (CYTB) is referenced in GENBANK® under the accession number AF074871.1 (SEQ ID NO: 3), which is:

```
                                    (SEQ ID NO: 3)
TATTTATGGAATTATGGTTCATTATCAGGACTGTGTTTAATTATACAGAT

TATTACGGGTGTGACTTTAGCTATGCATTATATACCTTCGATTGATTTAG

CTTTCTTGAGTGTTGAACATATTATGTGAGATGTAAATTATGGTTGGTTG

ATTCGTTATATTCATAGTAATACGGCTTCTTTTTTCTTTCTGTTTGTTTA

TATTCATATTGCTTGAGGTATCTATTATGGATCTTATCGAACTCCCAGAA

TTCTCGTTTGGTCTATTGGTGTAGTTATCTTCTTAATTATGATTGTTACT

GCTTTCTTGGGATATGTTCTGCCTTTTGGTCAAATGTCATTGTGGGAGC

GACTGTTATTACTAATTTGATGTCTGCTATACCTTGGATTGGTAATGATA

TTGTGAATTTTATTTGGGGTGGGTTCTCTGTTAATCATGCTACTCTGAAT

TGATTCTTCTCTTTACATTATTTATTGCCTTTTGTTTTATTGGCTTTAGT

TGTTGCTCATTTAATCTCTTTACATGTTCATGGAAGTAGTAATCCTCTGG

GTGTTACTGGTAATTCAGATCGTCTGCCTTTCCATCCCTATTTCTCATTT

AAAGATTTAGTTACTGTTTTTTATTTTTATTAGCTTTATCTTTCTTTGT

GTTTTATGCTCCTAATGTCTTGGGACATAGTGATAATTATATTATGGCTA

ATCCTATGGCTACTCCTCCAAGTATTGTTCCTGAATGGTATCTTTTACCT

TTCTATGCAATCTTGTGATCTATTTCGAATAAATTATTTGGAGTTGTGGC

TATGTTAGCTGCTATTCTTATTCTTTTTGTTTTACCTCTTGTGGATTTAT

CTTGAATTTGAGGTTCTGCTTTTAGACCTCTTAGTAAATTCTTTTTTTGG

ATCTTTGTCACTAATTTCTTCTTGTTAATGTTTGTGGGTTCACAACATGT

TGAAGAACCTTTTGTGACGCTTGGACAATATGCTACATTCTTCTATTTCT

TCTATTTCTTAGTTGTTATTCCTCTGGTGGGTATTATT.
```

The reference sequence used to design primers and a probe for the quantification of the RNA transcripts of the Beta TUBuline (BTUB) is referenced in GENBANK® under the accession number AF170964.1 (SEQ ID NO: 4), which is:

(SEQ ID NO: 4)

```
   1 ggcgcctctt tttggagcac cattagcggt gaacacggtc ttgatagcac tggcctgtaa
  61 gcaatattgt aatactgcag tgtgtttgca gaggtgatta gaaatgccta taaggcagca
 121 aaaaggcatt gaaaagactc caaagaagta taaagatgct ctgcaaacaa tctaaaaaca
 181 tgcagtaata ctgcatgttt gcagtacttt ttttccaaaa cttatatttt tcagctatca
 241 tggaacctct gatctccaac tcgaacggat gaatgtttat ttcaacgagg tttctacgga
 301 aaaatgttta tagaatgtca gacatttatt ttaataggca tctggtggga aatacgtgcc
 361 tcgtgcagta ctggttgatt tagagcccgg tacaatggat gcagtacgtt ctgggccatt
 421 tgggaacctg tttcgaccag ataatttttat ttttggtcaa tcaggtgcag gaaataactg
 481 ggcaaaaggg cattatacag agggagcgga attggtagat actgtgttag atgtagttcg
 541 tcgggaagcc gaagcatgtg attgcttgca aggattccag attacacatt cattaggtgg
 601 tggaacgggt gcaggcatgg gaactttgct aatttcgaaa attcgagagg aatatccgga
 661 tcggatgatg gcaacgtttt cagtggttcc ctcaccaaaa gtttccgata cagttgtaga
 721 gccatataat gcaacattat cagtgcatgt gtgttttttaa gccattttta gaatgtatat
 781 taatgaggag gggtagcaat tagttgaaaa ttccgatgaa acattctgta tcgacaatga
 841 agcattatat gatatttgta tgcgtacatt aaaattgccg gatccaggat atggtgattt
 901 gaatcatctt gtctcggcag taatgagtgg tattacaact tgtcttcgat ttcctggaca
 961 actcaactcg gatttgcgta aattggccgt taatatggtg ccgtttcctc gtttgcactt
1021 tttcatggtt gggtttgctc cattaacaag cagtaagatg ctttaaacgt attctgaaat
1081 ggctgattgt tattctgtct agagggatca cattcatttc ggtcattgac agttcctgaa
1141 ttgactcagc aaatgtttga tgcaaagaat atgatggcag catcggatcc gagacatggt
1201 cgctatttaa ctgttgcagc gattttccgc ggtactgttt ccatgaagga ggttgaagat
1261 caaatgcata atgttcagca gaagaactct tcatattttg ttgaatggat tccaaacaat
1321 gtgcaaaccg cgctatgttc tattccacca cgtggtctca aaatgtcatc aacgtttatt
1381 ggcaattcaa catctattca ggaactattt aaacgtgtag gcgaccaatt tgctgca.
```

The reference sequence used to design primers and a probe for the quantification of the RNA transcripts of HSP70 is referenced in GENBANK® under the accession number DQ987621.1 (SEQ ID NO: 5), which is:

(SEQ ID NO: 5)

```
  1 gacggaaatt cggggatcca gaagtgcaat cagatatgaa acattggcct tttaaagtta
 61 tagacaaagg tcagaagcct tatattcagg ttgaatataa agggatatt aaaacattta
121 cgccggagga gatttcatca atggtcctta caaaaatgaa ggaggtggca gaagcgtatc
181 ttgggactaa agtttccaat gccgttatca cggtcccagc atatttcaat gattcacagc
241 gacaggctac gaaagacgca ggattgattg caggattgaa tgttttacgt attatcaatg
301 aacctacagc agcagccatt gcatatggtc tagataagaa gacatcaaat gaaaagaatg
361 tgcttatttt tgatcttgga ggaggaactt ttgacgtatc gttattaact atcgaagagg
421 gaattttga agtcaaagca accgcaggcg atacccattt gggaggagaa gattttgaca
481 atcgtcttgt aaaccacttc attgctgaac gcaaacacaa gaaagatctt tcagggaatg
541 cacgatctct tcgtcggctt cgaacagcat gtgagcgtgc taaacggact ctttcatcat
601 caacacagac gagtatagaa attgattcct tatttgaagg aattgattta tatacttcta
661 ttactcgtgc tcgatttgaa gaactttgtc aaggtctttt tagggaaca atggaaccag
721 ttgagaaagt tcttcgtgat tctaaaattg ataaatcaag tgttcatgaa attgtattgg
```

-continued

```
781 ttggtggttc tacgcgtatt ccgcgtattc agaaattggt ttgtgatttt tttaatggaa 841 aagagccaaa tagaacgatc aatccagatg aggctgttgc ctatggtgcg gcagttcaag 901 ttgctattct ttcaggagac acatcggaac aaactcaaga catactcttg cttgatgtgg 961 cgcctctctc aatgggt.
```

The reference sequence used to design primers and a probe for the quantification of the RNA transcripts of COX1 is referenced in GENBANK® under the accession number JX499143.1, REGION: 16256 . . . 17836 (SEQ ID NO: 6), which is:

```
                                                      (SEQ ID NO: 6)
16256                                                          atgac 16261 atgatggttg ttttcaacaa atgctaagga tatcggagtc ttgtacttga tctttgcact 16321 tttttctgga atgttgggta cagcatattc agtattattg agaatggaat taacttcccc 16381 aggtgttcag tatttacagg gtgataatca attgtataat gtaattttaa cgagtcatgc 16441 gttgttaatg atattcttta tggttatgcc cggaatggta ggaggttttg gtaattggtt 16501 ggttccagta atgattggag caccagatat ggcctttcca agattaaata atatctcctt 16561 ctggttgtta ccgccttctc tgattctgtt aattgcttct tctcttctag aaggtggaag 16621 tggtacaggt tggacttttt atccaccttt gtccagttta caaagtcatt cctcaggtgc 16681 tgtcgatttg tctatcttta gtctacattt agcaggtatt agttctatgt gggagctat 16741 taattttatt actactgttc ttaatacttg agctcccggt atgactatgc ataaaattcc 16801 attgtttgta tggtctatct ttgttactgc tatactgttg ttattgtcct tgccagtctt 16861 agcaggaggt attactatgc tcttgacgga ttgaaatttt aatacttcct tctatgatgt 16921 cgcaggagga ggggatccta tcctttatca acatctcttc tggttcttcg gacatccaga 16981 agtttatatt ctgattattc caggatttgg tatcattagt catattattt ccactttctc 17041 tggaaaacca gtattcggtt atttaggtat ggtttatgct atgttgtcaa ttggtgtctt 17101 aggatttatt gtctggagtc atcatatgta ttcagtgggt ttagatgttg atacatgagc 17161 ttattttact gctgctacta tgattattgg tgtacctact ggtattaaaa tcttctcttg 17221 gattgctact atgtatggtg gtgtgattcg atttaataca cctatgctct tgctatcgg 17281 attccttttc cttttactg tgggaggatt aacgggtatt gtcttgtcta atgcttcttt 17341 agatgtggct ttacatgata cttattatgt tgtagctcat ttccattatg ttttatccat 17401 gggtgcagtc tttgctctct tagcagcttg gtatttctgg tctccaaaaa ttttaggatt 17461 gttctttgat gaaaaattag ggcatttgca tttctggact ctttttattg gagtgaattt 17521 aacttttatg cctatgcatt tcttgggatt acagggtatg cccagatgaa ttcctgatta 17581 tcctgatgct tttgctcagt ggaatcatat ctcaagttta ggtagtttga tttctgttgt
```

-continued

```
17641 tgctactgtt gtttttattt attctatttt tgatcaattg atctctaaat gattggtacc 17701 gatgaatcct tggtattctc ctgatttctt tgttagtcat acgaatttag aggattccaa 17761 agcttgttcc ttagaatggg cattgatttc accaccagct ttccatgctt atactagttt 17821 acctaaacaa gcttaa.
```

The reference sequence used to design primers and a probe for the quantification of the RNA transcripts of NAD1 is referenced in GENBANK® under the accession number JX499143.1, REGION: 29671 . . . 30672 (SEQ ID NO: 7), which is:

```
                                                                  (SEQ ID NO: 7)
29671                              atgttaaatt gtattcaagt gggtattgtt 29701 ttattacctg ttttgttaag tgtagctttt gtgacattag ctgaacgtaa agttatggga 29761 tcgattcaac gacgtgtggg tcctaatgtt gtgggttatt atggtttgtt acaacctgta 29821 gctgatgctt taaaattatt attaaaagaa actattattc ctatccattc gaataaagtg 29881 ttgttcttct taggaccttc tattgcatta gtctttgctt taatgggttg gggtattatt 29941 ccatggaatt caggtataac actttgggat tttgatttag gtattttatt tagtttagct 30001 atttcttctt taggtgtgta tggtatttta attgggggtt gggcttctaa ttccaaatat 30061 gctttattag gttccttgtg aagtactgct caattaatta gttatgaatt agtttaact 30121 tcgattgttt ttgttgttgt tctttatct ggttctttta attttactca cattattgaa 30181 gaacaaaaag ctatttggtt tgttttgcct ttatttcctc tgtttatttt gttctttatt 30241 ggtgcttag cagaaacgaa ttgagctcct tttgatttgc cagaagctga atccgaatta 30301 gttgctgggt ttatgactga gtattctgct gcgatctttg ttttcttctt cctagctgaa 30361 tatgctaata ttattcttat ctctactcta gctgctattt tcttcttagg aggttattta 30421 ttacctttcg agttgcattt cttgcctaat ggtttagatg ttctcgttca gggattactt 30481 tctggtttga ttttaggttt gaaagttgct gggattattt tcctctttgt ttgggtttga 30541 tctagcttcc ctagaatttg atatgatcaa ttgttagttc tatgttggac tgttctgtta 30601 cctttgcttt ttgcttggat ttttctggtt ttagctattc tttttctttt taattctttt 30661 attcatttct ag.
```

The reference sequence used to design primers and a probe for the quantification of the RNA transcripts of ATP9 is referenced in GENBANK® under the accession number JX499143.1, REGION: 20225 . . . 20449 (SEQ ID NO: 8), which is:

```
                                                                  (SEQ ID NO: 8)
20225    atgtta caagcagcta aagttattgg ttcagggtta gctacaattg gattagcagg 20281 ggctggtatc ggtatcggtt tagttttcgg taatttatta gtagcgacaa gtcgaaatcc 20341 ttcattgaaa ggacaactct tctcttatgc tatcttggga tttgctctag cagaagctac 20401 tggtcttttc tgtttgatga tggctttcct tctgctatat gcagcttaa.
``` qRT-PCR Amplification

For each sample, the expression of the mtLSU, the CYTB, the BTUB, the HSP70, the COX1, the NAD1 and the ATP9 genes were tested (quantification of RNA transcripts). All PCR reactions were performed on a LIGHTCYCLER® 480 instrument (ROCHE DIAGNOSTICS; 2, Avenue du Vercors; BP 59; 38242 MEYLAN CEDEX; FRANCE) in a final volume of 10 μL containing 0.2 μL of EXPRESS SuperScript® III Mix for One-Step qRT-PCR (INVITROGEN™ by LIFE TECHNOLOGIES™; 5791 Van Allen way; Carlsbad; Calif. 92008; U.S.A.), 1X EXPRESS SuperScript® III SuperMix Universal buffer (INVITROGEN™ by LIFE TECHNOLOGIES™; 5791 Van Allen way; Carlsbad; Calif. 92008; U.S.A.), with 0.3 μM of each primer, 0.1 μM of the probe and 2 μL of a 1:2 dilution of RNA. The reaction consisted of a reverse transcription step at 50° C. 15 min, followed by DNA polymerase activation at 95° C. 2 min and 45 cycles of 95° C. 15 s and 60° C. 30 s.

The mtLSU (RNA) target was:

```
                                              SEQ ID NO: 9
CACUGAAUAUCUCGAGGGAGUAUGAAAAUAUUUAUCUCAGAUAUUUAAUC

UCAAAAUAACUAUUUCUUAAAAUAAAUAAUCAGACUAUGUGCGAUAAGGU

AGAUAGUCGAAAGGGAAACAG.
```

The cDNA reverse-transcript of the mtLSU target was (fragment 861-981 from SEQ ID NO: 1):

```
                                             SEQ ID NO: 10
CACTGAATATCTCGAGGGAGTATGAAAATATTTATCTCAGATATTTAATC

TCAAAATAACTATTTCTTAAAATAAATAATCAGACTATGTGCGATAAGGT

AGATAGTCGAAAGGGAAACAG.
```

Primers and probe used for the detection of the targeted region of the mtLSU RNA were:

```
PjF1:
                                             (SEQ ID NO: 11)
5'-CACTGAATATCTCGAGGGAGTATGAA-3'

PjR1:
                                             (SEQ ID NO: 12)
5'-CTGTTTCCCTTTCGACTATCTACCTT-3'
and the PjSL probe:
                                             (SEQ ID NO: 13)
5'-TCGCACATAGTCTGATTAT-3'
under
TAQMAN ® format (FAM ™ in 5' and MGB ® in 3').

FAM ™ = 6-carboxy-fluorescein dye

MGB ® = Minor Groove Binder ® quencher

A mtSSU (RNA) target can be:
                                             SEQ ID NO: 14
GCAAUGAUGGAAGUCGGAGCUAAUCCCCUAAAAGAUUGUUUAGUCCGGA

UAAGUGCCUGGAACUCGGCUCUUUGAAGUUGGA.

The cDNA reverse-transcript of this mtSSU target
can be (fragment 1154-1235 from SEQ ID NO: 2):
                                             SEQ ID NO: 15
GCAATGATGGAAGTCGGAGCTAATCCCCTAAAAGATTGTTTAGTCCGGAT

AAGTGCCTGGAACTCGGCTCTTTGAAGTTGGA.
```

Primers and probe for the detection of this mtSSU RNA target region can be:

Pj1154F: 5'-GCAATGATGGAAGTCGGAGC-3' (SEQ ID NO: 16),

Pj1235R: 5'-TCCAACTTCAAAGAGCCGAGT-3' (SEQ ID NO: 17), and the Pj1190P probe: 5'-TGTTTAGTCCGGATAAGTGCCTGGA-3' (SEQ ID NO: 18) under TAQMAN® format (FAM™ in 5' and BHQ-1® in 3').

BHQ-1®=Black Hole Quencher®-1.

Another mtSSU (RNA) target can be:

```
                                             SEQ ID NO: 19
GGAUGCAAUGAUGGAAGUCGGAGCUAAUCCCCUAAAAGAUUGUUUAGUCC

GGAUAAGUGCCUGGAACUCGGCUCUUUGAAGUUGGAAUUGCU.
```

The cDNA reverse-transcript of this mtSSU target can be (fragment 1150-1241 from SEQ ID NO: 2):

```
                                             SEQ ID NO: 20
GGATGCAATGATGGAAGTCGGAGCTAATCCCCTAAAAGATTGTTTAGT

CCGGATAAGTGCCTGGAACTCGGCTCTTTGAAGTTGGAATTGCT.
```

Primers and probe for the detection of this mtSSU RNA target region can be:

```
Pj1150F:
                                             (SEQ ID NO: 21)
5'-GGATGCAATGATGGAAGTCGGA-3',

Pj1241R:
                                             (SEQ ID NO: 22)
5'-AGCAATTCCAACTTCAAAGAGCC-3',
and the Pj1190P probe:
                                             (SEQ ID NO: 23)
5'-TGTTTAGTCCGGATAAGTGCCTGGAAC-3'.
under TAQMAN ® format (FAM ™ in 5' and
BHQ-1 ® in 3')
```

Still another mtSSU (RNA) target can be:

```
                                             SEQ ID NO: 24
UCAUGACCCUUAUGAAGUGGGCUACAGACGUGCUGCAAAAUUUUCUACA

AUGGGAUGCAAUGAUGGAAGUCGGAGC.
```

The cDNA reverse-transcript of this mtSSU target can be (fragment 1098-1173 from SEQ ID NO: 2):

```
                                             SEQ ID NO: 25
TCATGACCCTTATGAAGTGGGCTACAGACGTGCTGCAAAATTTTCTACAA

TGGGATGCAATGATGGAAGTCGGAGC.
```

Primers and probe for the detection of this mtSSU RNA target region can be:

```
Pj1098F:
                                             (SEQ ID NO: 26)
5'-TCATGACCCTTATGAAGTGGGC-3',

Pj1173R:
                                             (SEQ ID NO: 27)
5'-GCTCCGACTTCCATCATTGC-3',
``` and the Pj1125P probe:
(SEQ ID NO: 28)
5'-ACGTGCTGCAAAATTTTCTACAATGGG-3'.
under TAQMAN ® format (FAM ™ in 5' and
BHQ ® in 3')

The CYTB (RNA) target was:

(SEQ ID NO: 29)
CUCCCAGAAUUCUCGUUUGGUCUAUUGGUGUAGUUAUCUUCUUAAUU

AUGAUUGUUACUGCUUUCUUGGGAUAUGUUCUGCCUUUUGGUCAAAUG

UCAUUGUGGG.

The cDNA reverse-transcript of the CYTB target was (fragment 242-346 from SEQ ID NO: 3):

(SEQ ID NO: 30)
CTCCCAGAATTCTCGTTTGGTCTATTGGTGTAGTTATCTTCTTAATTAT

GATTGTTACTGCTTTCTTGGGATATGTTCTGCCTTTTGGTCAAATGTCA

TTGTGGG.

Primers and probe used for the detection of the targeted region of the CYTB RNA were:

CYTB_Pj242F:
(SEQ ID NO: 31)
5'-CTCCCAGAATTCTCGTTTGG-3'

CYTB_Pj346R:
(SEQ ID NO: 32)
5'-CCCACAATGACATTTGACCA-3'
and the CYTB_Pj301P probe:
(SEQ ID NO: 33)
5'-CTTTCTTGGGATATGTTCTGCC-3'.
under TAQMAN ® format (FAM ™ in 5' and
TAMRA ™ in 3')

TAMRA ™ = carboxytetramethylrhodamine fluorescent dye.

Primers and probe used for the detection of BTUB RNA were:

BTUB_Pj766F:
(SEQ ID NO: 34)
5'-CCATTAACAAGCAAGGGATCAC-3'

BTUB_Pj861R:
(SEQ ID NO: 35)
5'-CGATGCTGCCATCATATTCTT-3'
and the BTUB_Pj795P probe:
(SEQ ID NO: 36)
5'-TCGGTCATTGACAGTTCCTGAA-3'.
under TAQMAN ® format (FAM ™ in 5' and
TAMRA ™ in 3')

Primers and probe used for the detection of HSP70 RNA were:

HSP70_Pj126F:
(SEQ ID NO: 37)
5'-GGAGATTTCATCAATGGTCCTT-3'

HSP70_Pj202R
(SEQ ID NO: 38)
(5'-CGGCATTGGAAACTTTAGTCC-3'
and the HSP70_Pj157P probe:
(SEQ ID NO: 39)
5'-AAGGAGGTGGCAGAAGCGTA-3'.
under TAQMAN ® format (FAM ™ in 5' and
TAMRA ™ in 3')

An aliquot of a sample with a defined quantification was used in each PCR to be run as an internal control and to measure reproducibility. For mtLSU, CYTB, BTUB and HSP70, the Cq values±SD were 24.1±0.3, 23.6±0.3, 32.5±0.3, 29.0±0.2, respectively.

Primers and probe used for the detection of COX1 RNA were:

COX1_Pj228F:
(SEQ ID NO: 40)
5'-AGGTTTTGGTAATTGGTTGGTTCC-3'

COX1_Pj324R:
(SEQ ID NO: 41)
5'-AGAAGGCGGTAACAACCAGAA-3'
and the COX1_Pj261P probe:
(SEQ ID NO: 42)
5'-TGGAGCACCAGATATGGCCTTTCCAAGA-3';.
under TAQMAN ® format (FAM ™ in 5' and
BHQ-1 ™ in 3')

BHQ-1 ™ = Black Hole Quencher ®-1.

Primers and probe used for the detection of NAD1 RNA were:

NAD1_Pj579F:
(SEQ ID NO: 43)
5'-AGCAGAAACGAATTGAGCTCCT-3'

NAD1_Pj664R:
(SEQ ID NO: 44)
5'-TCGCAGCAGAATACTCAGTCAT-3'
and the NAD1_Pj608P probe:
(SEQ ID NO: 45)
5'-TGCCAGAAGCTGAATCCGAATTAGTTGC-3'.
under TAQMAN ® format (FAM ™ in 5' and
BHQ-1 ™ in 3')

Primers and probe used for the detection of ATPS RNA were:

ATP9_Pj25F:
(SEQ ID NO: 46)
5'-GGTTCAGGGTTAGCTACAATTGGA-3'

```
ATP9_Pj118R:
                                    (SEQ ID NO: 47)
5'-AAGGATTTCGACTTGTCGCTACT-3'
and the ATP9_Pj52P probe:
                                    (SEQ ID NO: 48)
5'-GCAGGGGCTGGTATCGGTATCGGTTTAG-3'.
under TAQMAN ® format (FAM ™ in 5' and
BHQ-1 ™ in 3')
```

Gene Expression Determination

For determination of the gene expression level of the different samples, all quantification data (Cq) were normalized compared to the BTUB expression. Experimental calibration curves allowed determination of the PCR efficiency (e) that was required to determine gene expression for each PCR. At the end, the expression of CYTB was compared to that of mtLSU gene without taking into account BTUB expression with modification of the formula of Pfaffl 2001 as:

$$\text{CYTB/mtLSU ratio} = E(\text{CYTB})^{-Cq(CYTB)}/E(\text{mtLSU})^{-Cq(mtLSU)}$$

The real-time PCR efficiency (E) of one cycle in the exponential phase was calculated according to the formula $E=10^{[-1/slope]}$ as described in Pfaffl 2001. The real-time PCR efficiency values for CYTB, mtLSU, BTUB and HSP70 are reported in Table 8.

Data Analysis

Correlation with clinical data was performed only with one sample per patient. Statistical analyses were performed with PRISM® v5.0 (GraphPAD Software Inc.; 7825 Fay Avenue; Suite 230; LA JOLLA; Calif. 92037, U.S.A.).

Results

Detection of RNA in BALF

From all 200 samples, mtLSU RNA PCR was compared to the mtLSU DNA PCR performed as a routine test. From the 200 samples, 34 (17%) were both positive and 148 (74%) were both negative with RNA and DNA PCR; cf. Table 2 below.

TABLE 2

Distribution of the number of samples regarding DNA and RNA mtLSU PCR

| Number of samples | Positive RNA mtLSU PCR | Negative RNA mtLSU PCR | Total |
|---|---|---|---|
| Positive DNA mtLSU PCR | 34 | 5 | 39 |
| Negative DNA mtLSU PCR | 13 | 148 | 161 |
| Total | 47 | 153 | 200 |

In 5 (2.5%) samples, mtLSU DNA but not RNA was detected, whereas in 13 samples, mtLSU RNA was detected but not DNA (cf. Table 2 above). RNA detection (n=47) is more sensitive than DNA detection (n=39) in BALF.

In addition, the fungal load was significantly higher with RNA than with DNA detection (FIG. 1, paired t-test: p<0.0001). RNA detection gave a 10 fold higher detection than DNA with a mean ΔCq (DNA-RNA) at 3.577 (95% confidence interval: 2.681-4.473).

In the 47 samples positive for mtLSU rRNA, CYTB, BTUB and HSP70 mRNA were detected in 31 (66%), 32 (68%) and 32 (68%) samples, respectively.

Clinical Probability of PCP Classification

From the 200 BALF prospectively collected from 192 patients, 2 samples (2 patients) harboring a positive DNA PCR were excluded because of lack of clinical data.

At the end, a total of 49 patients (50 samples) with either RNA or DNA detection were investigated for classification. Eighteen patients were considered as PCP (proven PCP in 14 patients, probable PCP in 1 patient and possible PCP in 3 patients) and 31 patients as no PCP.

No difference in the repartition of the different groups of disease was observed in patients with and without PCP (chi-2, p=0.063, cf. Table 3 below).

TABLE 3

Distribution of the PCP and no PCP patients according to different groups of diseases

| Background | PCP | no PCP | p |
|---|---|---|---|
| Hematological malignancies | 7 | 13 | 0.063 |
| HIV positive | 8 | 4 | |
| SOT | 1 | 2 | |
| others | 2 | 5 | |
| No ID | 0 | 7 | |
| Total | 18 | 31 | |

Figures 2A, 2B:
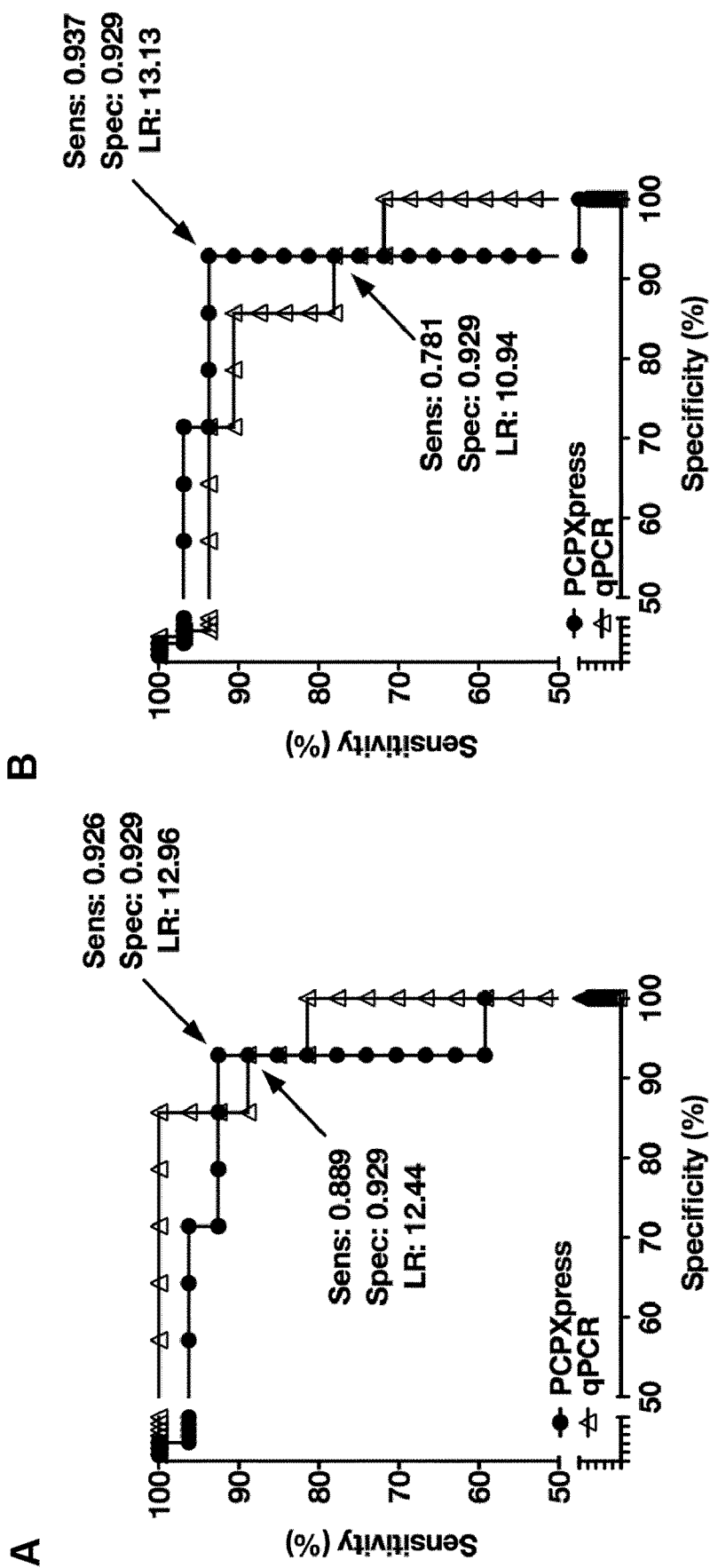
FIGS. 2A and 2B: ROC curves of mtLSU RNA qPCR (qPCR) and the CYTB/mtLSU ratio (PCP Xpress) tests for diagnostic (A, n=41) or diagnostic and follow-up (B, n=46) samples. Sens, sensitivity; Spec, Specificity; LR, Likelihood ratio.
Figures 3A, 3B:
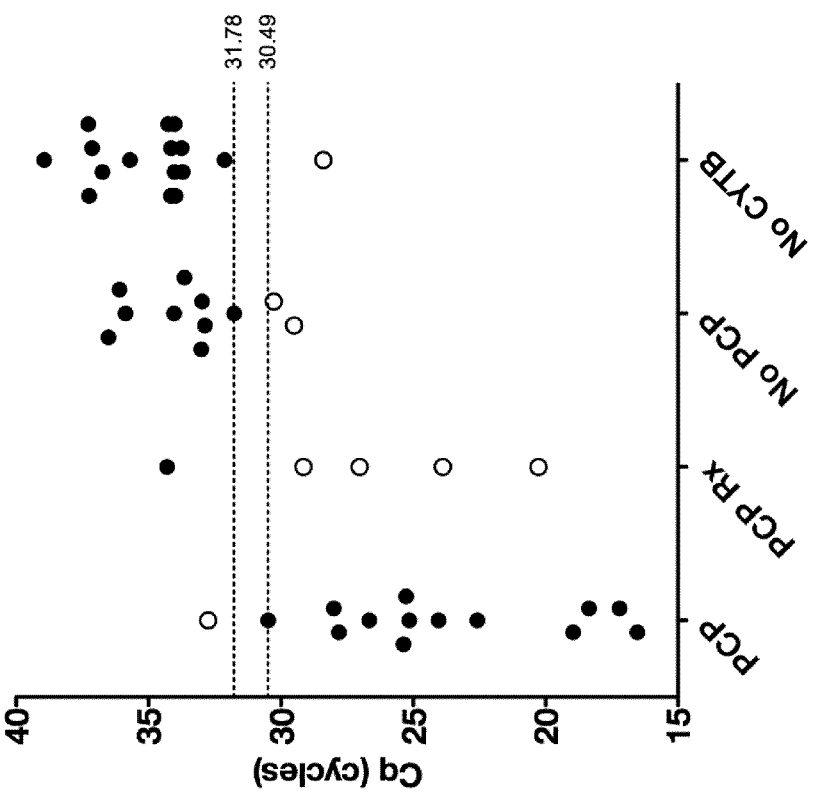
FIG. 3A. Plot of the mtLSU RNA quantification cycle (Cq) for each mtLSU positive samples in the different categories of samples. The range of threshold that allows the higher likelihood ratio is depicted as a dotted line ]30.49 to 31.78[. Cleared dots are from patients classified in a category but for which the ratio is in favor of the other group of patient.
FIG. 3B. Plots of the values of the CYTB/mtLSU ratio for each category of patients in samples in which both CYTB and mtLSU RNAs were amplified. PCP samples harbored mostly a CYTB/mtLSU<1.27, whereas non-PCP samples (carriers) or patients treated for a minimum of 15 days (PCP Rx) harbored mostly a CYTB/mtLSU ratio>1.66. Sixteen samples had CYTB unamplified so that the ratio was no calculated. Those samples were from patients without PCP. The range of threshold that allows the higher likelihood ratio is depicted as a dotted line ]1.27 to 1.66[. Cleared dots are from patients classified in a category but for which the ratio is in favor of the other group of patients.

In the PCP patients, 14 samples (14 patients) were diagnostic samples and 5 samples (4 patients) were not performed as diagnostic samples but to search for other etiology of a persistent or recently acquired pneumonia after PCP diagnosis and more than 15 days of cotrimoxazole treatment (analyzed apart for the others specimens and called follow-up samples). Patients with PCP were composed of hematological malignancies (7/14, 50%), HIV patients (8/14, 57%), solid organ transplant (SOT) (1/14, 7%) and other background (2/14, 14%). Immunofluorescence was positive in 8/14 (57%) patients and negative in 6/14 (43%) patients. Based on immunofluorescence results, sensitivity and specificity were 0.57 (95% CI, 0.289-0.823) and 1.00 (95% CI, 0.888-1.000), respectively. The ROC curve analysis of the quantification results (mtLSU RNA PCR) allowed determination of the best quantification cycle (Cq) threshold between 30.49 and 31.78 (FIGS. 2A and 3B). Based on the quantification results, optimal sensitivity and specificity were 0.812 (95% CI, 0.543-0.959) and 0.960 (95% CI, 0.796-0.999) for diagnostic samples (n=41, FIG. 2A and Table 7) and 0.650 (94% CI 0.408-0.846) and 0.961 (95% CI, 0.804-0.999) for diagnostic and follow-up samples (n=46, FIG. 2B and Table 7).

Variable CYTB/mtLSU Ratio in Different Categories of Patients

No PCP patient was recorded in the 16 samples with positive mtLSU RNA and negative CYTB RNA PCR and in the 152 samples with negative mtLSU and CYTB RNA PCR (cf. Table 6 below).

TABLE 6

Repartition of the samples in the different categories of samples regarding the expression of CYTB and mtLSU

| | Clinical classification | | |
|---|---|---|---|
| Categories of samples | PCP | PCP w Rx 15 days | no PCP |
| CYTB/mtLSU >1.66 | 1 | 5 | 9 |
| CYTB/mtLSU <1.27 | 13 | 0 | 2 |

TABLE 6-continued

Repartition of the samples in the different categories of samples regarding the expression of CYTB and mtLSU

| Categories of samples | Clinical classification | | |
|---|---|---|---|
| | PCP | PCP w Rx 15 days | no PCP |
| No CYTB | 0 | 0 | 16 |
| No CYTB/No mtLSU | 0 | 0 | 152 |

The ROC curve analysis of the CYTB/mtLSU ratios was performed and showed that a threshold between 1.27 and 1.66 allowed the higher likelihood ratio (LR: 12.96) (cf. Table 4 below, cf. FIGS. 2A and 3B).

TABLE 4

ROC curve data of the PCP Xpress test based on diagnostic samples (n = 41)

| Cutoff CYTB/mtLSU ratio | Sensitivity % | 95% CI | Specificity % | 95% CI | Likelihood ratio |
|---|---|---|---|---|---|
| −156.9 | 100.0 | 87.23 to 100.0 | 7.143 | 0.1807 to 33.87 | 1.08 |
| −3.985 | 100.0 | 87.23 to 100.0 | 14.29 | 1.779 to 42.81 | 1.17 |
| −2.864 | 96.30 | 81.03 to 99.91 | 14.29 | 1.779 to 42.81 | 1.12 |
| −2.386 | 96.30 | 81.03 to 99.91 | 21.43 | 4.658 to 50.80 | 1.23 |
| −2.191 | 96.30 | 81.03 to 99.91 | 28.57 | 8.389 to 58.10 | 1.35 |
| −1.992 | 96.30 | 81.03 to 99.91 | 35.71 | 12.76 to 64.86 | 1.50 |
| −1.926 | 96.30 | 81.03 to 99.91 | 42.86 | 17.66 to 71.14 | 1.69 |
| −1.903 | 96.30 | 81.03 to 99.91 | 50.00 | 23.04 to 76.96 | 1.93 |
| −1.763 | 92.59 | 75.71 to 99.09 | 50.00 | 23.04 to 76.96 | 1.85 |
| −1.546 | 92.59 | 75.71 to 99.09 | 57.14 | 28.86 to 82.34 | 2.16 |
| −1.398 | 92.59 | 75.71 to 99.09 | 64.29 | 35.14 to 87.24 | 2.59 |
| −1.279 | 92.59 | 75.71 to 99.09 | 71.43 | 41.90 to 91.61 | 3.24 |
| −1.222 | 92.59 | 75.71 to 99.09 | 78.57 | 49.20 to 95.34 | 4.32 |
| 0.02900 | 92.59 | 75.71 to 99.09 | 85.71 | 57.19 to 98.22 | 6.48 |
| 1.472 | 92.59 | 75.71 to 99.09 | 92.86 | 66.13 to 99.82 | 12.96 |
| 1.909 | 88.89 | 70.84 to 97.65 | 92.86 | 66.13 to 99.82 | 12.44 |
| 2.544 | 85.19 | 66.27 to 95.81 | 92.86 | 66.13 to 99.82 | 11.93 |
| 3.959 | 81.48 | 61.92 to 93.70 | 92.86 | 66.13 to 99.82 | 11.41 |
| 5.402 | 77.78 | 57.74 to 91.38 | 92.86 | 66.13 to 99.82 | 10.89 |
| 6.060 | 74.07 | 53.71 to 88.89 | 92.86 | 66.13 to 99.82 | 10.37 |
| 8.202 | 70.37 | 49.82 to 86.25 | 92.86 | 66.13 to 99.82 | 9.85 |
| 10.11 | 66.67 | 46.04 to 83.48 | 92.86 | 66.13 to 99.82 | 9.33 |
| 10.96 | 62.96 | 42.37 to 80.60 | 92.86 | 66.13 to 99.82 | 8.81 |
| 14.93 | 59.26 | 38.80 to 77.61 | 92.86 | 66.13 to 99.82 | 8.30 |
| 59.02 | 59.26 | 38.80 to 77.61 | 100.0 | 76.84 to 100.0 | |

After addition of the 5 follow-up samples, a ratio between the same range allowed the higher likelihood ratio (LR: 13.13) (cf. Table 5 below, cf. FIGS. 2B and 3B).

TABLE 5

ROC curve data of the PCP Xpress test based on diagnostic (n = 41) and follow up (n = 5) samples

| Cutoff CYTB/mtLSU ratio | Sensitivity % | 95% CI | Specificity % | 95% CI | Likelihood ratio |
|---|---|---|---|---|---|
| 0.1085 | 100.0 | 89.11 to 100.0 | 7.143 | 0.1807 to 33.87 | 1.08 |
| 0.2585 | 100.0 | 89.11 to 100.0 | 14.29 | 1.779 to 42.81 | 1.17 |
| 0.3570 | 100.0 | 89.11 to 100.0 | 21.43 | 4.658 to 50.80 | 1.27 |
| 0.4190 | 96.88 | 83.78 to 99.92 | 21.43 | 4.658 to 50.80 | 1.23 |
| 0.4585 | 96.88 | 83.78 to 99.92 | 28.57 | 8.389 to 58.10 | 1.36 |
| 0.5025 | 96.88 | 83.78 to 99.92 | 35.71 | 12.76 to 64.86 | 1.51 |
| 0.5195 | 96.88 | 83.78 to 99.92 | 42.86 | 17.66 to 71.14 | 1.70 |
| 0.5260 | 96.88 | 83.78 to 99.92 | 50.00 | 23.04 to 76.96 | 1.94 |
| 0.5705 | 96.88 | 83.78 to 99.92 | 57.14 | 28.86 to 82.34 | 2.26 |
| 0.6490 | 96.88 | 83.78 to 99.92 | 64.29 | 35.14 to 87.24 | 2.71 |
| 0.7170 | 96.88 | 83.78 to 99.92 | 71.43 | 41.90 to 91.61 | 3.39 |
| 0.7835 | 93.75 | 79.19 to 99.23 | 71.43 | 41.90 to 91.61 | 3.28 |
| 0.8185 | 93.75 | 79.19 to 99.23 | 78.57 | 49.20 to 95.34 | 4.38 |
| 1.050 | 93.75 | 79.19 to 99.23 | 85.71 | 57.19 to 98.22 | 6.56 |
| 1.473 | 93.75 | 79.19 to 99.23 | 92.86 | 66.13 to 99.82 | 13.13 |
| 1.745 | 90.63 | 74.98 to 98.02 | 92.86 | 66.13 to 99.82 | 12.69 |
| 1.989 | 87.50 | 71.00 to 96.49 | 92.86 | 66.13 to 99.82 | 12.25 |
| 2.545 | 84.38 | 67.21 to 94.72 | 92.86 | 66.13 to 99.82 | 11.81 |
| 3.025 | 81.25 | 63.56 to 92.79 | 92.86 | 66.13 to 99.82 | 11.38 |
| 3.412 | 78.13 | 60.03 to 90.72 | 92.86 | 66.13 to 99.82 | 10.94 |
| 4.347 | 75.00 | 56.59 to 88.54 | 92.86 | 66.13 to 99.82 | 10.50 |
| 5.402 | 71.88 | 53.25 to 86.25 | 92.86 | 66.13 to 99.82 | 10.06 |
| 6.060 | 68.75 | 49.99 to 83.88 | 92.86 | 66.13 to 99.82 | 9.63 |
| 7.766 | 65.63 | 46.81 to 81.43 | 92.86 | 66.13 to 99.82 | 9.19 |
| 9.669 | 62.50 | 43.69 to 78.90 | 92.86 | 66.13 to 99.82 | 8.75 |
| 10.11 | 59.38 | 40.64 to 76.30 | 92.86 | 66.13 to 99.82 | 8.31 |
| 10.79 | 56.25 | 37.66 to 73.64 | 92.86 | 66.13 to 99.82 | 7.88 |
| 11.64 | 53.13 | 34.74 to 70.91 | 92.86 | 66.13 to 99.82 | 7.44 |
| 14.93 | 50.00 | 31.89 to 68.11 | 92.86 | 66.13 to 99.82 | 7.00 |
| 59.02 | 50.00 | 31.89 to 68.11 | 100.0 | 76.84 to 100.0 | |

Without treatment, all IF positive samples had a ratio <1.27. After 15 days of cotrimoxazole in patients that had an IF-positive sample, CYTB and mtLSU could be amplified and the ratio was >1.66. In IF negative samples, ratio <1.27 and >1.66 were observed corresponding to patient with PCP but with negative IF or to colonized patients.

After clinical classification, samples from PCP patients had mostly a ratio <1.27 (13/14, 92.9%) whereas those from patients treated with cotrimoxazole >15 days (5/5, 100%) and those from patients without PCP had mostly a ratio >1.66 (9/11, 81.9%) (cf. Table 6 above, cf. FIG. 3B).

Performance of the PCP Xpress Test

The diagnostic performances of our test were then calculated based on different categories of samples. Taking into account the samples for which a ratio is determinable (positive CYTB and mtLSU RNA PCR, n=25), with a CYTB/mtLSU ratio threshold at 1.5 (threshold between ]1.27 to 1.66[), sensitivity, specificity, Positive predictive value (PPV) and negative predictive value (NPV) and the likelihood ratio (LR) were 0.867, 0.900, 0.929, 0.818, 8.667 (cf. Table 7 below).

TABLE 7

Sensitivity, specificity, positive predictive and negative predictive values, likelihood ratio of the PCP Xpress and RNA mtLSU qPCR test in diagnostic and diagnostic and follow-up samples

| | Samples | | | | | | | |
|---|---|---|---|---|---|---|---|---|
| | Diagnostic and CYTB and mtLSU positive (n = 25) | | Diagnostic and Follow up CYTB and mtLSU positive (n = 30) | | Diagnostic and mtLSU positive (n = 41) | | Diagnostic and follow up and mtLSU positive (n = 46) | |
| Test used | PCP Xpress | RNA qPCR | PCP Xpress | RNA qPCR | PCP Xpress | RNA qPCR | PCP Xpress | RNA qPCR |
| Sensitivity | 0.8667 | 0.8667 | 0.8667 | 0.6842 | 0.8667 | 0.8125 | 0.8667 | 0.6500 |
| [95% CI] | [0.5954 to 0.9834] | [0.5954 to 0.9834] | [0.5954 to 0.9834] | [0.4345 to 0.8742] | [0.5954 to 0.9834] | [0.5435 to 0.9595] | [0.5954 to 0.9834] | [0.4078 to 0.8461] |
| Specificity | 0.9000 | 0.9000 | 0.9333 | 0.9091 | 0.9615 | 0.9600 | 0.9677 | 0.9615 |
| [95% CI] | [0.5550 to 0.9975] | [0.5550 to 0.9975] | [0.6805 to 0.9983] | [0.5872 to 0.9977] | [0.8036 to 0.9990] | [0.7965 to 0.9990] | [0.8330 to 0.9992] | [0.8036 to 0.9990] |
| Positive Predictive Value [95% CI] | 0.9286 [0.6613 to 0.9982] | 0.9286 [0.6613 to 0.9982] | 0.9286 [0.6613 to 0.9982] | 0.9286 [0.6613 to 0.9982] | 0.9286 [0.6613 to 0.9982] | 0.9286 [0.6613 to 0.9982] | 0.9286 [0.6613 to 0.9982] | 0.9286 [0.6613 to 0.9982] |
| Negative Predictive Value [95% CI] | 0.8182 [0.4822 to 0.9772] | 0.8182 [0.4822 to 0.9772] | 0.8750 [0.6165 to 0.9845] | 0.6250 [0.3543 to 0.8480] | 0.9259 [0.7571 to 0.9909] | 0.8889 [0.7084 to 0.9765] | 0.9375 [0.7919 to 0.9923] | 0.7813 [0.6003 to 0.9072] |
| Likelihood Ratio | 8.667 | 8.667 | 13.00 | 7.526 | 22.53 | 20.31 | 26.87 | 16.90 |

| | Samples | | | |
|---|---|---|---|---|
| | All diagnostic samples (n = 193) | | All (n = 198) | |
| Test used | PCP Xpress | RNA qPCR | PCP Xpress | RNA qPCR |
| Sensitivity | 0.8667 | 0.8125 | 0.8667 | 0.6500 |
| [95% CI] | [0.5954 to 0.9834] | [0.5435 to 0.9595] | [0.5954 to 0.9834] | [0.4078 to 0.8461] |
| Specificity | 0.9944 | 0.9944 | 0.9945 | 0.9944 |
| [95% CI] | [0.9691 to 0.9999] | [0.9689 to 0.9999] | [0.9699 to 0.9999] | [0.9691 to 0.9999] |
| Positive Predictive Value [95% CI] | 0.9286 [0.6613 to 0.9982] | 0.9286 [0.6613 to 0.9982] | 0.9286 [0.6613 to 0.9982] | 0.9286 [0.6613 to 0.9982] |
| Negative Predictive Value [95% CI] | 0.9888 [0.9602 to 0.9986] | 0.9832 [0.9518 to 0.9965] | 0.9891 [0.9613 to 0.9987] | 0.9620 [0.9232 to 0.9846] |
| Likelihood Ratio | 154.3 | 143.8 | 158.6 | 115.7 |

PCP Xpress: CYTB/mtLSU threshold between ]1.27 and 1.66[
qPCR RNA mtLSU: Cq threshold at ]30.49 and 31.78[

If the 16 samples with a negative CYTB expression were added with a CYTB/mtLSU ratio threshold at 1.5 (threshold between ]1.27 to 1.66[), sensitivity, specificity, PPV and NPV and LR were 0.867, 0.961, 0.929, 0.926, 22.53 (cf. Table 7 above). If all diagnostic samples were considered, with a threshold of CYTB/mtLSU ratio at 1.5 (threshold between ]1.27 to 1.66[), sensitivity, specificity, PPV and NPV and LR were 0.867, 0.994, 0.929, 0.989, 154.3 (cf. Table 7 above). If follow-up samples were included, in each category of samples, the likelihood ratio was higher than with diagnostic samples alone (cf. Table 7 above). Overall, likelihood ratios were higher (LR=158.6) with PCP Xpress than with mtLSU RNA quantification (cf. Table7 above).

Testing Gene Expression for Other Gene (HSP70, BTUB, COX1, NAD1, ATP9) Compared to mtLSU HSP70 gene was tested because its mRNA was one of the most abundant transcripts found in a transcriptome analysis of *Pneumocystis carinii* during a fulminate infection in a rat model of pneumocystosis. The BTUB gene was used as a reference gene and also tested in comparison to mtLSU. Other mitochondrial genes were also investigated: COX1, NAD1 and ATP9.

The BTUB and HSP70 gene expression were tested in all samples in parallel to CYTB and mtLSU. COX1, NAD1, and ATP9 were tested in 9 positive samples (4 recovered from PCP patients; and 5 recovered from patients without PCP). ATP9 was not enough expressed to be used as a diagnostic marker.

For each gene, the ratio compared to mtLSU was calculated as described above.

Figure 4:
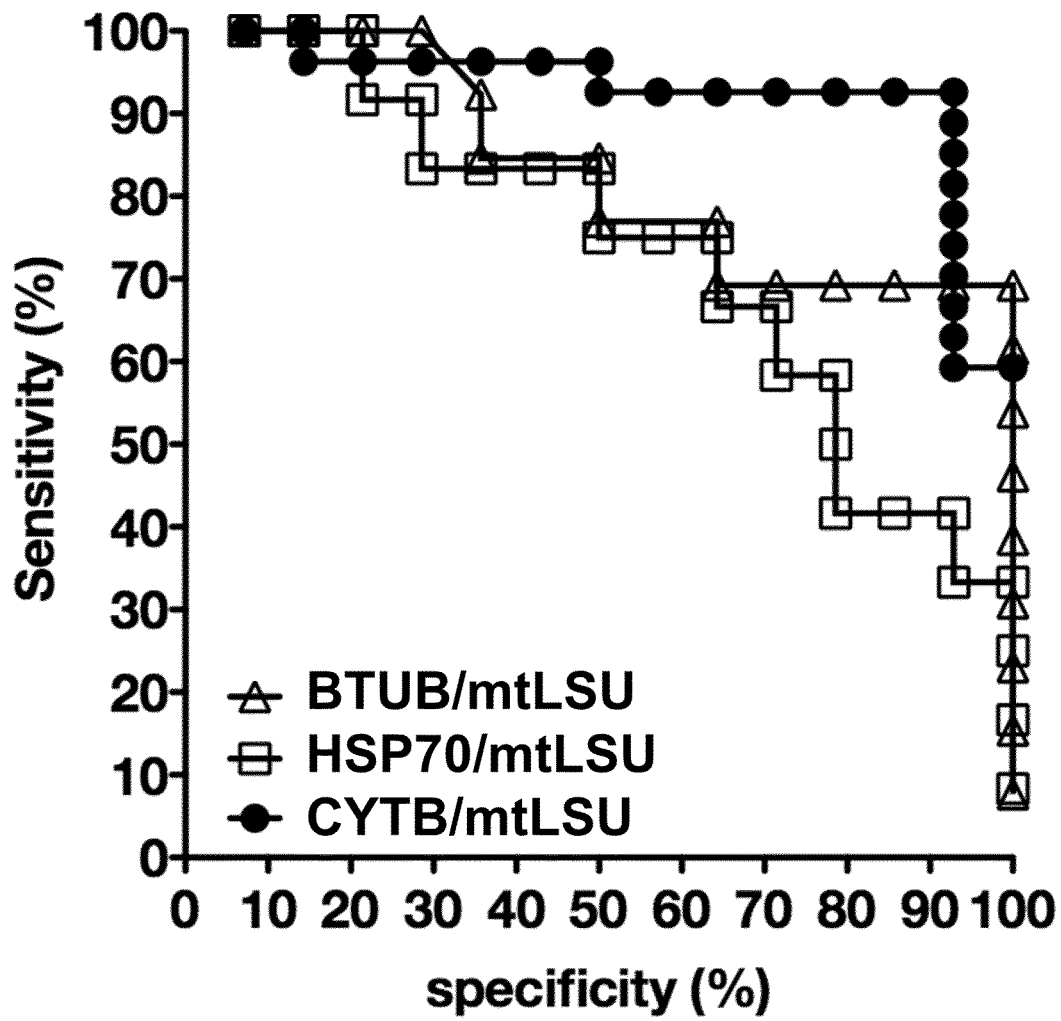
FIG. 4: ROC curve analysis for the BTUB, HSP70 and CYTB to mtLSU ratios. The higher likelihood ration was obtained with the CYTB/mtLSUratio.

The HSP70 and BTUB ratio in our study gave maximum likelihood ratios of 5.83 and 9.69, respectively. These values were lower than for CYTB (cf. FIG. 4). No other ratio (CYTB vs. BTUB, mtLSU vs. BTUB, HSP70 vs. BTUB, HSP70 vs. CYTB) gave accurate discrimination between PCP and non-PCP samples. In addition, it was not possible to see any differences in the COX1 and NAD1 ratios in PCP and non-PCP samples (cf. Table 8 below).

TABLE 8

Gene expression and ratio to mtLSU obtained for 9 samples (4 from PCP and 5 from non PCP patients) for the BTUB, HSP70, NAD1, COX1 and CYTB genes

| | Clinical classification | BTUB Cq | BTUB/ mtLSU ratio | HSP70 Cq | HSP70/ mtLSU ratio | NAD1 Cq | NAD1/ mtLSU ratio | COX1 Cq | COX1/ mtLSU ratio | CYTB Cq | CYTB/ mtLSU ratio | mtLSU Cq |
|---|---|---|---|---|---|---|---|---|---|---|---|---|
| PCR efficacy | | 1.975 | | 1.94 | | 2* | | 2* | | 1.973 | | 1.924 |
| Sample 17 | PCP | 23.145 | 0.01 | 21.69 | 0.03 | 17.555 | 0.26 | 17.56 | 0.26 | 16.885 | 0.52 | 16.545 |
| Sample 21 | PCP | 30.03 | 0.02 | 28.825 | 0.07 | 26.73 | 0.13 | 26.73 | 0.13 | 25.17 | 0.53 | 25.16 |
| Sample 30 | PCP | 28.82 | 0.01 | 23.155 | 0.57 | 24.68 | 0.10 | 24.68 | 0.10 | 23.505 | 0.30 | 22.585 |
| Sample 51 | PCP | 32.59 | 0.02 | 29.565 | 0.28 | 30.33 | 0.07 | 30.33 | 0.07 | 28.225 | 0.43 | 28.01 |
| Sample 6 | No PCP | 38.73 | 0.09 | 38.28 | 0.23 | 36.54 | 0.24 | 36.54 | 0.24 | 32.81 | 4.98 | 36.525 |
| Sample 9 | No PCP | no | na | 37.51 | 0.08 | 34.66 | 0.17 | 34.66 | 0.17 | 32.035 | 1.66 | 34.045 |
| Sample 16 | No PCP | 37.44 | 0.02 | 34.925 | 0.21 | 33.81 | 0.16 | 33.81 | 0.16 | 32.185 | 0.75 | 32.98 |
| Sample 27 | No PCP | 34.57 | 0.01 | 32.755 | 0.09 | 31.625 | 0.07 | 31.63 | 0.07 | 29.725 | 0.41 | 29.51 |
| Sample 57 | No PCP | 35.74 | 0.50 | no | na | 36.4 | 0.20 | 36.4 | 0.20 | 31.13 | 11.82 | 36.1 |

*PCR efficacy was not calculated for NAD1 and COX1 gene, and was therefore fixed at 2.
no = not detected
na = not applicable Example 2

Addition of an Internal Control as Control of RNA Extraction and/or Purification An artificial or exogenous RNA can be added to the sample prior to the extraction and/or purification step. Such an artificial or exogenous RNA is known as an Internal Extraction Control RNA (IECR).

IECR can be an artificial cell containing calibrated RNA. Following RNA extraction and in parallel to testing the target genes (CYTB and mtLSU), the presence and the quantity of the control IECR, will be tested upon addition in dedicated mix, and specific primers in a specific well. Signal derived from the Internal Control RNA confirms the success of the extraction step and is also used to determine the presence of inhibitors in the RNA sample. IECR contains a sequence that had no significant known homology to any published sequence and should not interfere with the detection of the sample RNA (human and fungi). A negative control reaction may also be performed.

Examples of IECR include:
- the RNA extraction control commercialized by BIOLINE (BIOLINE USA Inc.; 305 Constitution Dr.; TAUNTON; Mass. 027080; U.S.A.) under catalog number BIO-38040 or BIO-35040,
- the AMBION® ERCC RNA Spike-In Controls, which are commercialized by LIFE TECHNOLOGIES S.A.S. (route de l'orme des merisiers; Immeuble Discovery—Zone Technogique; 91190 SAINT AUBIN, FRANCE), under catalog number 4456740, and
- the RNA Internal Control, which is commercialized by QIAGEN® (QIAGEN® France S.A.S.; 3, avenue du Canada; LP 809; 91974 COURTABOEUF CEDEX ; FRANCE) under catalog number 211492.

Alternatively to the introduction of an artificial or exogenous RNA prior to the extraction and/or purification step, the control can be performed by detecting that a human gene is still present after said extraction and/or purification step. Examples of suitable human genes are known in the art and include constitutive genes, such as the human albumin (ALB) gene or the human TATA Box binding protein (TBP).

Said human gene can be detected using a probe, more particularly a primer pair and a (real-time) probe, which specifically detect said human gene.

Examples of primer pair and (real-time) probe for the human albumin (ALB) gene include

```
ALB_Hs_10F
                                    (SEQ ID NO: 49)
TCGTTACACCAAGAAAGTACCCC;

ALB_Hs_89R
                                    (SEQ ID NO: 50)
TGCTGCCCACTTTTCCTAGG;

ALB_Hs_34P
                                    (SEQ ID NO: 51)
AGTGTCAACTCCAACTCTTGTAGAGGT.
```

Examples of primer pair and (real-time) probe for the human TATA Box binding protein (TBP) include

```
TBP_Hs_107F
                                    (SEQ ID NO: 52)
TGGCGTGTGAAGATAACCCA;

TBP_Hs_204R
                                    (SEQ ID NO: 53)
CGCTGGAACTCGTCTCACTA;
and TBP_Hs_142P
                                    (SEQ ID NO: 54)
TGCTGAGAAGAGTGTGCTGGAGATGC;
or TBP_Hs_73F
                                    (SEQ ID NO: 55)
ATCTTTGCAGTGACCCAGCA;

TBP_Hs_169R
                                    (SEQ ID NO: 56)
GAGCATCTCCAGCACACTCT;
and TBP_Hs_93R
                                    (SEQ ID NO: 57)
GCATCACTGTTTCTTGGCGTGTGAAG.
```

Example 3

Alternate CYTB Probes and Primers

The CYTB (cDNA) probe that was used in Example 1 above was the probe of SEQ ID NO: 33 under TAQMAN® format, using the FAM™ fluorophore in 5' and the TAMRA™ quencher in 3'.

Alternatively to the TAMRA® quencher, a Black-Hole Quencher®-1 (BHQ®1) was successfully used. With this alternate quencher, the efficiency of the simplex RT-PCR was of 1.94.

The simplex RT-PCR efficiency was of 1.92 for mtLSU (primers and probe of SEQ ID NOs: 11-13 as described in Example 1).

The simplex RT-PCR efficiency was of 1.95 for mtSSU (primers and probe of SEQ ID NOs: 26-28 as described in Example 1).

Each simplex RT-PCR was performed as described in Example 1, i.e., on a LIGHTCYCLER® 480 instrument (ROCHE DIAGNOSTICS; 2, Avenue du Vercors; BP 59; 38242 MEYLAN CEDEX; FRANCE) in a final volume of 10 µL containing 0.2 µL of EXPRESS SuperScript® III Mix for One-Step qRT-PCR (INVITROGEN™ by LIFE TECHNOLOGIES™; 5791 Van Allen way; Carlsbad; Calif. 92008; U.S.A.), 1× EXPRESS SuperScript® III SuperMix Universal buffer (INVITROGEN™ by LIFE TECHNOLOGIES™; 5791 Van Allen way; Carlsbad; Calif. 92008; U.S.A.), with 0.3 µM of each primer, 0.1 µM of the probe and 2 µL of a 1:2 dilution of RNA. The reaction consisted of a reverse transcription step at 50° C. 15 min, followed by DNA polymerase activation at 95° C. 2 min and 45 cycles of 95° C. 15 s and 60° C. 30 s.

The nucleotide sequence of SEQ ID NO: 33 (CYTB cDNA probe) can be modified to replace at least one nucleotide by its Locked Nucleic Acid (LNA™) version (EXIQON™ Inc. 14 F Gill Street Woburn Mass. 01801 U.S.A.).

For example, at least one of the T, A and G nucleotides of the sequence of SEQ ID NO: 33 can be replaced by a LNA™-T, LNA™-A or LNA™-G, respectively.

For example, one to five nucleotides of the sequence of SEQ ID NO: 33 can (each) be replaced by their (respective) LNA™ version.

For example, one to five of the T, A and G nucleotides of the sequence of SEQ ID NO: 33 can (each) be replaced by their (respective) LNA™ counterpart, i.e., a LNA™-T, LNA™-A or LNA™-G, respectively.

For example, the nucleotide sequence of SEQ ID NO: 33 (CTT-TCT-TGG-GAT-ATG-TTC-TGC-C) can be modified into CT8-TCT-8GG-G5T-ATG-8TC-T7C-C, wherein 8=LNA™-T, 5=LNA™-A and 7=LNA™-G (SEQ ID NO: 58) [the sequence complementary to SEQ ID NO: 58 being G-G6A-GA5-CAT-A8C-CC5-AGA-SAG (SEQ ID NO: 59), wherein 8=LNA™-T, 5=LNA™-A, 7=LNA™-G and 6=LNA™-C].

Such LNA modifications are intended to increase the specificity of the nucleotide sequence (i.e., in the case of SEQ ID NO: 33 or the complementary sequence thereof, to increase the specificity of the CYTB cDNA probe).

The CYTB forward primer that was used in Example 1 above was the primer of sequence SEQ ID NO: 31. Alternatively, the nucleotide sequence of SEQ ID NO: 31 (CYTB_Pj242F: 5'-CTC-CCA-GAA-TTC-TCG-TTT-GG-3') can be modified into CTC-CCA-GAA-TTC-TMG-TTT-GG, wherein M=C or A (SEQ ID NO: 60) according to the IUPAC nucleotide code.

Such degenerated primer is intended to allow the detection and the quantification of CYTB mRNA in a sample from a patient having, in this genome, either a C or A at the position 255 of the nucleotide sequence SEQ ID NO: 3 corresponding to CYTB gene.

Example 4

Alternate Ratio (Ratio mtSSU/mtLSU)

Bronchoalveolar lavage (BAL) fluid samples of 18 patients were analyzed for detection and quantification of the RNA transcripts of mtSSU and mtLSU [twelve non-PCP patients that are *P. pneumonia* carriers; and six PCP patients, who did not receive any anti-PCP treatment or who have received an anti-PCP treatment for at most 15 days].

All samples were positive for both RNA transcripts (mtSSU and mtLSU).

mtLSU RT-PCR was performed as described in Example 1 above (with the mtLSU primers of SEQ ID NOs: 11-12 and the probe of SEQ ID NO: 13).

mtSSU RT-PCR was performed as described in Example 1 above (with the mtSSU primers of SEQ ID NOs: 26-27 and the probe of SEQ ID NO: 28).

Figure 5:
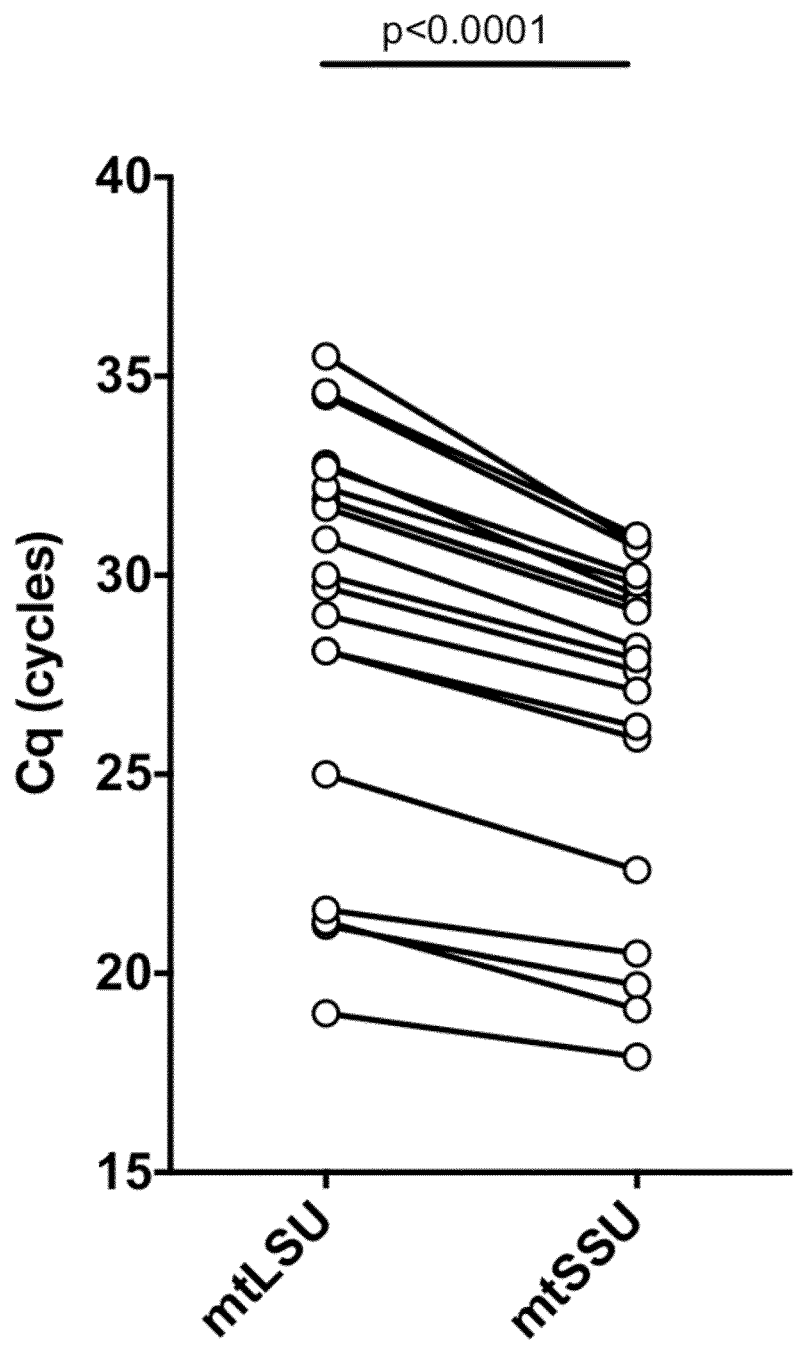
FIG. 5: mtLSU and mtSSU quantification in BAL fluid samples by PCR.

Quantification of mtSSU and of mtLSU:

mtSSU gene gives significantly better cycles results than mtLSU with a median of 27.90 [CI95% 24.39-28.55] compared to 30.00 [CI95% 26.51-31.36], respectively ($p<0.001$). Please see FIG. 5.

mtSSU/mtLSU Ratio:

The mtSSU/mtLSU RNA ratio allows discrimination between PCP and carriage (the optimal ratio being of 2.7).

A ratio from 3.1 to 3.3 would lead to 100% sensitivity but with a lower specificity (75% at 3.1 and 66.6% at 3.3). However, if the purpose were to allow PCP diagnosis together with identifying the patients with carriage, a ratio of 3.1 to 3.3 would be optimal to avoid misidentification of PCP patients who needs to be treated for PCP.

Figure 6:
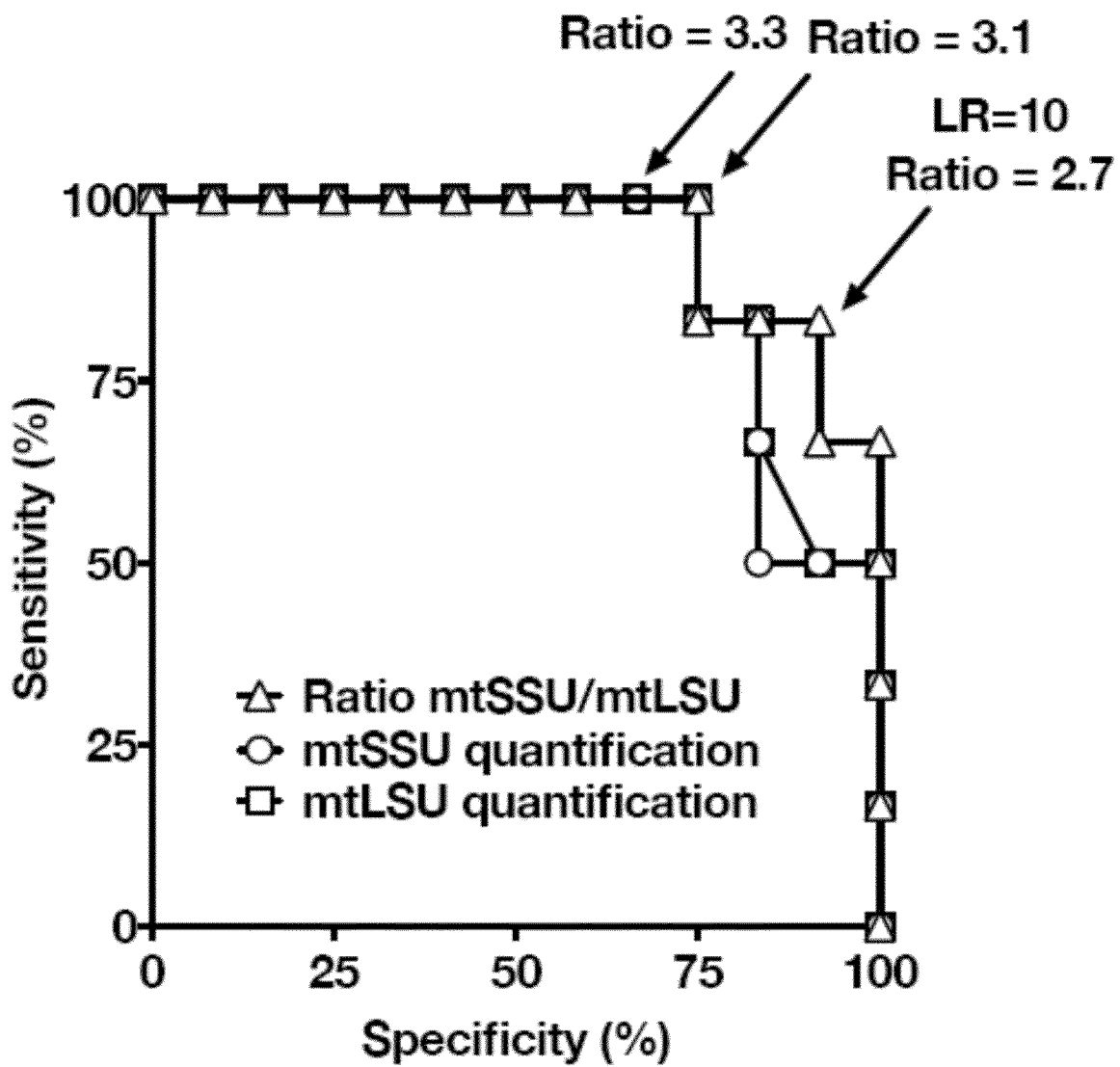
FIG. 6: analysis of the ROC curves obtained with the PCR (cycle) quantification of mtSSU and of mtLSU (in BAL fluid samples), and obtained with the mtSSU/mtLSU ratio. The maximal Likehood Ratio (LR) of the mtSSU/mtLSU ratio is at 10 (for an optimal ratio of 2.7) [whereas the maximal LR of each of mtLSU and mtSSU quantification alone is at 6]. A ratio of 3.1-3.3 would however allow to reach a sensitivity of 100%, and may appear preferable for accurate PCP detection.

The comparison of the ROC curves obtained with mtLSU or mtSSU quantification (Cycles) alone gave for both a maximal likelihood ratio at 6 for both. The mtSSU/mtLSU ratio gave the best result (likehood ratio at 10 for ratio of 2.7). Please see FIG. 6.

Figure 7:
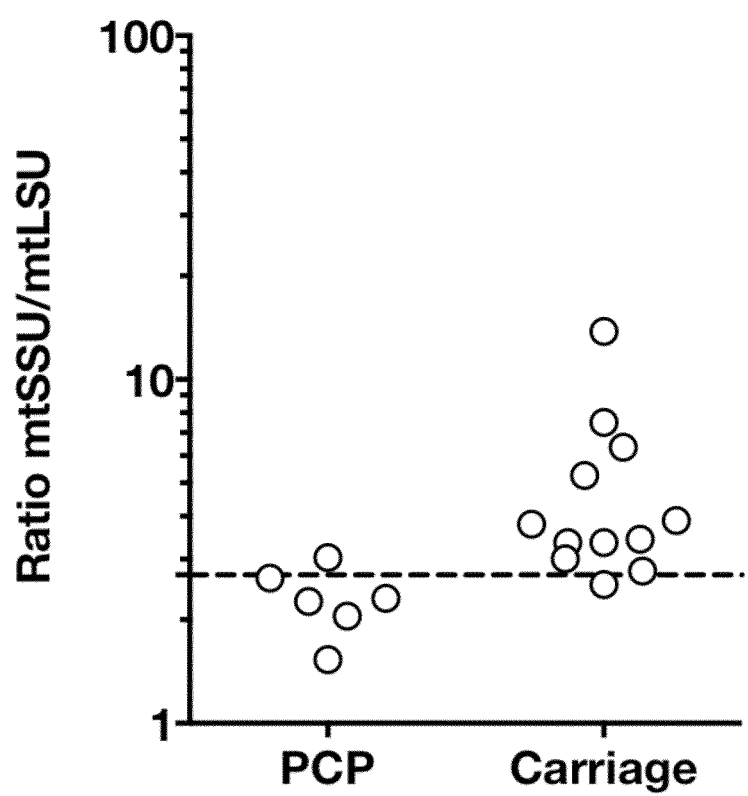
FIG. 7: distribution of the mtSSU/mtLSU ratio in the BAL fluid samples of PCP patients and of *P. jirovecii* carrier (but non-PCP) patients. The ratio of 2.7 is showed in dashed line.

FIG. 7 shows the distribution of the mtSSU/mtLSU RNA ratio values in the PCP patients and in the carrier patients.

Figures 8A, 8B:
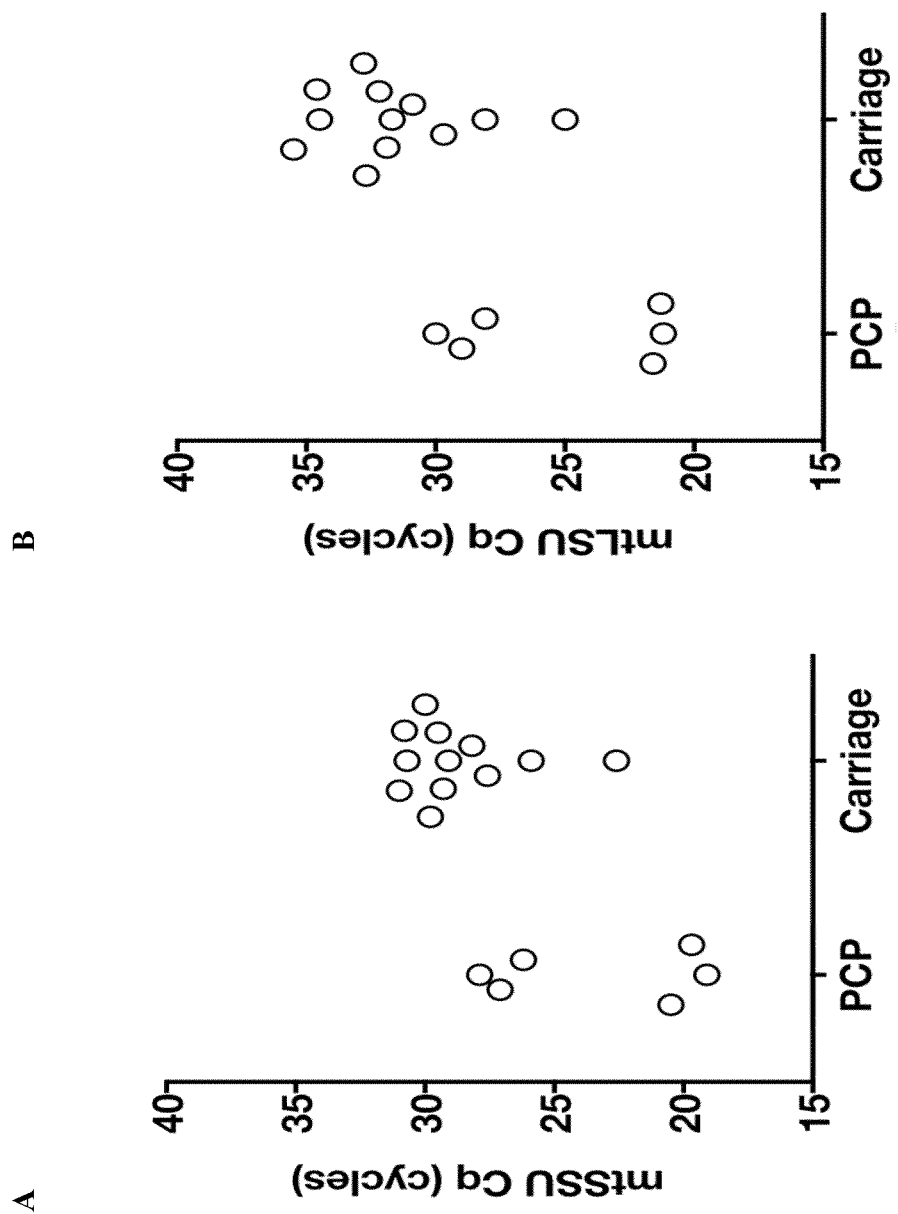
FIGS. 8A and 8B: distribution of the mtSSU (FIG. 8A on the left) and mtLSU (FIG. 8B on the right) quantification cycles in the BAL fluid samples of PCP patients and of *P. jirovecii* carrier (but non-PCP) patients.

FIG. 8 shows the distribution of quantification values (cycles) of the RNA transcripts of the mtSSU et mtLSU genes in the PCP patients and in the carrier patients.

BIBLIOGRAPHIC REFERENCES

Alanio et al. 2011. Real-time PCR assay-based strategy for differentiation between active *Pneumocystis jirovecii* pneumonia and colonization in immunocompromised patients. *Clin Microbiol Infect* 2011; 17: 1531-7.

Pfaffl 2001. A new mathematical model for relative quantification in real-time RT-PCR. *Nucleic Acids Res* 2001; 29: e45.

Wang et al. 2009. RNA-Seq: a revolutionary tool for transcriptomics. *Nat. Rev. Genet.* 2009 January; 10(1): 57-63.

The invention claimed is:

1. An in vitro method for diagnosing whether a human patient, who is a *Pneumocystis jirovecii* carrier, has *Pneumocystis* pneumonia (PCP) or is at an elevated risk of developing PCP, the method comprising:

A) providing a sample comprising RNA obtained from the respiratory tract of a human patient by a process comprising extracting and/or purifying the RNA material of a biological sample from the respiratory tract of the human patient in the presence of an RNA extraction internal control;

B) quantifying in the sample RNA transcripts of a first *P. jirovecii* mitochondrial gene, wherein the first mitochondrial gene codes for the Cytb protein or transcribes into a *P. jirovecii* ribosomal RNA; and C) quantifying in the sample RNA transcripts of a second *P. jirovecii* mitochondrial gene, wherein the second mitochondrial gene transcribes into a *P. jirovecii* ribosomal RNA;

wherein the quantification of B) and C) is performed by (cDNA) reverse-transcription and PCR amplification;

wherein the first and the second *P. jirovecii* mitochondrial genes are different;

wherein a ratio of the value of quantification of the RNA transcripts of the first *P. jirovecii* mitochondrial gene to the value of quantification of the RNA transcripts of the second *P. jirovecii* mitochondrial gene that is equal to or lower than a threshold value indicates that the human patient has PCP or an elevated risk of developing PCP;

wherein a ratio of the value of quantification of the RNA transcripts of the first *P. jirovecii* mitochondrial gene to the value of quantification of the RNA transcripts of the second *P. jirovecii* mitochondrial gene that is higher than the threshold value indicates that the human patient does not have PCP or an elevated risk of developing PCP;
wherein the threshold value has been predetermined by comparing the values, or the distribution of the values, that the ratio of the value of quantification of the RNA transcripts of the first *P. jirovecii* mitochondrial gene to the value of quantification of the RNA transcripts of the second *P. jirovecii* mitochondrial gene takes in reference human cohorts of *P. jirovecii* carriers, who have been pre-established as a function of their status of
*P. jirovecii* carriers, who have or develop PCP, or
*P. jirovecii* carriers, who do not have and do not develop PCP.

2. An in vitro method for determining or predicting the efficacy of a drug or treatment against *Pneumocystis* pneumonia (PCP) in a human patient, who is a *Pneumocystis jirovecii* carrier and/or who has been diagnosed with PCP, the method comprising:
  A) providing a sample comprising RNA obtained from the respiratory tract of a human patient by a process comprising extracting and/or purifying the RNA material of a biological sample from the respiratory tract of the human patient in the presence of an RNA extraction internal control;
  B) quantifying in the sample RNA transcripts of a first *P. jirovecii* mitochondrial gene that codes for the Cytb protein or that transcribes into a *P. jirovecii* ribosomal RNA at a first point in time and a second point in time that is later than the first point in time;
  C) quantifying in the sample RNA transcripts of a second *P. jirovecii* mitochondrial gene that transcribes into a *P. jirovecii* ribosomal RNA at the first point in time and the second point in time;
  wherein the quantification of B) and C) is performed by (cDNA) reverse-transcription and PCR amplification;
  wherein the first and the second *P. jirovecii* mitochondrial genes are different;
  wherein at least one of said first and second points in time is comprised in a time period during which the human patient is receiving the drug or treatment; and
  wherein when the ratio of the value of quantification of the RNA transcripts of the first *P. jirovecii* mitochondrial gene to the value of quantification of the RNA transcripts of the second *P. jirovecii* mitochondrial gene is higher at the second point in time than the first point in time, this indicates that the treatment or drug is effective to treat or alleviate PCP in the human patient.

3. The method of claim 1 or 2, wherein the human patient is HIV-negative.

4. The method of claim 1 or 2, wherein the first mitochondrial gene is the mitochondrial *P. jirovecii* Large Sub-Unit (mtLSU) gene or the mitochondrial *P. jirovecii* Small Sub-Unit (mtSSU) gene; and/or
  wherein the second mitochondrial gene is the mitochondrial *P. jirovecii* Large Sub-Unit (mtLSU) gene or the mitochondrial *P. jirovecii* Small Sub-Unit (mtSSU) gene.

5. The method of claim 1 or 2, wherein the second mitochondrial gene is the mitochondrial *P. jirovecii* Large Sub-Unit (mtLSU) gene.

6. The method of claim 1 or 2, wherein the first mitochondrial gene codes for the Cytb protein or is the mitochondrial *P. jirovecii* Small Sub-Unit (mtSSU) gene.

7. The method of claim 1 or 2, wherein the first mitochondrial gene codes for the Cytb protein, and wherein the second mitochondrial gene is the mitochondrial *P. jirovecii* Large Sub-Unit (mtLSU) gene.

8. The method of claim 7, wherein the threshold value is in the 1.27-1.66 range.

9. The method of claim 7,
  wherein the ratio of the value of quantification of the RNA transcripts of the first *P. jirovecii* mitochondrial gene to the value of quantification of the RNA transcripts of the second *P. jirovecii* mitochondrial gene is defined as:

$$R = E(\text{CYTb})^{-Cq(CYTb)} / E(\text{mtrDNA})^{-Cq(mtrDNA)}$$

wherein
  R is the ratio,
  CYTB is the cDNA reverse-transcript of the RNA transcripts of the gene that encodes the Cytb protein,
  mtrDNA is the cDNA reverse-transcript of the RNA transcripts of the mitochondrial *P. jirovecii* Large Sub-Unit (mtLSU) gene,
  E is the value of the PCR efficiency of one amplification cycle in the exponential phase for the indicated cDNA, and
  Cq is the value of the PCR quantification cycle for the indicated cDNA.

10. The method of claim 1 or 2, wherein the first *P. jirovecii* mitochondrial gene is the mitochondrial *P. jirovecii* Small Sub-Unit (mtSSU) gene, and wherein said second *P. jirovecii* mitochondrial gene is the mitochondrial *P. jirovecii* Large Sub-Unit (mtLSU) gene.

11. The method of claim 10, wherein the threshold value is in the 2.7-3.3 range.

12. The method of claim 10, wherein the ratio of the value of quantification of the RNA transcripts of the first *P. jirovecii* mitochondrial gene to the value of quantification of the RNA transcripts of the second *P. jirovecii* mitochondrial gene is defined as:

$$R = E(\text{mtSSU})^{-Cq(mtSSU)} / E(\text{mtLSU})^{-Cq(mtLSU)}$$

wherein
  R is the ratio,
  mtSSU is the cDNA reverse-transcript of the RNA transcripts of the mitochondrial *P. jirovecii* Small Sub-Unit (mtSSU) gene,
  mtLSU is the cDNA reverse-transcript of the RNA transcripts of the mitochondrial *P. jirovecii* Large Sub-Unit (mtLSU) gene,
  E is the value of the PCR efficiency of one amplification cycle in the exponential phase for the indicated cDNA, and
  Cq is the value of the PCR quantification cycle for the indicated cDNA.

13. The method of claim 1 or 2, wherein the quantification of the respective RNA transcripts comprises:
  the cDNA reverse transcription of a first RNA target contained in the RNA transcripts of the first *P. jirovecii* mitochondrial gene using a first primer pair to obtain first cDNA reverse-transcripts, and the PCR amplification of the first cDNA reverse-transcripts using the same first primer pair to obtain first amplicons; and
  the cDNA reverse transcription of a second RNA target contained in the RNA transcripts of the second *P. jirovecii* mitochondrial gene using a second primer pair to obtain second cDNA reverse-transcripts, and the PCR amplification of the second cDNA reverse-transcripts using the same second primer pair to obtain second amplicons;
  wherein the method further comprises the quantification of the first amplicons and the second amplicons;

wherein the value of quantification of the first amplicons is the value of quantification of the RNA transcripts of the first *P. jirovecii* mitochondrial gene, and the value of quantification of the second amplicons is the value of quantification of the RNA transcripts of the second *P. jirovecii* mitochondrial gene.

14. The method of claim 13;
wherein when the first *P. jirovecii* mitochondrial gene codes for the Cytb protein, the first RNA target consists of 100-120 nucleotides and comprises or is the sequence of SEQ ID NO: 29, or an RNA sequence that is of the same length as SEQ ID NO: 29 and is at least 95% identical to SEQ ID NO: 29; and
wherein when the first *P. jirovecii* mitochondrial gene is the mitochondrial *P. jirovecii* Small Sub-Unit (mtSSU) gene the first RNA target consists of 60-110 nucleotides and comprises or is the sequence of SEQ ID NO: 14, SEQ ID NO: 19 or SEQ ID NO: 24, or an RNA sequence that is of the same length as SEQ ID NO: 14, SEQ ID NO: 19, or SEQ ID NO: 24 and is at least 95% identical to SEQ ID NO: 14, SEQ ID NO: 19 or SEQ ID NO: 24, respectively.

15. The method of claim 13;
wherein the second *P. jirovecii* mitochondrial gene is the mitochondrial *P. jirovecii* Large Sub-Unit (mtLSU) gene, the second RNA target consists of 115-125 nucleotides and comprises or is the sequence of SEQ ID NO: 9, or an RNA sequence that is of the same length as SEQ ID NO: 9 and is at least 95% identical to SEQ ID NO: 9.

16. The method of claim 1 or 2;
wherein when the first *P. jirovecii* mitochondrial gene is the *P. jirovecii* Cytb gene, the quantification of the RNA transcripts of the first *P. jirovecii* mitochondrial gene is performed using a first probe that hybridizes to SEQ ID NO: 30 or to the complementary sequence thereof, without hybridizing to any of SEQ ID NO: 1, the sequence complementary to SEQ ID NO: 1, SEQ ID NO: 2 and the sequence complementary to SEQ ID NO: 2; and
wherein when the first *P. jirovecii* mitochondrial gene is the mitochondrial *P. jirovecii* Small Sub-Unit (mtSSU) gene, the quantification of the RNA transcripts of the first *P. jirovecii* mitochondrial gene is performed using a first probe that hybridizes to SEQ ID NO: 15, or to the sequence complementary to SEQ ID NO: 15, or to SEQ ID NO: 20, or to the sequence complementary to SEQ ID NO: 20, or to SEQ ID NO: 25, or to the sequence complementary to SEQ ID NO: 25, without hybridizing to any of SEQ ID NO: 3, the sequence complementary to SEQ ID NO: 3, SEQ ID NO: 1 and the sequence complementary to SEQ ID NO: 1; and
wherein when the second *P. jirovecii* mitochondrial gene is the mitochondrial *P. jirovecii* Large Sub-Unit (mtLSU) gene, the quantification of the RNA transcripts of the second *P. jirovecii* mitochondrial gene is performed using a second probe that hybridizes to SEQ ID NO: 10 or to the sequence complementary to SEQ ID NO: 10, without hybridizing to any of SEQ ID NO: 3, the sequence complementary to SEQ ID NO: 3, SEQ ID NO: 2 and the sequence complementary to SEQ ID NO: 2.

17. The method of claim 16, wherein the second probe comprises SEQ ID NO: 13.

18. The method of claim 16, wherein the quantification of the RNA transcripts of said second *P. jirovecii* mitochondrial gene is performed using a primer comprising SEQ ID NO: 11 and a primer comprising SEQ ID NO: 12.

19. The method of claim 17, wherein the quantification of the RNA transcripts of said second *P. jirovecii* mitochondrial gene is performed using a primer comprising SEQ ID NO: 11 and a primer comprising SEQ ID NO: 12.

* * * * *

SEQUENCE LISTING

<160> NUMBER OF SEQ ID NOS: 60

<210> SEQ ID NO 1
<211> LENGTH: 2704
<212> TYPE: DNA
<213> ORGANISM: Pneumocystis jirovecii

<400> SEQUENCE: 1

| | | | | | |
|---|---|---|---|---|---|
| aaagggggtta | ttaaggataa | ctagctaata | tatttaagga | ggtgtcgaat | ccaaaatcat | 60 |
| tattctaaag | atgtaataat | gtaaatccga | gagggaaacc | tcaatactaa | ttacgaagtg | 120 |
| aaatgaaaca | tcttagtaac | tttaggaaaa | gaaatcaacc | gagattttat | gagtagtggt | 180 |
| gagcgaaagt | aaattagcca | agtatttata | taatagatta | aatataatta | attacaaaaa | 240 |
| ttaattgtag | tcttcgaatg | aaagatcaat | ctcctctttt | aaaagttgga | atgctttagc | 300 |
| caaggatggt | gaaagcccag | agtcccagga | atataaatac | aaaataagta | gaacgagaga | 360 |
| taacttgttt | gaatacagat | aatatttatg | tagtaatgta | tggaacaatt | caactttata | 420 |
| ctaattacac | ataagattat | taggggaact | atcctctaag | gctaaatata | atatattaag | 480 |
| cgatagtgaa | gagtaccgtg | agggaaagtt | gaaaagaata | taagtgaaac | agatcttgaa | 540 |
| ttaataaccct | tataagcagt | cggaggtcca | aagactgacg | acgtaccttt | tgcataatgg | 600 |
| gtcagcaagt | taatatgcaa | tgcaagtcgc | aagacctaat | gaagatgatt | ctgaacaggg | 660 |
| atataaagta | ttgtgtatta | gacccgaaat | ctagtgatct | tactatgatc | agacaacttc | 720 |
| aggtcgaact | ggtgtacgtc | gcaaagtact | cagaagaatt | gtggtaagta | gtgaaataca | 780 |
| aatcggacta | ggatatagct | ggtttttctgc | gaaaattgtt | ttggcaaatt | gtttattcct | 840 |
| ctaaaaaata | gtaggtatag | cactgaatat | ctcgagggag | tatgaaaata | tttatctcag | 900 |
| atatttaatc | tcaaaataac | tatttcttaa | aataaataat | cagactatgt | gcgataaggt | 960 |
| agatagtcga | aagggaaaca | gcccagaaca | gtaattaaag | ctccccaatt | aatattaagt | 1020 |
| gaaataaaag | ttgttggata | tctaaaacag | ttaagaagtg | ggcttggaaa | cagccatctt | 1080 |
| ttaaagaaca | cgtaaaagtg | caatgatcta | tgatctccag | cgctgaaaat | atccggatct | 1140 |
| aaatattatg | ctgaaagact | gtttatttttt | cttttaatta | actgtaatttt | aattaaaaaa | 1200 |
| aataaggtag | cagaacattt | agtaaatgtg | tgaagaatag | tattttatta | ttcggacata | 1260 |
| actaaagaga | gaatgctgac | atgagtaacg | ttaaaatagg | tgaaaatcct | attcgccgaa | 1320 |
| aatggaaggt | ttttatagtt | ccgcttaact | actataaatc | agatcggtct | ctaacagtaa | 1380 |
| ttcgaatgaa | taatggatga | gaaacatata | taaaaatcgt | aagattcagg | aaaaattata | 1440 |
| tgtaataacc | gtactaaaac | cgacacaggt | ccatgaatat | taatgtatac | aggcgaatga | 1500 |
| gagaattatt | gcgaaggaac | tcggcaaatg | aatttcgtaa | tttcgagata | agaaatacca | 1560 |
| atggtgtcaa | taatgaggtt | gtacaactgt | ttacttaaaa | cacagtactt | tgcaaagatt | 1620 |
| aaaaatcatt | gtataaagta | tgaaatctgc | ccaatgctaa | atgataaaat | ctatggcttc | 1680 |
| aatggctgtg | ggtataatgt | ttagtgaatg | gcggccttaa | ctataagggt | cctaaggtag | 1740 |
| cgaatttcct | tggccgttaa | atgcggtccc | gcacgaatga | tttaatgata | caacaactgt | 1800 |
| ctccgcaata | aactcagtga | aattggatta | gccgtgaaga | tacggtttgt | atatagatag | 1860 |
| acgggaagac | cctatgcagc | ttaactgttg | ttctttattg | tttttttaaa | ttctcttctg | 1920 |
| tagtgctaaa | aggtagtcga | tgagatgtca | gtgaaaaacc | tttgtggaaa | tttaaaataa | 1980 |
| ctaacttact | taattaagaa | cagtgaagat | tagacagttt | ctgtggggcg | cagatctcaa | 2040 |
| aaattgtatc | tgagatgccc | aaaggcatgg | tgaaattgga | tggtaaccaa | tgaatgtaca | 2100 |

| | |
|---|---|
| tttgtatatc tagtggtctt taattactag atgatgtttt atttaataaa gtgtaatggc | 2160 |
| ataactcatg cttaacagta agactaacaa gtcaaactga catgtaagtg gggcataatg | 2220 |
| accctcgttt acattatgga ttggaacgag agtaacgaat aaaagctacg ctagggataa | 2280 |
| cagggttatt tcgtgtgaga gatcgtattg accacgaagt tgccacctc gatgtcgact | 2340 |
| caacctatcc tccaggagta gaatattgga agggttcggc tgttcgccga ttaaaaggtt | 2400 |
| acgtgagttg ggttaaaaac gttgtgaaac agtttggttc ctatcttcta tatattttaa | 2460 |
| aagttaatgg agaatttact ctttgtacgc aaggatcaga tgtattttaa cctctggttt | 2520 |
| gtctgttgtt tgtcgcatcg cagatacgct atgttgatac ggaataaata ttgaaagcat | 2580 |
| attaaatatg aagtcctact ccataaactt tcttgcgttg tagactacga cgtagatagg | 2640 |
| ctttatctgt aagaatagta atgttttaag gtataaagta ctaattttttt tttgactgaa | 2700 |
| ttat | 2704 |

<210> SEQ ID NO 2
<211> LENGTH: 1438
<212> TYPE: DNA
<213> ORGANISM: Pneumocystis jirovecii

<400> SEQUENCE: 2

| | |
|---|---|
| taagataatt cacaaaagaa agagtttaat gttagctccg aatcaacgct atctagaggc | 60 |
| attacacatg caaatcgtac gtttaaagtg gtgaacaggt gagtaaagat agaaatctac | 120 |
| ctattcataa ggttagatac cttttaaaag aacaattgtt tgtgaataga tgagtctaag | 180 |
| tgggggaggt agttgtgagg tgaagatcct cccaagccta agaaccctag ttatatttga | 240 |
| aagaatgaat aacccacattg gctctgaaac aacagccaag attttcatcc aagaaagtcc | 300 |
| agcagtgggg aatattggtc aatgatcgaa agattgaacc agctatctag aagaatttgt | 360 |
| attctgttat tagagaggat tatgacgtta tctaattaaa gtctcgacca attctcgtgc | 420 |
| cagcagtcgc ggtaagacga gtgaggctag cgttattcat aattattagg ctaaagggt | 480 |
| acgtagatgg ttaacttatc tgttatttat gtgtgaagga attagtattc taattcgttt | 540 |
| tattagtatt ctaattttttt taatagaaca taaaagaatt ggataaattg attaactaga | 600 |
| gtcgaataga agaataaaga atttttaagag tagagatgaa attcaacgat acttaaagga | 660 |
| ctgccaatgg cgaaagcatt attctaggta acgactgaca ttgaggtacg taggcataag | 720 |
| tagcgaaaag gattagatac ccttgtagtt tatgctgtaa acgatgaatg ctagaggtca | 780 |
| gaatttattt attttttggtc tttaagtgaa gatttttaagc attccacctg agaagtactg | 840 |
| tcgcaagact gaaactcaaa acattagacg gtcacagaga tcagcagtga agcatgttgt | 900 |
| ttaattcgat aacccacgat aaatcttacc acttcttgca tattttccta ttcggaattt | 960 |
| acaggtgttg catggctgtc tttagttcgt gttgtgaaat gttaggttta ttccgataac | 1020 |
| gaacgtaaac cttgtcctta attatttttaa ggaaatgtct atcgatatta tagatgaatg | 1080 |
| aggatgaaga caagtcctca tgaccttat gaagtgggct acagacgtgc tgcaaaattt | 1140 |
| tctacaatgg gatgcaatga tggaagtcgg agctaatccc ctaaaagatt gtttagtccg | 1200 |
| gataagtgcc tggaactcgg ctctttgaag ttggaattgc tagtaatcgt ctatcatcat | 1260 |
| gagacggtga atctttatc tgtgatgtac taactactcg tcaagcgcgg aaatttttta | 1320 |
| agaaattcaa gttcttacgt ccatttcttg gagatctgtg ctaagtcgaa ataaggtagc | 1380 |
| tgtaggggaa ccctgtagct gaataatttg tgttgtttaa atcccccca tccttgtg | 1438 |

<210> SEQ ID NO 3
<211> LENGTH: 1038
<212> TYPE: DNA
<213> ORGANISM: Pneumocystis jirovecii

<400> SEQUENCE: 3

| | | | | | |
|---|---|---|---|---|---|
| tatttatgga | attatggttc | attatcagga | ctgtgtttaa | ttatacagat | tattacgggt | 60 |
| gtgactttag | ctatgcatta | tataccttcg | attgatttag | ctttcttgag | tgttgaacat | 120 |
| attatgtgag | atgtaaatta | tggttggttg | attcgttata | ttcatagtaa | tacggcttct | 180 |
| ttttctttc | tgtttgttta | tattcatatt | gcttgaggta | tctattatgg | atcttatcga | 240 |
| actcccagaa | ttctcgtttg | gtctattggt | gtagttatct | tcttaattat | gattgttact | 300 |
| gctttcttgg | gatatgttct | gccttttggt | caaatgtcat | tgtggggagc | gactgttatt | 360 |
| actaatttga | tgtctgctat | accttggatt | ggtaatgata | ttgtgaattt | tatttggggt | 420 |
| gggttctctg | ttaatcatgc | tactctgaat | tgattcttct | ctttacatta | tttattgcct | 480 |
| tttgttttat | tggctttagt | tgttgctcat | ttaatctctt | tacatgttca | tggaagtagt | 540 |
| aatcctctgg | gtgttactgg | taattcagat | cgtctgcctt | tccatcccta | tttctcattt | 600 |
| aaagattag | ttactgtttt | tttatttta | ttagcttat | ctttctttgt | gttttatgct | 660 |
| cctaatgtct | tgggacatag | tgataattat | attatggcta | atcctatggc | tactcctcca | 720 |
| agtattgttc | ctgaatggta | tcttttacct | ttctatgcaa | tcttgtgatc | tatttcgaat | 780 |
| aaattatttg | gagttgtggc | tatgttagct | gctattctta | ttctttttgt | tttacctctt | 840 |
| gtggatttat | cttgaatttg | aggttctgct | tttagacctc | ttagtaaatt | cttttttttgg | 900 |
| atctttgtca | ctaatttctt | cttgttaatg | tttgtgggtt | cacaacatgt | tgaagaacct | 960 |
| tttgtgacgc | ttgacaata | tgctacattc | ttctatttct | tctatttctt | agttgttatt | 1020 |
| cctctggtgg | gtattatt | | | | | 1038 |

<210> SEQ ID NO 4
<211> LENGTH: 1437
<212> TYPE: DNA
<213> ORGANISM: Pneumocystis jirovecii

<400> SEQUENCE: 4

| | | | | | |
|---|---|---|---|---|---|
| ggcgcctctt | tttggagcac | cattagcggt | gaacacggtc | ttgatagcac | tggcctgtaa | 60 |
| gcaatattgt | aatactgcag | tgtgtttgca | gaggtgatta | gaaatgccta | taaggcagca | 120 |
| aaaaggcatt | gaaagactc | caaagaagta | taaagatgct | ctgcaaacaa | tctaaaaaca | 180 |
| tgcagtaata | ctgcatgttt | gcagtacttt | ttttccaaaa | cttatatttt | tcagctatca | 240 |
| tggaaccctct | gatctccaac | tcgaacggat | gaatgtttat | ttcaacgagg | tttctacgga | 300 |
| aaaatgttta | tagaatgtca | gacatttatt | ttaataggca | tctggtggga | aatacgtgcc | 360 |
| tcgtgcagta | ctggttgatt | tagagcccgg | tacaatggat | gcagtacgtt | ctgggccatt | 420 |
| tgggaacctg | tttcgaccag | ataatttat | ttttggtcaa | tcaggtgcag | gaaataactg | 480 |
| ggcaaaaggg | cattatacag | agggagcgga | attggtagat | actgtgttag | atgtagttcg | 540 |
| tcggaagcc | gaagcatgtg | attgcttgca | aggattccag | attacacatt | cattaggtgg | 600 |
| tggaacgggt | gcaggcatgg | gaactttgct | aatttcgaaa | attcgagagg | aatatccgga | 660 |
| tcggatgatg | gcaacgtttt | cagtggttcc | ctcaccaaaa | gtttccgata | cagttgtaga | 720 |
| gccatataat | gcaacattat | cagtgcatgt | gtgttttaa | gccatttta | gaatgtatat | 780 |
| taatgaggag | gggtagcaat | tagttgaaaa | ttccgatgaa | acattctgta | tcgacaatga | 840 |

-continued

```
agcattatat gatatttgta tgcgtacatt aaaattgccg gatccaggat atggtgattt    900
gaatcatctt gtctcggcag taatgagtgg tattacaact tgtcttcgat ttcctggaca    960
actcaactcg gatttgcgta aattggccgt taatatggtg ccgtttcctc gtttgcactt   1020
tttcatggtt gggtttgctc cattaacaag cagtaagatg ctttaaacgt attctgaaat   1080
ggctgattgt tattctgtct agagggatca cattcatttc ggtcattgac agttcctgaa   1140
ttgactcagc aaatgtttga tgcaaagaat atgatggcag catcggatcc gagacatggt   1200
cgctatttaa ctgttgcagc gattttccgc ggtactgttt ccatgaagga ggttgaagat   1260
caaatgcata atgttcagca gaagaactct tcatattttg ttgaatggat tccaaacaat   1320
gtgcaaaccg cgctatgttc tattccacca cgtggtctca aaatgtcatc aacgtttatt   1380
ggcaattcaa catctattca ggaactattt aaacgtgtag gcgaccaatt tgctgca      1437
```

<210> SEQ ID NO 5
<211> LENGTH: 977
<212> TYPE: DNA
<213> ORGANISM: Pneumocystis jirovecii

<400> SEQUENCE: 5

```
gacggaaatt cggggatcca gaagtgcaat cagatatgaa acattggcct tttaaagtta    60
tagacaaagg tcagaagcct tatattcagg ttgaatataa aggggatatt aaaacattta   120
cgccggagga gatttcatca atggtcctta caaaaatgaa ggaggtggca gaagcgtatc   180
ttgggactaa agtttccaat gccgttatca cggtcccagc atatttcaat gattcacagc   240
gacaggctac gaaagacgca ggattgattg caggattgaa tgttttacgt attatcaatg   300
aacctacagc agcagccatt gcatatggtc tagataagaa gacatcaaat gaaaagaatg   360
tgcttatttt tgatcttgga ggaggaactt ttgacgtatc gttattaact atcgaagagg   420 gaattttga gtcaaagca accgcaggcg atacccattt gggaggagaa gattttgaca   480
atcgtcttgt aaaccacttc attgctgaac gcaaacacaa gaaagatctt tcagggaatg   540
cacgatctct tcgtcggctt cgaacagcat gtgagcgtgc taaacggact ctttcatcat   600
caacacagac gagtatagaa attgattcct tatttgaagg aattgattta tacttcta    660 ttactcgtgc tcgatttgaa gactttgtc aaggtctttt taggggaaca atggaaccag   720
ttgagaaagt tcttcgtgat tctaaaattg ataaatcaag tgttcatgaa attgtattgg   780
ttggtggttc tacgcgtatt ccgcgtattc agaaattggt tgtgatttt tttaatggaa   840 aagagccaaa tagaacgatc aatccagatg aggctgttgc ctatggtgcg gcagttcaag   900
ttgctattct ttcaggagac acatcggaac aaactcaaga catactcttg cttgatgtgg   960
cgcctctctc aatgggt                                                  977
```

<210> SEQ ID NO 6
<211> LENGTH: 1581
<212> TYPE: DNA
<213> ORGANISM: Pneumocystis jirovecii

<400> SEQUENCE: 6

```
atgacatgat ggttgttttc aacaaatgct aaggatatcg gagtcttgta cttgatcttt    60 gcacttttt ctggaatgtt gggtacagca tattcagtat tattgagaat ggaattaact   120
tccccaggtg ttcagtattt acagggtgat aatcaattgt ataatgtaat tttaacgagt   180
catgcgttgt taatgatatt ctttatggtt atgcccggaa tggtaggagg ttttggtaat   240
```

```
tggttggttc cagtaatgat ggagcacca gatatggcct ttccaagatt aaataatatc      300
tccttctggt tgttaccgcc ttctctgatt ctgttaattg cttcttctct tctagaaggt      360
ggaagtggta caggttggac ttttatcca cctttgtcca gtttacaaag tcattcctca      420
ggtgctgtcg atttgtctat ctttagtcta catttagcag gtattagttc tatgttggga      480
gctattaatt ttattactac tgttcttaat acttgagctc ccggtatgac tatgcataaa      540
attccattgt ttgtatggtc tatctttgtt actgctatac tgttgttatt gtccttgcca      600
gtcttagcag gaggtattac tatgctcttg acggattgaa attttaatac ttccttctat      660
gatgtcgcag gaggagggga tcctatcctt tatcaacatc tcttctggtt cttcggacat      720
ccagaagttt atattctgat tattccagga tttggtatca ttagtcatat tatttccact      780
ttctctggaa aaccagtatt cggttatta ggtatggttt atgctatgtt gtcaattggt      840
gtcttaggat ttattgtctg gagtcatcat atgtattcag tgggtttaga tgttgataca      900
tgagcttatt ttactgctgc tactatgatt attggtgtac ctactggtat aaaaatcttc      960
tcttggattg ctactatgta tggtggtgtg attcgattta atacacctat gctctttgct     1020
atcggattcc ttttccttt tactgtggga ggattaacgg gtattgtctt gtctaatgct     1080
tctttagatg tggctttaca tgatacttat atgttgtag ctcatttcca ttatgtttta     1140
tccatgggtg cagtctttgc tctcttagca gcttggtatt tctggtctcc aaaaatttta     1200
ggattgttct tgatgaaaaa attagggcat ttgcatttct ggactctttt tattggagtg     1260
aatttaactt ttatgcctat gcatttcttg ggattacagg gtatgccag atgaattcct     1320 gattatcctg atgcttttgc tcagtggaat catatctcaa gtttaggtag tttgatttct     1380
gttgttgcta ctgttgtttt tatttattct attttttgatc aattgatctc taaatgattg     1440
gtaccgatga atccttggta ttctcctgat ttctttgtta gtcatacgaa tttagaggat     1500
tccaaagctt gttccttaga atgggcattg atttcaccac cagctttcca tgcttatact     1560
agtttaccta aacaagctta a                                               1581
```

<210> SEQ ID NO 7  
<211> LENGTH: 1002  
<212> TYPE: DNA  
<213> ORGANISM: Pneumocystis jirovecii

<400> SEQUENCE: 7

```
atgttaaatt gtattcaagt gggtattgtt ttattacctg ttttgttaag tgtagctttt       60
gtgacattag ctgaacgtaa agttatggga tcgattcaac gacgtgtggg tcctaatgtt      120
gtgggttatt atggtttgtt acaacctgta gctgatgctt taaaattatt attaaaagaa      180
actattattc ctatccattc gaataaagtg ttgttcttct taggaccttc tattgcatta      240
gtctttgctt taatgggttg gggtattatt ccatggaatt caggtataac actttgggat      300
tttgatttag gtatttatt tagtttagct atttcttctt taggtgtgta tggtattta      360 attggggtt gggcttctaa ttccaaatat gctttattag gttccttgtg aagtactgct      420
caattaatta gttatgaatt agttttaact tcgattgttt ttgttgttgt tcttttatct      480 ggttcttta atttttactca cattattgaa gaacaaaaag ctatttggtt tgttttgcct      540
ttatttcctc tgtttatttt gttctttatt ggtgctttag cagaaacgaa ttgagctcct      600
tttgatttgc cagaagctga atccgaatta gttgctgggt ttatgactga gtattctgct      660
gcgatctttg ttttcttctt cctagctgaa tatgctaata ttattcttat ctctactcta      720
gctgctattt tcttcttagg aggttattta ttacctttcg agttgcattt cttgcctaat      780
```

```
ggtttagatg ttctcgttca gggattactt tctggtttga ttttaggttt gaaagttgct      840
gggattattt tcctctttgt ttgggtttga tctagcttcc ctagaatttg atatgatcaa      900
ttgttagttc tatgttggac tgttctgtta cctttgcttt tgcttggat ttttctggtt       960 ttagctattc ttttttcttt taattctttt attcatttct ag                        1002
```

<210> SEQ ID NO 8
<211> LENGTH: 225
<212> TYPE: DNA
<213> ORGANISM: Pneumocystis jirovecii

<400> SEQUENCE: 8

```
atgttacaag cagctaaagt tattggttca gggttagcta caattggatt agcaggggct       60
ggtatcggta tcggtttagt tttcggtaat ttattagtag cgacaagtcg aaatccttca      120
ttgaaaggac aactcttctc ttatgctatc ttgggatttg ctctagcaga agctactggt      180
cttttctgtt tgatgatggc tttccttctg ctatatgcag cttaa                     225
```

<210> SEQ ID NO 9
<211> LENGTH: 121
<212> TYPE: RNA
<213> ORGANISM: Pneumocystis jirovecii

<400> SEQUENCE: 9

```
cacugaauau cucgagggag uaugaaaaua uuuaucucag auauuuaauc ucaaauaac        60 uauuucuuaa aauaaauaau cagacuaugu gcgauaaggu agauagucga aagggaaaca     120
g                                                                    121
```

<210> SEQ ID NO 10
<211> LENGTH: 121
<212> TYPE: DNA
<213> ORGANISM: Pneumocystis jirovecii

<400> SEQUENCE: 10

```
cactgaatat ctcgagggag tatgaaaata tttatctcag atatttaatc tcaaataac        60 tatttcttaa aataaataat cagactatgt gcgataaggt agatagtcga aagggaaaca     120
g                                                                    121
```

<210> SEQ ID NO 11
<211> LENGTH: 26
<212> TYPE: DNA
<213> ORGANISM: Pneumocystis jirovecii

<400> SEQUENCE: 11

```
cactgaatat ctcgagggag tatgaa                                           26
```

<210> SEQ ID NO 12
<211> LENGTH: 26
<212> TYPE: DNA
<213> ORGANISM: Pneumocystis jirovecii

<400> SEQUENCE: 12

```
ctgtttccct ttcgactatc tacctt                                           26
```

<210> SEQ ID NO 13
<211> LENGTH: 19
<212> TYPE: DNA
<213> ORGANISM: Pneumocystis jirovecii

<400> SEQUENCE: 13
tcgcacatag tctgattat                                                     19

<210> SEQ ID NO 14
<211> LENGTH: 82
<212> TYPE: RNA
<213> ORGANISM: Pneumocystis jirovecii

<400> SEQUENCE: 14
gcaaugaugg aagucggagc uaauccccua aaagauuguu aguccggau aagugccugg         60 aacucggcuc uuugaaguug ga                                                 82

<210> SEQ ID NO 15
<211> LENGTH: 82
<212> TYPE: DNA
<213> ORGANISM: Pneumocystis jirovecii

<400> SEQUENCE: 15
gcaatgatgg aagtcggagc taatccccta aaagattgtt tagtccggat aagtgcctgg        60
aactcggctc tttgaagttg ga                                                 82

<210> SEQ ID NO 16
<211> LENGTH: 20
<212> TYPE: DNA
<213> ORGANISM: Pneumocystis jirovecii

<400> SEQUENCE: 16
gcaatgatgg aagtcggagc                                                    20

<210> SEQ ID NO 17
<211> LENGTH: 21
<212> TYPE: DNA
<213> ORGANISM: Pneumocystis jirovecii

<400> SEQUENCE: 17
tccaacttca aagagccgag t                                                  21

<210> SEQ ID NO 18
<211> LENGTH: 25
<212> TYPE: DNA
<213> ORGANISM: Pneumocystis jirovecii

<400> SEQUENCE: 18
tgtttagtcc ggataagtgc ctgga                                              25

<210> SEQ ID NO 19
<211> LENGTH: 92
<212> TYPE: RNA
<213> ORGANISM: Pneumocystis jirovecii

<400> SEQUENCE: 19
ggaugcaaug auggaagucg gagcuaaucc ccuaaaagau uguuuagucc ggauaagugc        60
cuggaacucg gcucuuugaa guuggaauug cu                                      92

<210> SEQ ID NO 20
<211> LENGTH: 92
<212> TYPE: DNA
<213> ORGANISM: Pneumocystis jirovecii

<400> SEQUENCE: 20
ggatgcaatg atggaagtcg gagctaatcc cctaaaagat tgtttagtcc ggataagtgc        60
ctggaactcg gctctttgaa gttggaattg ct                                          92

<210> SEQ ID NO 21
<211> LENGTH: 22
<212> TYPE: DNA
<213> ORGANISM: Pneumocystis jirovecii

<400> SEQUENCE: 21
ggatgcaatg atggaagtcg ga                                                     22

<210> SEQ ID NO 22
<211> LENGTH: 23
<212> TYPE: DNA
<213> ORGANISM: Pneumocystis jirovecii

<400> SEQUENCE: 22
agcaattcca acttcaaaga gcc                                                    23

<210> SEQ ID NO 23
<211> LENGTH: 27
<212> TYPE: DNA
<213> ORGANISM: Pneumocystis jirovecii

<400> SEQUENCE: 23
tgtttagtcc ggataagtgc ctggaac                                                27

<210> SEQ ID NO 24
<211> LENGTH: 76
<212> TYPE: RNA
<213> ORGANISM: Pneumocystis jirovecii

<400> SEQUENCE: 24
ucaugacccu uaugaagugg gcuacagacg ugcugcaaaa uuuucuacaa ugggaugcaa            60
ugauggaagu cggagc                                                            76

<210> SEQ ID NO 25
<211> LENGTH: 76
<212> TYPE: DNA
<213> ORGANISM: Pneumocystis jirovecii

<400> SEQUENCE: 25
tcatgacccT tatgaagtgg gctacagacg tgctgcaaaa ttttctacaa tgggatgcaa            60
tgatggaagt cggagc                                                            76

<210> SEQ ID NO 26
<211> LENGTH: 22
<212> TYPE: DNA
<213> ORGANISM: Pneumocystis jirovecii

<400> SEQUENCE: 26
tcatgaccct tatgaagtgg gc                                                     22

<210> SEQ ID NO 27
<211> LENGTH: 20
<212> TYPE: DNA
<213> ORGANISM: Pneumocystis jirovecii

<400> SEQUENCE: 27
gctccgactt ccatcattgc                                                        20

<210> SEQ ID NO 28

```
<211> LENGTH: 27
<212> TYPE: DNA
<213> ORGANISM: Pneumocystis jirovecii

<400> SEQUENCE: 28
acgtgctgca aaattttcta caatggg                                              27

<210> SEQ ID NO 29
<211> LENGTH: 105
<212> TYPE: RNA
<213> ORGANISM: Pneumocystis jirovecii

<400> SEQUENCE: 29
cucccagaau ucucguuugg ucuauuggug uaguuaucuu cuuaauuaug auuguuacug          60
cuuucuuggg auauguucug ccuuuugguc aaaugucauu guggg                        105

<210> SEQ ID NO 30
<211> LENGTH: 105
<212> TYPE: DNA
<213> ORGANISM: Pneumocystis jirovecii

<400> SEQUENCE: 30
ctcccagaat tctcgtttgg tctattggtg tagttatctt cttaattatg attgttactg          60
ctttcttggg atatgttctg ccttttggtc aaatgtcatt gtggg                        105

<210> SEQ ID NO 31
<211> LENGTH: 20
<212> TYPE: DNA
<213> ORGANISM: Pneumocystis jirovecii

<400> SEQUENCE: 31
ctcccagaat tctcgtttgg                                                     20

<210> SEQ ID NO 32
<211> LENGTH: 20
<212> TYPE: DNA
<213> ORGANISM: Pneumocystis jirovecii

<400> SEQUENCE: 32
cccacaatga catttgacca                                                     20

<210> SEQ ID NO 33
<211> LENGTH: 22
<212> TYPE: DNA
<213> ORGANISM: Pneumocystis jirovecii

<400> SEQUENCE: 33
ctttcttggg atatgttctg cc                                                  22

<210> SEQ ID NO 34
<211> LENGTH: 22
<212> TYPE: DNA
<213> ORGANISM: Pneumocystis jirovecii

<400> SEQUENCE: 34
ccattaacaa gcagggatc ac                                                   22

<210> SEQ ID NO 35
<211> LENGTH: 21
<212> TYPE: DNA
<213> ORGANISM: Pneumocystis jirovecii

<400> SEQUENCE: 35
```

-continued cgatgctgcc atcatattct t                                              21

<210> SEQ ID NO 36
<211> LENGTH: 22
<212> TYPE: DNA
<213> ORGANISM: Pneumocystis jirovecii

<400> SEQUENCE: 36
tcggtcattg acagttcctg aa                                             22

<210> SEQ ID NO 37
<211> LENGTH: 22
<212> TYPE: DNA
<213> ORGANISM: Pneumocystis jirovecii

<400> SEQUENCE: 37
ggagatttca tcaatggtcc tt                                             22

<210> SEQ ID NO 38
<211> LENGTH: 21
<212> TYPE: DNA
<213> ORGANISM: Pneumocystis jirovecii

<400> SEQUENCE: 38
cggcattgga aactttagtc c                                              21

<210> SEQ ID NO 39
<211> LENGTH: 20
<212> TYPE: DNA
<213> ORGANISM: Pneumocystis jirovecii

<400> SEQUENCE: 39
aaggaggtgg cagaagcgta                                                20

<210> SEQ ID NO 40
<211> LENGTH: 24
<212> TYPE: DNA
<213> ORGANISM: Pneumocystis jirovecii

<400> SEQUENCE: 40
aggttttggt aattggttgg ttcc                                           24

<210> SEQ ID NO 41
<211> LENGTH: 21
<212> TYPE: DNA
<213> ORGANISM: Pneumocystis jirovecii

<400> SEQUENCE: 41
agaaggcggt aacaaccaga a                                              21

<210> SEQ ID NO 42
<211> LENGTH: 28
<212> TYPE: DNA
<213> ORGANISM: Pneumocystis jirovecii

<400> SEQUENCE: 42
tggagcacca gatatggcct ttccaaga                                       28

<210> SEQ ID NO 43
<211> LENGTH: 22
<212> TYPE: DNA
<213> ORGANISM: Pneumocystis jirovecii

```
<400> SEQUENCE: 43
agcagaaacg aattgagctc ct                                              22

<210> SEQ ID NO 44
<211> LENGTH: 22
<212> TYPE: DNA
<213> ORGANISM: Pneumocystis jirovecii

<400> SEQUENCE: 44
tcgcagcaga atactcagtc at                                              22

<210> SEQ ID NO 45
<211> LENGTH: 28
<212> TYPE: DNA
<213> ORGANISM: Pneumocystis jirovecii

<400> SEQUENCE: 45
tgccagaagc tgaatccgaa ttagttgc                                        28

<210> SEQ ID NO 46
<211> LENGTH: 24
<212> TYPE: DNA
<213> ORGANISM: Pneumocystis jirovecii

<400> SEQUENCE: 46
ggttcagggt tagctacaat tgga                                            24

<210> SEQ ID NO 47
<211> LENGTH: 23
<212> TYPE: DNA
<213> ORGANISM: Pneumocystis jirovecii

<400> SEQUENCE: 47
aaggatttcg acttgtcgct act                                             23

<210> SEQ ID NO 48
<211> LENGTH: 28
<212> TYPE: DNA
<213> ORGANISM: Pneumocystis jirovecii

<400> SEQUENCE: 48 gcagggggctg gtatcggtat cggtttag                                       28

<210> SEQ ID NO 49
<211> LENGTH: 23
<212> TYPE: DNA
<213> ORGANISM: Homo sapiens

<400> SEQUENCE: 49
tcgttacacc aagaaagtac ccc                                             23

<210> SEQ ID NO 50
<211> LENGTH: 20
<212> TYPE: DNA
<213> ORGANISM: Homo sapiens

<400> SEQUENCE: 50
tgctgcccac ttttcctagg                                                 20

<210> SEQ ID NO 51
<211> LENGTH: 27
<212> TYPE: DNA
<213> ORGANISM: Homo sapiens
```

```
<400> SEQUENCE: 51
agtgtcaact ccaactcttg tagaggt                                          27

<210> SEQ ID NO 52
<211> LENGTH: 20
<212> TYPE: DNA
<213> ORGANISM: Homo sapiens

<400> SEQUENCE: 52
tggcgtgtga agataaccca                                                  20

<210> SEQ ID NO 53
<211> LENGTH: 20
<212> TYPE: DNA
<213> ORGANISM: Homo sapiens

<400> SEQUENCE: 53
cgctggaact cgtctcacta                                                  20

<210> SEQ ID NO 54
<211> LENGTH: 26
<212> TYPE: DNA
<213> ORGANISM: Homo sapiens

<400> SEQUENCE: 54
tgctgagaag agtgtgctgg agatgc                                           26

<210> SEQ ID NO 55
<211> LENGTH: 20
<212> TYPE: DNA
<213> ORGANISM: Homo sapiens

<400> SEQUENCE: 55
atctttgcag tgacccagca                                                  20

<210> SEQ ID NO 56
<211> LENGTH: 20
<212> TYPE: DNA
<213> ORGANISM: Homo sapiens

<400> SEQUENCE: 56
gagcatctcc agcacactct                                                  20

<210> SEQ ID NO 57
<211> LENGTH: 20
<212> TYPE: DNA
<213> ORGANISM: Homo sapiens

<400> SEQUENCE: 57
gagcatctcc agcacactct                                                  20

<210> SEQ ID NO 58
<211> LENGTH: 22
<212> TYPE: DNA
<213> ORGANISM: Pneumocystis jirovecii
<220> FEATURE:
<221> NAME/KEY: misc_feature
<222> LOCATION: (3)..(3)
<223> OTHER INFORMATION: LNA-T
<220> FEATURE:
<221> NAME/KEY: misc_feature
<222> LOCATION: (7)..(7)
<223> OTHER INFORMATION: LNA-T
<220> FEATURE:
```

```
<221> NAME/KEY: misc_feature
<222> LOCATION: (11)..(11)
<223> OTHER INFORMATION: LNA-A
<220> FEATURE:
<221> NAME/KEY: misc_feature
<222> LOCATION: (16)..(16)
<223> OTHER INFORMATION: LNA-T
<220> FEATURE:
<221> NAME/KEY: misc_feature
<222> LOCATION: (20)..(20)
<223> OTHER INFORMATION: LNA-G

<400> SEQUENCE: 58
ctttcttggg atatgttctg cc                                            22

<210> SEQ ID NO 59
<211> LENGTH: 22
<212> TYPE: DNA
<213> ORGANISM: Pneumocystis jirovecii
<220> FEATURE:
<221> NAME/KEY: misc_feature
<222> LOCATION: (3)..(3)
<223> OTHER INFORMATION: LNA-C
<220> FEATURE:
<221> NAME/KEY: misc_feature
<222> LOCATION: (7)..(7)
<223> OTHER INFORMATION: LNA-A
<220> FEATURE:
<221> NAME/KEY: misc_feature
<222> LOCATION: (12)..(12)
<223> OTHER INFORMATION: LNA-T
<220> FEATURE:
<221> NAME/KEY: misc_feature
<222> LOCATION: (16)..(16)
<223> OTHER INFORMATION: LNA-A
<220> FEATURE:
<221> NAME/KEY: misc_feature
<222> LOCATION: (20)..(20)
<223> OTHER INFORMATION: LNA-A

<400> SEQUENCE: 59
ggcagaacat atcccaagaa ag                                            22

<210> SEQ ID NO 60
<211> LENGTH: 20
<212> TYPE: DNA
<213> ORGANISM: Artificial Sequence
<220> FEATURE:
<223> OTHER INFORMATION: P. jirovecii degenerate primer

<400> SEQUENCE: 60
ctcccagaat tctmgtttgg                                               20
```